(12) United States Patent
Ghovanloo et al.

(10) Patent No.: US 8,242,880 B2
(45) Date of Patent: Aug. 14, 2012

(54) TONGUE OPERATED MAGNETIC SENSOR SYSTEMS AND METHODS

(75) Inventors: Maysam Ghovanloo, Atlanta, GA (US); Xueliang Huo, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 250 days.

(21) Appl. No.: 12/474,891

(22) Filed: May 29, 2009

(65) Prior Publication Data

US 2009/0309747 A1 Dec. 17, 2009

Related U.S. Application Data

(60) Provisional application No. 61/057,053, filed on May 29, 2008.

(51) Int. Cl.
G09B 21/00 (2006.01)
(52) U.S. Cl. ........... 340/4.11; 340/4.1; 340/539.12; 340/539.22
(58) Field of Classification Search ........... 340/825.19; 702/116; 600/590; 178/18.03, 18.07; 323/355; 324/207.11
See application file for complete search history.

(56) References Cited

U.S. PATENT DOCUMENTS

| | | | |
|---|---|---|---|
| 4,303,077 A | | 12/1981 | Lewin et al. |
| 4,334,542 A | * | 6/1982 | Takinishi et al. ........... 600/383 |
| 5,460,186 A | * | 10/1995 | Buchhold ................ 600/590 |
| 5,523,745 A | | 6/1996 | Fortune et al. |
| 5,689,246 A | * | 11/1997 | Dordick et al. ........... 341/21 |
| 6,052,610 A | | 4/2000 | Koch |
| 6,263,230 B1 | | 7/2001 | Haynor et al. |
| 6,598,006 B1 | * | 7/2003 | Honda et al. ............. 702/116 |
| 6,801,231 B1 | | 10/2004 | Beltz |
| 6,978,639 B2 | | 12/2005 | Underwood |
| 7,071,844 B1 | | 7/2006 | Moise |
| 7,207,331 B2 | | 4/2007 | Mashak |
| 7,321,226 B2 | * | 1/2008 | Yakymyshyn et al. ... 324/117 R |
| 7,353,134 B2 | | 4/2008 | Cirielli |
| 7,481,224 B2 | | 1/2009 | Nelson et al. |
| 8,044,766 B2 | * | 10/2011 | Ghovanloo et al. ........ 340/4.11 |
| 2009/0051564 A1 | * | 2/2009 | Najanguaq Sovso Andreasen Strujik ............... 340/825.19 |
| 2010/0007512 A1 | * | 1/2010 | Ghovanloo et al. ...... 340/825.19 |
| 2010/0060472 A1 | * | 3/2010 | Kimura et al. ............ 340/686.1 |

FOREIGN PATENT DOCUMENTS

| | | |
|---|---|---|
| WO | WO 2006/105797 | 10/2006 |
| WO | WO 2007/053562 | 5/2007 |
| WO | WO 2008/093334 | 8/2008 |
| WO | WO 2008/114268 | 9/2008 |
| WO | WO 2009/040807 | 4/2009 |
| WO | WO 2009/047768 | 4/2009 |
| WO | WO 2009/047769 | 4/2009 |

* cited by examiner

*Primary Examiner* — Albert Wong
*Assistant Examiner* — Peter Mehravari
(74) *Attorney, Agent, or Firm* — Matthew C. Osborne, Esq.; Ryan A. Schneider, Esq.; Troutman Sanders LLP

(57) ABSTRACT

A method of tracking movement, position, or both of a tongue of a subject. The method includes positioning a tracer unit on the tongue of the subject in a non-obstructively manner; positioning a sensor system in proximity to the tongue carrying the tracer unit; calibrating the sensor system relative to the tracer unit; and detecting the position of the tracer unit. An assistive system/apparatus can track movement, position, or both of the tongue. The system/apparatus includes the tracer unit; the sensor system for detecting position of the tracer unit and adapted for non-obstructive placement proximal the sensor system; and a control system for transmitting to a processing system.

18 Claims, 42 Drawing Sheets

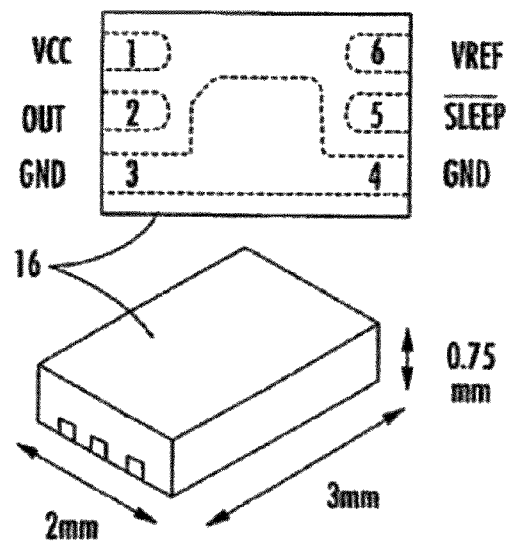
*Fig. 4*
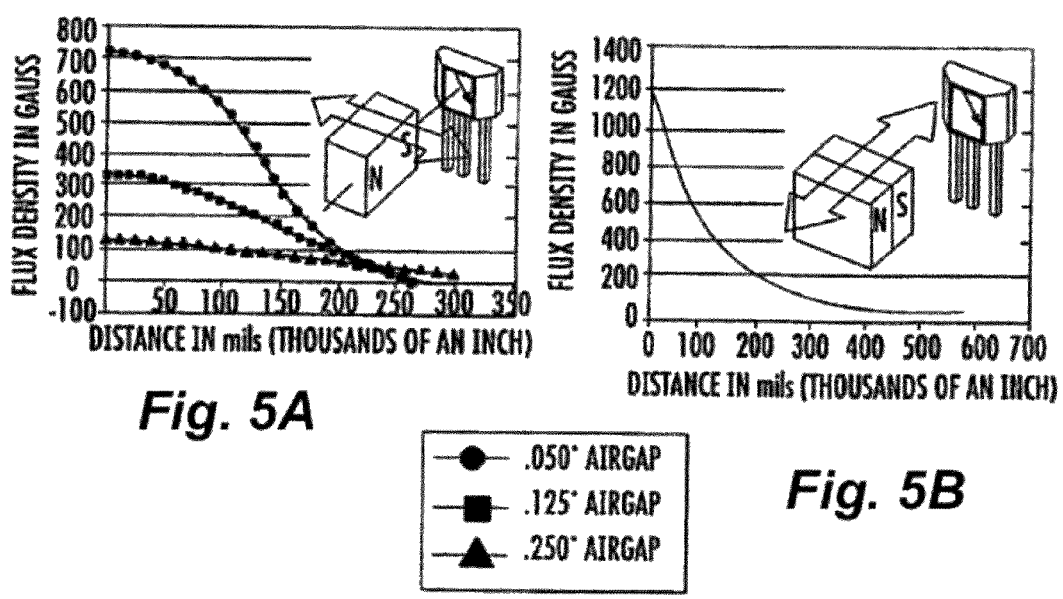
*Fig. 5A*
*Fig. 5B*

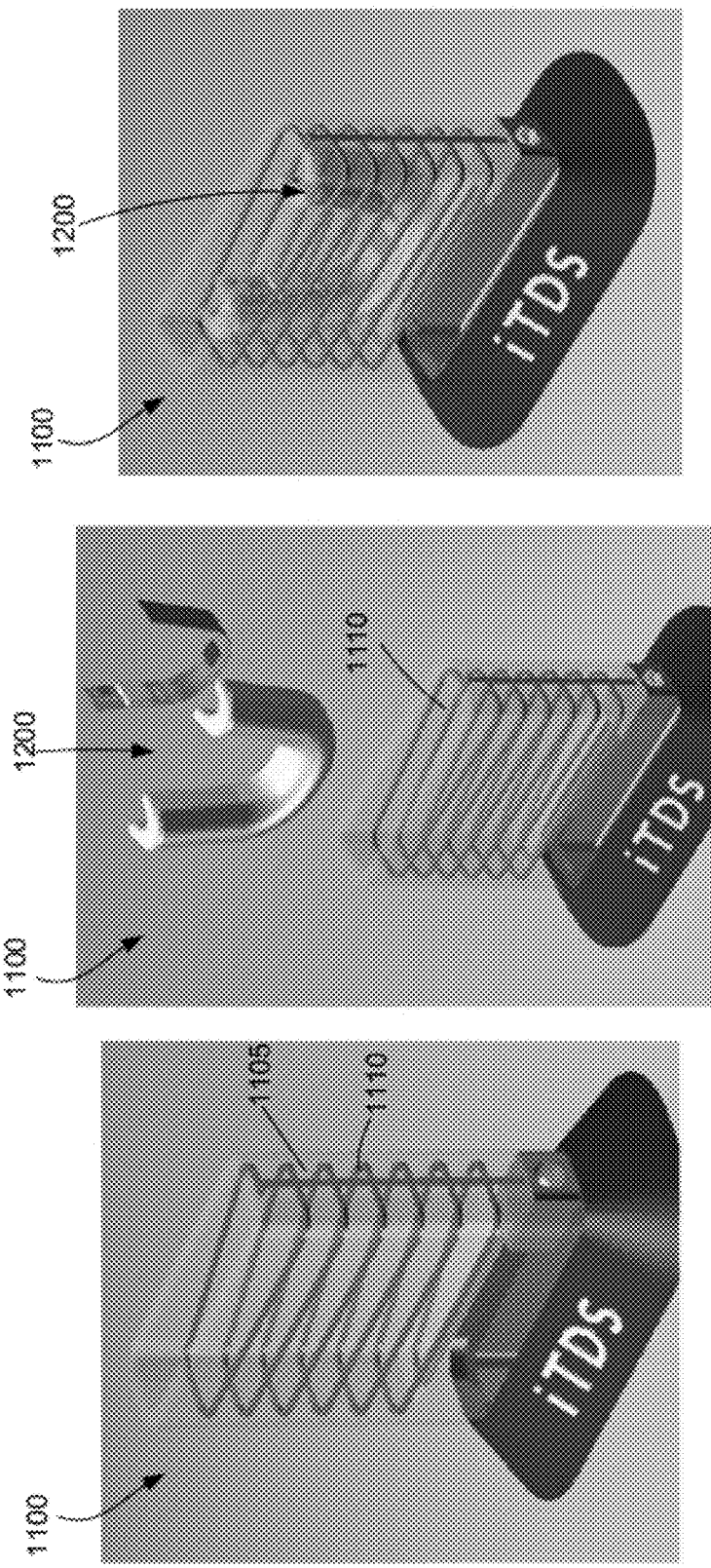

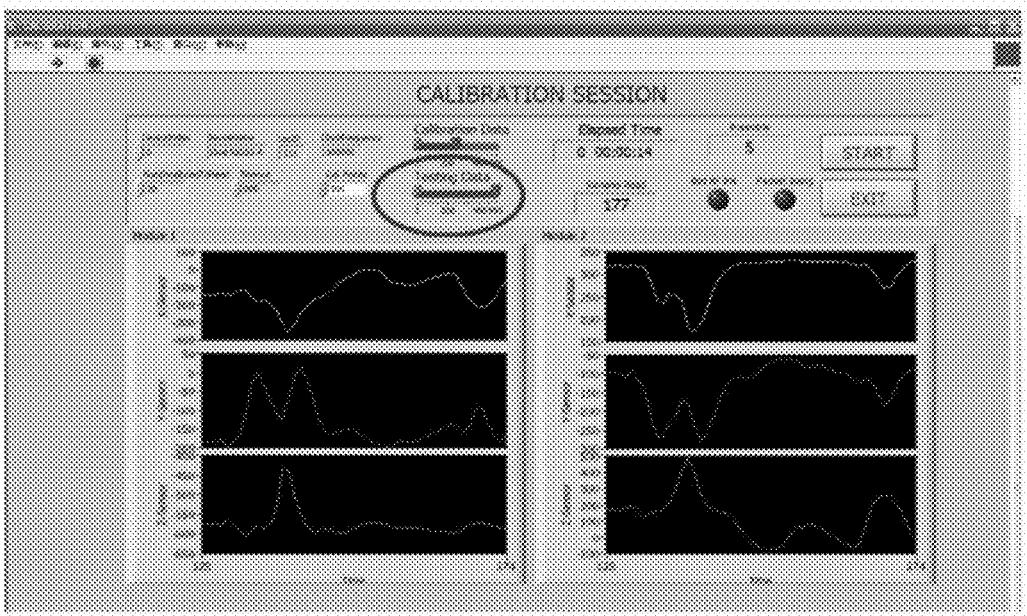
*Fig. 32*
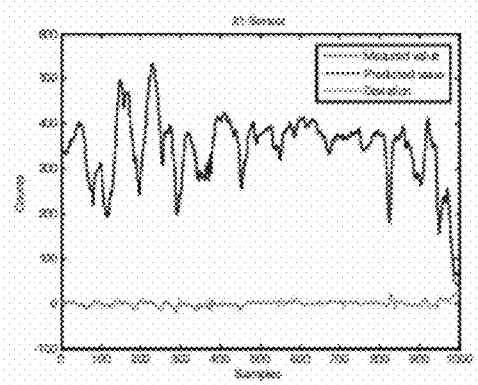 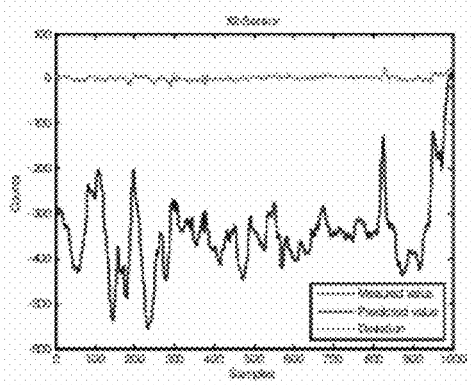
*Fig. 33A*        *Fig. 33B*

TONGUE OPERATED MAGNETIC SENSOR SYSTEMS AND METHODS

CROSS-REFERENCE TO RELATED APPLICATIONS

This application claims the benefit, under 35 U.S.C. §119(e), of U.S. Provisional Patent Application Ser. No. 61/057,053, filed 29 May 2008, the entire contents and substance of which is incorporated herein by reference in its entirety.

STATEMENT REGARDING FEDERALLY SPONSORED RESEARCH OR DEVELOPMENT

This invention was made with government support under grant IIS-0803184, awarded by the National Science Foundation[1]. The federal government has certain rights in the invention.

This invention was also made with support under grant GA1-0704-2 awarded by the Christopher and Dana Reeve Foundation.

BACKGROUND

Embodiments of the present invention relate to an apparatus for remote control of an appliance by systems and methods of using the apparatus. More particularly, embodiments of the present invention relate to an apparatus for remote control of an appliance by way of a tracer unit carried by the tongue of a subject and at least one sensor for detecting a position of the tracer, such that movements of the tongue by the subject affects control of an appliance.

Assistive technologies are important for people with severe disabilities to lead a self-supportive, independent life. Persons severely disabled as a result of causes ranging from traumatic brain and spinal cord injuries to stroke generally find it extremely difficult to carry out everyday tasks without continuous assistance. Assistive technologies that help them communicate their intentions and effectively control their environment, especially to operate a computer, can greatly improve the quality of life for this group of people and may even help them to be employed.

Several assistive technology devices are presently available that are controlled by switches. For example, the switch integrated hand splint, suck-n-blow (sip-n-puff) device, chin control system, and electromyography (EMG) switch are all switch-based systems and can provide the user with some limited degrees of freedom. A group of head-mounted assistive devices has been developed that emulate a computer mouse with head movements. Cursor movements in these devices are controlled by tracking an infrared beam emitted or reflected from a transmitter or reflector attached to the user's glasses, cap, or headband. Tilt sensors and video-based computer interfaces that can track a facial feature have also been implemented. A limitation of these devices is that only those people whose head movement is not inhibited can avail of the technology. Another limitation is that the subject's head should always be in positions within the range of the device sensors. For example, the controller may not be accessible when the subject is lying in bed or not sitting in front of a computer.

Another category of computer access systems used in assistive technologies operates by tracking eye movements from corneal reflections and pupil positions. Electro-oculographic (EOG) potential measurements have also been used for detecting eye movements. A limitation of these devices is that they affect the subject's eyesight by requiring extra eye movements that can interfere with the subject's normal visual activities, such as reading, writing, and watching.

Some available assistive devices can provide proportional control. Most of these devices, however, require some degree of physical ability such as foot movement, hand or finger movements, or head movement. The needs of persons with severe motor disabilities, such as those with amyotrophic lateral sclerosis (ALS) or middle to advanced locked-in syndrome, who cannot benefit from physical movements of any extremities can potentially be addressed by utilizing electric signals originated from brain waves or muscle twitches. Such brain computer interfaces (BCI), either invasive, or noninvasive have been the subjects of extensive research activities. For example, BRAINFINGERS™ (Brain Actuated Technologies, Inc., Dayton, Ohio, U.S.A.) is a non-invasive solution having a headband with three electrodes that sense and respond to surface electrical signals generated from forehead muscles, eye movements, and brainwave activities. THINK A MOVE™ (Think-A-Move, Ltd., Beachwood, Ohio, U.S.A.) is another interface platform, which utilizes the capabilities of the ear as an output device. BRAINGATE™ (Cyberkinetics Neurotechnology Systems, Inc., Foxborough, Mass., U.S.A.), on the other hand, is an example of an invasive technology using intracortical electrodes to record brain signals from the motor cortex area. These technologies rely on signal processing and complex computational algorithms, which can result in delays or significant costs. These technologies can also be susceptible to external noise and interferences. In addition, the subjects may not want to go through a brain surgery for the sake of regaining partial control over their environments.

Very few assistive technologies presently available have made a successful transition outside research laboratories and are widely utilized by severely disabled individuals. Financial, technical, and psychophysical factors affect the acceptance rate of assistive technologies. Among factors beneficial for adopting an assistive technology are the ease of usage and convenience in control. Operating the assistive device should desirably be easy to learn and require minimum effort on the subject's part. The device is desirably small, unobtrusive, low cost, and non- or minimally invasive. Finally, a factor that is often overlooked, but important to a subject with disability, is that the device is desirably cosmetically acceptable in a way that the user of the assistive technology does not look any different from able-bodied subjects. For example, most sip-n-puff users do not like this device, because it requires a large straw entering their mouth at all times which associate them with severe disability.

Therefore, there is presently an unmet need for assistive technologies for the disabled that provide some or even all of such features.

SUMMARY

Briefly describes, this summary lists several embodiments of the present invention, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In some embodiments of the present invention, an assistive system and apparatus for remote control of an appliance by a subject is provided. In some embodiments, the system and apparatus comprises a tracer unit adapted for non-obstructive affixation to the tongue of the subject, such that a change in position of the tongue changes the position of the tracer; at least one sensor for detecting a position of the tracer unit and adapted for non-obstructive placement proximal to the tracer unit; and a sensor control unit for transmitting a sensor signal to an appliance based on the detected position of the tracer unit.

In some embodiments, the tracer unit comprises a magnet, which in some embodiments can be a permanent magnet exhibiting straight-line normal demagnetization curve properties. In some embodiments, the magnet may comprise a flexible magnet, a rare earth magnet (e.g., a neodymium-iron-boron magnet or a samarium-cobalt magnet) or a ceramic magnet. In some embodiments, the apparatus comprises a post adapted for piercing the tongue to which the tracer unit is attached. In other embodiments, the tracer unit is adapted for affixation to the tongue by embedding the tracer unit within the tongue. In other embodiments, the tracer unit is adapted for affixation to the tongue by a tissue adhesive. In some embodiments, the tracer unit is encased within a biocompatible material (e.g., gold, platinum, a ceramic, a polymeric material, or combinations thereof).

In some embodiments, the at least one sensor is adapted for incorporation into a dental fixture fitted into the mouth of the subject. In other embodiments, at least one sensor is adapted for positioning outside the mouth of the subject. In some embodiments, at least one sensor is a plurality of sensors and the apparatus comprises power management circuitry for controlling power distribution to the plurality of sensors. In some embodiments, at least one sensor is a Hall-effect magnetic sensor, a magnetoinductive sensor, or a magnetoresistive sensor.

In some embodiments, the sensor control unit processes the sensor signal from an analog signal to a digital signal. In some embodiments, the sensor control unit comprises a wireless transmitter for transmitting the sensor signal by wireless communication.

In some embodiments, the appliance controlled by the system and apparatus is selected from the group consisting of a personal computer, a wheelchair, a bed, a telephone, a TV, a home appliance, a robotic system, an alternative and augmentative communication (AAC) device, and a speech synthesizer. In some embodiments, the appliance is a personal computer and the apparatus effects control of software on the personal computer that tracks movement, position, or both of the tongue.

In some embodiments, the users' own paralyzed limbs can be stimulated for the purpose of initiating a physical movement or for exercising the muscles under their control through a functional electrical stimulation (FES) system. In this embodiment, the users synchronize the stimulation of their muscles with the movements of their tongues.

In some embodiments, the system and apparatus comprises an appliance control unit for receiving the sensor signal from the sensor control unit, translating the sensor signal to a control signal, and transmitting the control signal to the appliance to thereby control of the appliance. In some embodiments, the appliance control unit receives the sensor signal by way of a receiver, which can be a wireless receiver. In some embodiments, the appliance comprises the appliance control unit and in other embodiments, the appliance control unit is separate from the appliance. In some embodiments, the appliance control unit is a smart device (e.g., a personal digital assistant, a mobile phone, a smart phone, or a personal computer).

In some embodiments, a method for remote control of an appliance by a subject is provided. The method comprises positioning in the mouth of a subject a tracer unit non-obstructively carried by the tongue, such that a change in position of the tongue changes position of the tracer unit; detecting the position of the tracer unit; generating a sensor signal based on the detected position of the tracer unit; and transmitting the sensor signal to an appliance, wherein the sensor signal effects control of the appliance. In some embodiments, an assistive apparatus disclosed herein is utilized for remote control of the appliance.

In some embodiments of the presently disclosed subject matter, a method for tracking movement, position, or both of a tongue in a subject is provided. In some embodiments, the method comprises providing in the mouth of a subject a tracer unit non-obstructively carried by the tongue such that a change in position of the tongue changes position of the tracer; detecting the position of the tracer unit; generating a signal based on the detected position and orientation (e.g., which direction it is pointing at) of the tracer unit; and analyzing the signal to thereby track movement, position, orientation (e.g. which direction the tip of the tongue is pointing) or all three of the tongue. In some embodiments, the method comprises transmitting the signal to a processing system, wherein the computer analyzes the signal. In some embodiments, the method comprises repeating each of the steps a desired number of times to track tongue movement, position, orientation or all three over a time period to generate a tongue movement pattern. Further, in some embodiments, the method comprises comparing the tongue movement pattern to a standard tongue movement pattern as part of a speech analysis program, a speech therapy program, or both. Further, in some embodiments, the method comprises series of rapid speech-based movements at a given location in the oral cavity, for example movement to the alveolar ridge for silent production of the following consonant-vowel combinations; /la/ /la/ /la/; /ta/ /ta/ /ta/, or on the basis of a sustained contact at a given location in the silent production of the continuant /n/ or fricative, /s/. In some embodiments of the method, an assistive apparatus disclosed herein is utilized for tracking movement, position, orientation or all three of the tongue.

In some embodiments, the sensor can be charged and powered by an inductive control system, wherein the need of batteries is reduced, or better yet, eliminated. In some embodiments, a calibration system and method for calibrating the sensor relative to the tracer unit is provided. In some embodiments, a system and method for training the sensor system for interpreting movements of the tongue is provided.

In some embodiments, the embodiments disclosed in the disclosures of U.S. Provisional Patent Application Ser. No. 60/731,731, filed 31 Oct. 2005; International Patent Application No. PCT/US06/042346, filed 31 Oct. 2006; and U.S. Ser. No. 12/084,227, filed 28 Apr. 2008 can be implemented in accordance with exemplary embodiments of the present invention, each of which are incorporated by reference as if fully set forth below.

These and other objects, features, and advantages of the electronic display system will become more apparent upon reading the following specification in conjunction with the accompanying drawing figures.

BRIEF DESCRIPTION OF THE DRAWINGS

FIG. 4 is a perspective view of an exemplary sensor useful in the present assistive apparatus, with exemplary dimensions and circuitry noted in the insert, in accordance with an exemplary embodiment of the present invention.

FIGS. 5A-5B are graphical representations of a series and including schematic drawings showing how lateral and distal movements of a magnetic tracer unit with respect to the surface of a Hall-effect sensor change the magnetic flux density and result in variations in the sensor output voltage, in accordance with an exemplary embodiment of the present invention.

FIGS. 11A-11C are perspective views of a recharging mouthpiece system, in accordance with an exemplary embodiment of the present invention.

FIG. 32 is a view of graphical user interface during a calibration of the sensor system, in accordance with an exemplary embodiment of the present invention.

FIG. 33A-33B are graphical representations of calibration results, in accordance with an exemplary embodiment of the present invention.

DETAILED DESCRIPTION

Figure 1:
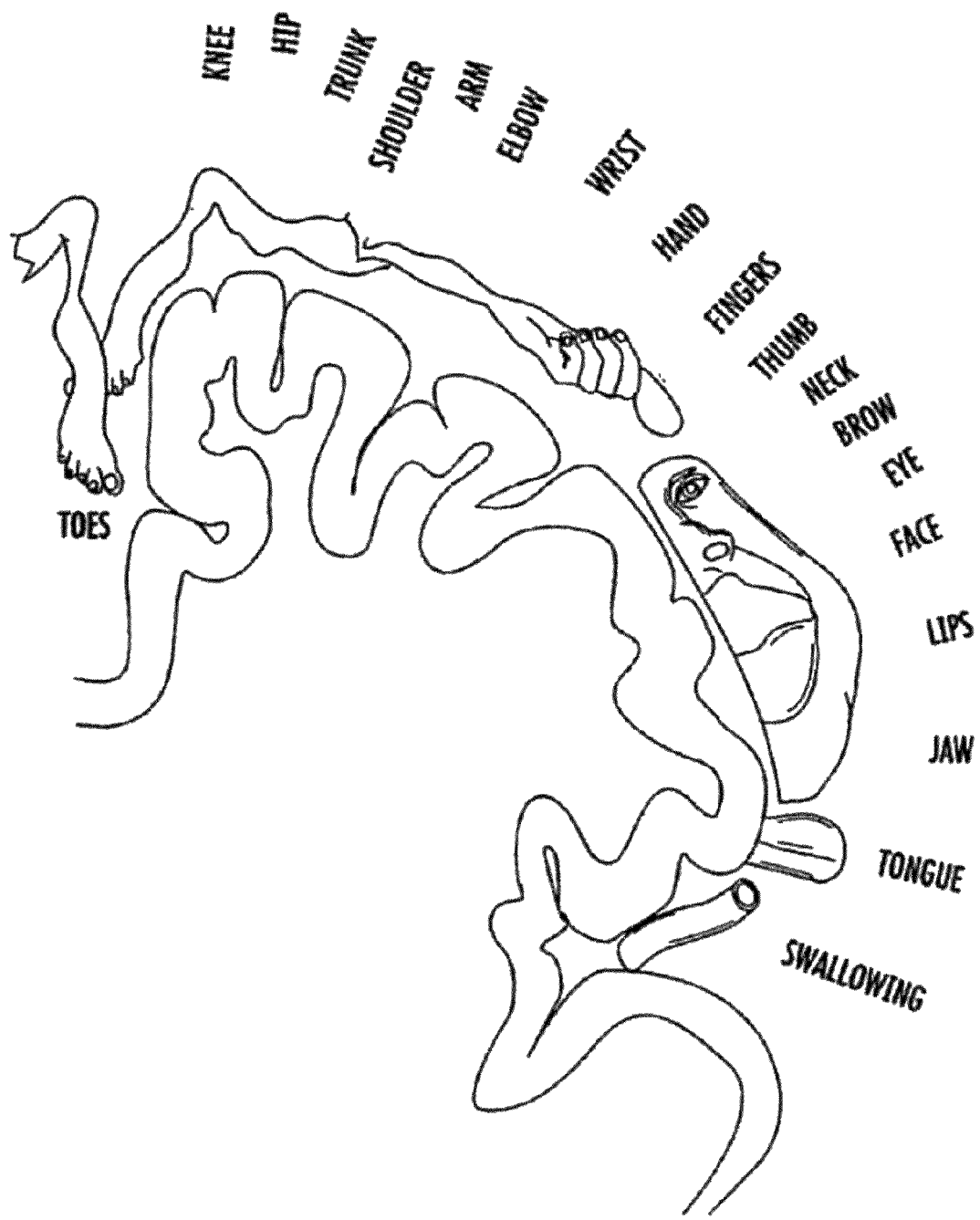
FIG. 1 is a motor homunculus drawing showing the proportional amount of brain motor cortex devoted to control of mouth, tongue, and other parts of the body.

To facilitate an understanding of embodiments, principles, and features of the present invention, they are explained hereinafter with reference to implementation in illustrative embodiments. They are described in the context of being a system and apparatus for controlling a device by way of a tracer unit carried by the tongue of a subject.

Embodiments of the present invention, however, are not limited to use in the described systems. Rather, embodiments of the present invention can be used when a system for remotely controlling a device or system is desired or needed. Thus, the system described hereinafter as an assistive technology for environment control can also find utility as a system for many applications beyond assistive technologies, including but not limited to gaming, scuba diving, deep subsurface operations, space exploration, military, and the like applications.

The components and features described hereinafter as making up the various embodiments are intended to be illustrative and not restrictive. Many suitable components and/or features that would perform the same or a similar function as the materials described herein are intended to be embraced within the scope of embodiments of the present invention.

Exemplary embodiments of the present disclosure relate to an oral, tongue controlled assistive apparatus for control of the environment by a subject. Methods for using the apparatus for control of the environment and for tracking tongue movement, position, and/or orientation are further provided.

The tongue can be considered an excellent appendage for operating an assistive technology apparatus, particularly with regard to severely disabled individuals, such as for example quadriplegics (sometimes known as tetraplegics), who have very little or no limb control. Additionally, the assistive apparatus can be useful for subjects involved in complex manipulations of the environment requiring full engagement of the limbs, such as for example pilots, soldiers, astronauts, and scuba divers, who can benefit from assistive technology to provide additional control of the environment. The assistive apparatus can also help the crew of agile combat aircrafts to control the plane or communicate with the command center under high gravity (high-G) physical stress, when effective limb functions or even speech is hindered by noise and other interferers in the environment. Further, the assistive apparatus can be of assistance to subjects who have a need to track and measure tongue movements and positioning, such as for example in subjects engaging in speech therapy, wherein there is a need to know tongue positioning during speech to aid in diagnosis and treatment of speech pathologies. In addition, the assistive apparatus can help people who are unable to talk, as a result of, among other things, tracheotomy, apraxia of speech, or ALS. The ability to make a few specific movements with their tongue can be interpreted by the apparatus software as specific words. These selected words can then be generated by a speech synthesizer. Currently these individuals, who might also be severely disabled, need to type what they want to say.

The apparatus can comprise a tracer unit that can be non-obstructively affixed to the tongue of the subject and at least one sensor, and in some embodiments an array of sensors, that can be positioned proximal to the tongue and tracer unit. "Non-obstructive" affixation of the tracer unit, as well as other components of the apparatus including but not limited to the at least one sensor, refers to placement of the component within or proximal to the mouth such that it does not substantially interfere with normal activities of the mouth, including but not limited to eating and speaking. "Non-obstructive" affixation or placement can also (but not necessarily) refer to affixation or placement of a component in a cosmetically acceptable (e.g., concealed) manner.

The sensor(s) measures the location, orientation, and/or changes in location of the tracer unit, which moves according to positioning of the tongue. "Proximal", with reference to the positioning of the sensor, refers to a distance sufficiently close to the tracer unit to detect a position (e.g., location, orientation, and/or change in position and/or orientation) of the tracer unit, such as for example outside of the mouth affixed on or near the face or within the mouth attached, for example on the outside of the teeth so as to be non-obstructive. Thus, proximal positioning of the sensor(s) depends on the sensitivity of the sensors as well as the detectability of the tracer unit and is within the capabilities of one of skilled in the art to determine without undue experimentation. The sensor processes the tracer unit positioning into sensor signals, which can be digitized and transmitted to an external appliance control unit, such as for example a "smart device" (e.g., a personal digital assistant (PDA) or smartphone), which then effects control of a desired appliance. In some embodiments, the smart device is a wireless smart device for wireless communication with the sensors and/or appliances controlled.

The sensor data related to tracer unit positioning can be processed and combined to determine the position and motion of the tongue relative to the sensors. This information is then used to control an appliance. Movement of the tongue while utilizing the assistive device can be used to operate, for example, a wheelchair, a computer, a phone, home appliances, or other equipment(s). In one embodiment, the apparatus comprises a wireless integrated mouthpiece transmitting tongue location data based on positioning of a tracer unit affixed to the tongue to a compact portable appliance control unit, such as a wireless smart device (e.g., a pocket computer, a personal digital assistant, or a mobile phone). The appliance control unit can then connect the subject to appliances and/or local and global environments through, for example a wireless local area network (WLAN) and the Internet, respectively.

In an exemplary embodiment, one or a few sensors can capture a large variety of tongue movements by processing individual or a combination of sensor outputs. A set of movements can be tailored for each individual user and mapped onto a set of customized functions for environment control. Further, the apparatus can provide the advantage of proportional control of the environment, which allows for a smooth and natural control over the environment compared to other devices that are mostly based on on/off switches or having a limited number of states. Fewer sensors translate to an unobtrusive device with lower power requirements. Moreover, the sensors can be activated or deactivated by a passive tracer component in the form of a permanent magnet leading to additional power savings. Another advantage over alternative technologies is that the system is largely immune to signal noise, interference, and involuntary body movements that might affect normal operation of other devices.

Referring now to the drawings, wherein like reference numerals represent like parts throughout the views, embodiments of the present invention can be described in detail. Embodiments of the present invention relate to a system for remotely controlling a device on a user's tongue.

As shown in FIG. 1, a motor homunculus illustrates that the tongue and the mouth occupy an amount of sensory and motor cortex that rivals that of the fingers and the hand. Unlike the eyes, which have rich cortical representations but have been evolved as sensory organs, the mouth and the tongue have evolved as motor and manipulation organs. Thus, they are inherently capable of performing sophisticated motor control and manipulation tasks, which are evident in their usefulness in vocalization and ingestion.

The tongue is connected to the brain by a cranial nerve (i.e., the hypoglossal nerve), which generally escapes severe damage in spinal cord injuries. It is also one of the last appendages to be affected in most neuromuscular degenerative disorders. These observations along with the fact that the tongue can move very fast and accurately within the mouth cavity with many degrees of freedom, point to potential of using the tongue as an organ for manipulating assistive devices. Furthermore, the tongue muscle is similar to the heart muscle in that it does not fatigue easily. The tongue muscle is not afflicted by repetitive motion disorders that can arise when a few exoskeletal muscles and tendons are regularly used. Therefore, unlike head pointing and related technologies requiring motion of other body parts, a tongue operated device can have a very low rate of perceived exertion and can be used over a long period of time.

Unlike EOG or EMG based systems that require attachment of surface electrodes to the user's face, an oral device involving the tongue is mostly hidden from sight. Accordingly, it is cosmetically inconspicuous and offers a degree of privacy for the user. The tongue is not influenced by the posture and position of the rest of the body. Therefore, unlike many other assistive devices, which lock the patient in front of a computer monitor or in a wheelchair to be able to use the device, an oral device involving the tongue can be used in many positions or postures, especially, for example, if it is wireless. The tongue can function during random or involuntary neurological activities such as muscular spasms. Therefore, tongue-operated assistive devices are less prone to involuntary movements, which can affect other devices, especially those based on EMG, EEG, or EOG signals. Tongue movements are natural and do not require as much thinking or concentration. Therefore, tongue-operated assistive devices potentially can be easy to learn and use. When a disabled individual uses a computer, which is one application of assistive and environment control technologies, the individual directly uses his/her eyes and brain at all times. It is less likely, however, for the individual to require use of their tongue, for example by talking or eating at the same time. Therefore, using the tongue in an assistive device can require minimum effort and cause minimum interference with other activities that an individual is involved in when using an oral assistive device. Furthermore, unlike neural signals from the motor cortex, noninvasive access to tongue movements is readily available.

A few tongue-operated assistive technologies have been developed to date. However, despite all the advantages noted above, these devices have not been widely used by disabled individuals for several reasons.

For example, TONGUE TOUCH KEYPAD (UK; NewAbilities Systems Inc., Santa Clara, Calif.) includes a keypad fitted in the roof of the mouth with nine sensors that are activated by the touch of the users tongue. The sensors emit radio waves to a control box mounted on the person's wheelchair, bed, or other furniture, which operates a computer or other equipment in the environment. The TTK system is limited as being switch-based (rather than continuous proportional control), bulky, and obtrusive. It cannot offer proportional control or large degrees of freedom.

Another example is TONGUE POINT (International Business Machines, Armonk, N.Y.), which is based on the IBM TRACKPOINT® pointing device. The pointing device is a pressure sensitive small isometric joystick for use inside the mouth. Although this device provides proportional control, it is restricted to a joystick operation and many selections or button click operations are performed through an additional external switch or a bite switch. The tip of the joystick may protrude about one centimeter into the mouth, which can interfere with a user's talking and eating functions. This device can also prove to be uncomfortable for long-term use.

The TONGUE-MOUSE has a sensor module incorporating piezoelectric ceramic sensors and conductive adhesives to connect the sensors to the electronics. The sensors form a matrix, the elements of which can detect strength and position of touch by the tongue. The sensor module is fitted within the oral cavity as a conventional dental plate and the user should hold the plate between his/her front teeth. The sensor module plate is rather large and prevents the user from eating or talking while using this device.

The presently disclosed assistive system and apparatus also involves the tongue as the controlling appendage. The presently disclosed apparatus, however, addresses deficiencies of other oral assistive devices in that it can have one or more of the following characteristics: small, unobtrusive, low cost, non- or minimally invasive, and cosmetically acceptable for the subject using the device. In particular, the present apparatus provides for tracing the motion of the tongue by sensors positioned proximal to the tongue using a tracer unit affixed to the tongue. The detected tongue motion can then be converted to control signals for controlling appliances within the subject's environment.

The following terms are defined as follows herein:

"Appliance", as used herein, refers to an instrument or device designed for a particular or general use or function. An appliance can be, but is not limited to a personal computer, a powered wheelchair, a motorized bed, a telephone, a home appliance, and a speech synthesizer.

"Magnetic field strength" (H, Units: Oersted) (also known as magnetizing or demagnetizing force), refers to the measure of the vector magnetic quantity that determines the ability of an electric current, or a magnetic body, to induce a magnetic field at a given point.

"Magnetic induction" (B, Units: Gauss) refers to the magnetic field induced by a field strength, H, at a given point. It is the vector sum (at each point within the substance) of the magnetic field strength and resultant intrinsic induction. Magnetic induction is the flux per unit area normal to the direction of the magnetic path. Therefore, it is also called magnetic flux density.

"Hysteresis loop" refers to a closed curve obtained for a material by plotting (usually in rectangular coordinates) corresponding values of magnetic induction, B, for ordinate and magnetizing force, H, for abscissa when the material is passing through a complete cycle between definite limits of either magnetizing force, H, or magnetic induction, B.

A "demagnetization curve" is the second (or fourth) quadrant of a major hysteresis loop. Points on this curve are designated by the coordinates $B_d$ (remnant induction) and $H_d$ (remnant field).

"Remnant induction" ($B_d$, Units: Gauss) refers to any magnetic induction that remains in a magnetic material after removal of an applied saturating magnetic field, $H_s$. ($B_d$ is the magnetic induction at any point on the demagnetization curve).

"Remnant field" ($H_d$, Units: Oersteds) refers to the value of H corresponding to the remnant induction, $B_d$ on the demagnetization curve.

"Energy product" ($B_d H_d$, Units: Megagauss-Oersteds (MGOe)) refers to the energy that a magnetic material can supply to an external magnetic circuit when operating at any point on its demagnetization curve.

As used herein, "remote control", as in the "remote control of an appliance", refers to control of an object indirectly by way of an intermediary without direct control by the actor on the object. For example, "remote control" can encompass the control of an appliance by a subject via an assistive apparatus disclosed herein, wherein tongue movements and positioning are translated to command signals by the apparatus and issued to the appliance. "Remote control" is inclusive of both wired and wireless communication between the actor, the intermediary, and/or the object controlled.

As used herein, the term "smart device" refers to a device with processing capabilities. A smart device can have on-board memory or other storage capacity, can be written to as well as read from, and can contain one or more applications that perform a particular function. Some smart devices can contain an operating system. Exemplary smart devices include, but are not limited to personal computers, PDAs and mobile telephones. Some smart devices communicate wirelessly and can be referred to herein as wireless smart devices.

As used herein, the term "wireless smart device" refers to a smart device that can communicate via an electric and/or magnetic field between the smart device and some other entity, such as for example an appliance and/or a sensor control unit. One type of wireless communications that can be used between a wireless smart device and reader is near field communications. Near field communications typically occur at a distance of within about one wavelength of the communications frequency being used between the wireless smart device and the receiving and/or communicating unit. A wireless smart device can communicate with a device via inductive coupling of the other device antenna to the smart device antenna. The two loop antennas effectively form a transformer. The reader amplitude-modulates the RF field to send information between the devices. The smart device communicates with other devices, including other smart devices, by modulating the loading on the smart device antenna, which also modulates the load on the other device antenna. Longer range wireless communication techniques for use by wireless devices which include, but are not limited to, BLUETOOTH®, optical, and infrared.

The presently disclosed subject matter provides an assistive apparatus for remote control of an appliance by a subject. In some embodiments, the subject can be a human subject in need of an assistive device for manipulating their environment, such as disabled individuals, including for example quadriplegic (or tetraplegic) subjects and those with spinal cord injuries (SCI). In some embodiments, the subject is in need of controlling a complex appliance, or is functioning in a difficult environment that limits his/her movements and needs to utilize the assistive device to control the appliance or function in the environment. For example, the subject in some embodiments can be a pilot, astronaut, scuba diver, or soldier.

In some embodiments, the assistive apparatus comprises: (a) a tracer unit that can be non-obstructively affixed to the tongue of the subject such that a change in position of the tongue changes position of the tracer unit; and (b) at least one sensor for detecting a position of the tracer unit and adapted for non-obstructive placement proximal to the tracer unit. The apparatus can further comprise a sensor control unit for transmitting sensor signals from the sensor(s) to the appliance or appliances to be controlled based on the detected position of the tracer unit. In some embodiments, the sensor control unit processes the sensor signals and transmits them directly to the appliance as control signals to effect control of the appliance. In other embodiments, the apparatus can comprise an appliance control unit that can be physically separated from, but in communication with, the sensor control unit. In these embodiments, the appliance control unit receives the sensor signals and processes the sensor signals to control signals, which are then transmitted to the appliance to effect control of the appliance. In some embodiments, the appliance control unit can be integrated into the appliance. In other embodiments, the appliance control unit is a separate device in communication with the appliance.

The signals received from the sensor control unit by the appliance control unit can be demodulated and demultiplexed to extract the individual sensor outputs. By processing these outputs, the motion of the tracer unit and consequently the tongue within the oral cavity is determined. Assigning a certain control function to each particular tongue movement can be done in software and can be customized for each individual user. These customized control functions can then be used to control (e.g., operate) the appliance or appliances.

In some embodiments of the assistive apparatus, the tracer unit comprises a magnet and the motion of the tongue is traced by an array of magnetic sensors, which measure the magnetic field generated by the magnet. The tracer unit can comprise a magnet contained within a nonmagnetic fixture and affixed to the tongue. The magnetic sensors can be positioned proximal the tracer unit, and in some embodiments can be mounted on a dental retainer and attached on the outside of the teeth to measure the magnetic field from different angles and provide continuous real-time analog outputs. In other embodiments, the sensors are positioned outside the mouth, but in close proximity to the magnetic tracer unit, such as for example affixed on support structures attached to the head of the subject (e.g., similar to headphones) that position the one or more sensors at desired locations near the tracer unit (e.g., on or near left and/or right cheeks of the subject). The maximum distance for proximal placement of the magnetic sensors relative to the tracer unit can be dependent upon both the strength of the magnet and the sensitivity of the magnetic sensors. For example, a larger magnet can generate a larger magnetic field and will permit for further distance from the magnet to achieve proximal placement of the magnetic sensor. At some point, however, the magnet size may become too large to be non-obstructively affixed to the tongue as a tracer unit. Likewise, a sensor can be chosen based on increased sensitivity if a further proximal placement distance is desired. Depending on the sensitivity of the sensor and the magnetic field strength of the magnet, in some embodiments, proximal placement of the sensor with reference to the tracer unit can be less than about 20 cm, in some embodiments less than about 15 cm, in some embodiments less than about 10 cm, in some embodiments less than about 5 cm, and in some embodiments less than about 2 cm.

The signals from the magnetic sensors can be linear functions of the magnetic field, which can be a continuous position-dependent property, and which can provide for continuous proportional control of an appliance. Thus, a few magnetic sensors are able to capture an unlimited number of tongue positions and movements. These sensors can provide a tremendous advantage over switch-based (digital) on/off devices in that the user can communicate with the environment much faster, smoother, and more naturally using options of proportional, fuzzy, and/or adaptive control over the environment. In real life, control of the environment occurs via an analog regime. Thus, a few representative sensors utilized by the present apparatus are able to capture a wide variety of tongue movements, which provides advantages over switch-based devices. For example, other assistive technologies that emulate a computer mouse use an additional input device such as a switch for the mouse button clicks besides the primary method for moving the pointer. In the presently disclosed subject matter on the other hand, the additional switches are unnecessary since a specific tongue movement can be assigned to the button press.

Figure 2:
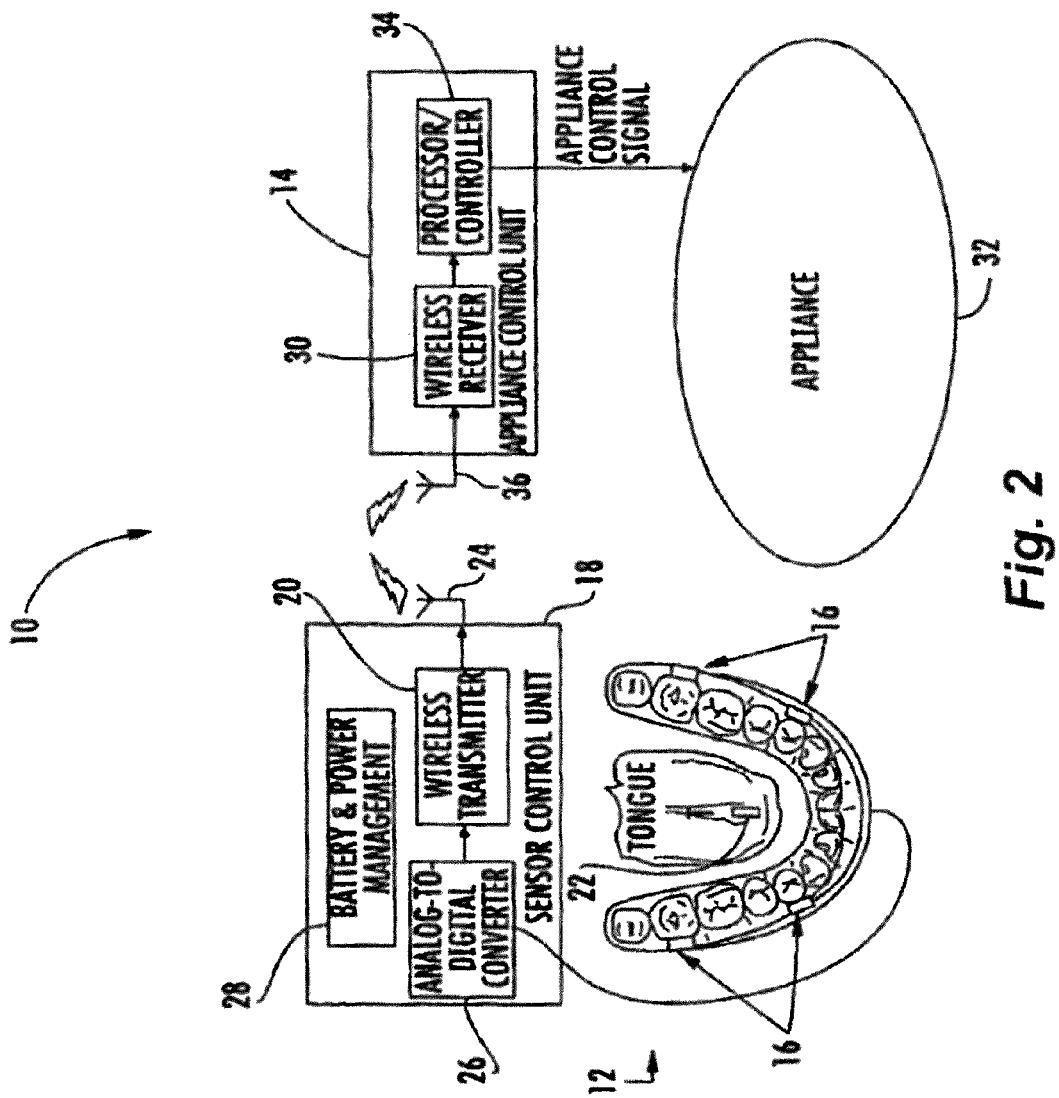
FIG. 2 is a schematic drawing of an assistive system showing interaction of the various components with each other and an appliance to be controlled, in accordance with an exemplary embodiment of the present invention.

FIG. 2 is a schematic diagram showing one embodiment of an assistive system and apparatus 10 (referred to herein as the "apparatus") disclosed herein comprising two components: one inside the mouth, a mouthpiece 12, and the other outside the mouth, an appliance control unit 14, which can in some embodiments be portable. The mouthpiece 12 can include sensors 16 and a sensor control unit 18. The mouthpiece 12 electronics can be integrated on an application specific integrated circuit (ASIC). The sensor control unit 18 comprising the ASIC along with a wireless transmitter 20 can be incorporated into a miniaturized package that can be fitted under the tongue or attached to the outer surface of the teeth as part of a dental retainer, as shown in FIGS. 3A-3B.

Figure 38:
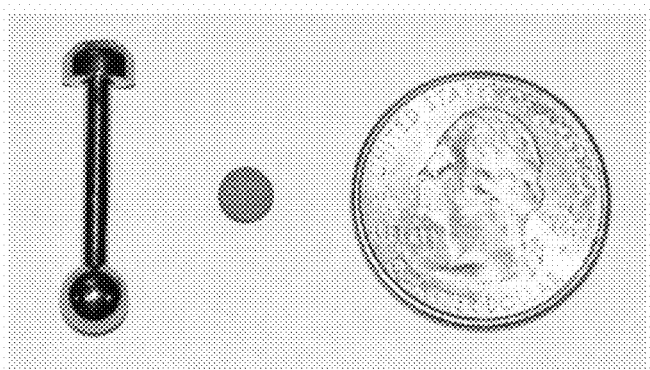
FIG. 38 shows a top view of a magnetic tongue stud placed next to a magnetic tracer and a quarter, in accordance with an exemplary embodiment of the present invention.
Figure 39A:
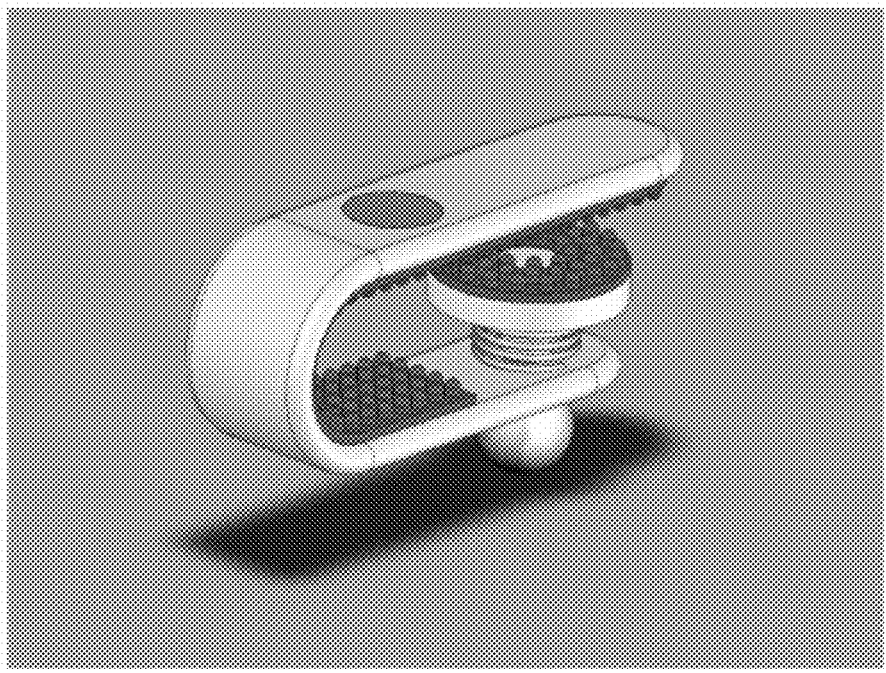
FIGS. 39A-39B show perspective views of a magnetic tongue clip, in accordance with an exemplary embodiment of the present invention.
Figure 39B:
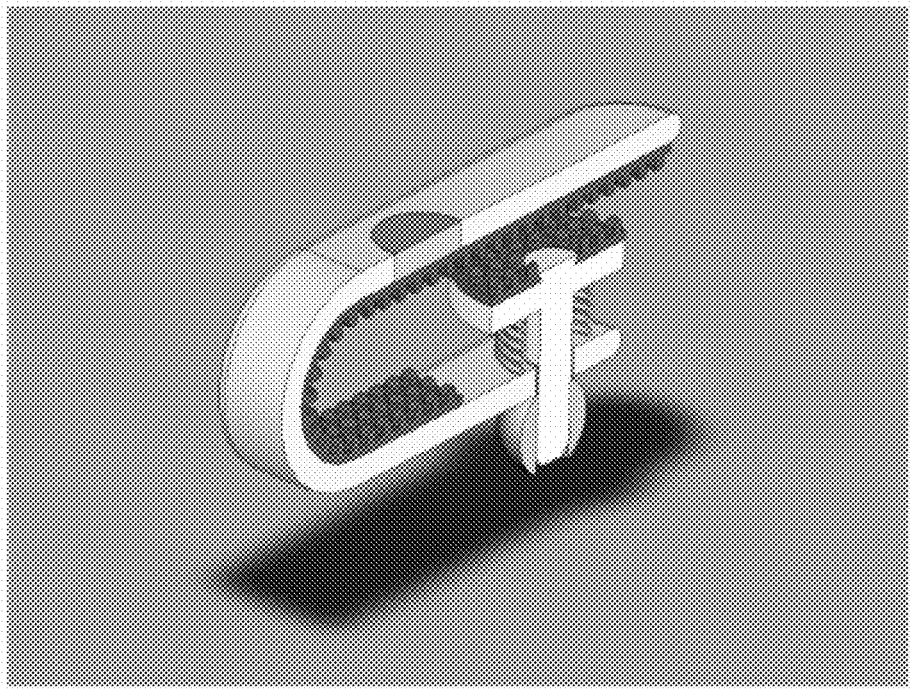

A tracer unit 22, such as for example a magnet, can be coated with a non-magnetic biocompatible material, such as gold, platinum, or a polymer, and affixed to the tongue T. In some embodiments, the tracer unit is adapted for affixation to the tongue by using a magnetic tongue clip as shown in FIG. 38. FIG. 38 shows a top view of a magnetic tongue stud placed next to a magnetic tracer and a U.S. quarter coin, while FIGS. 39A-39B show perspective views of a magnetic tongue clip. Due to the proximity of tracer unit 22 and sensors 16 in the oral cavity, the apparatus 10 can be more robust with regard to noise, interference, and involuntary movements compared to alternative technologies. Many aspects of the apparatus can be customized and fine tuned through software for a particular individual's oral anatomy, requirements, and disabilities. Therefore, the apparatus 10 can serve as a platform to address a variety of needs of different individuals.

Figure 3B:
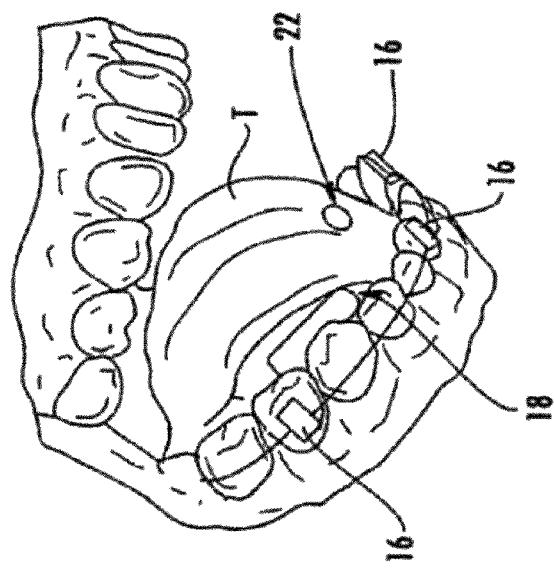
FIG. 3B is a side perspective view of a model of a mouth showing exemplary placement of a tracer unit, sensors and sensor control unit within the mouth, in accordance with an exemplary embodiment of the present invention.
Figure 3A:
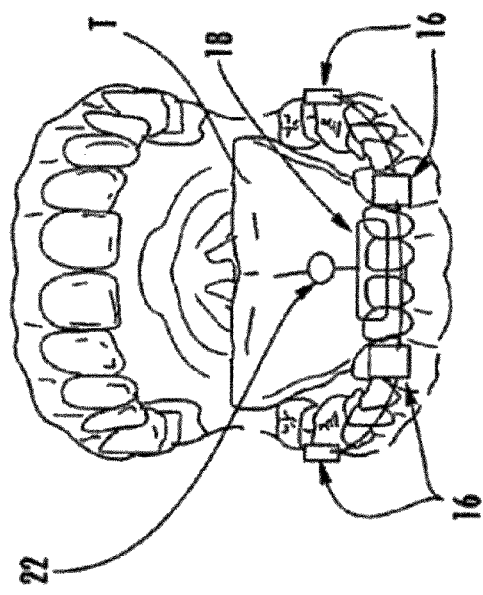
FIG. 3A is a front view of a model of a mouth showing exemplary placement of a tracer unit, sensors, and a sensor control unit within the mouth, in accordance with an exemplary embodiment of the present invention.

As noted, the apparatus 10 can comprise of a mouthpiece unit 12, which can be located inside the oral cavity, as shown for example in FIGS. 3A-3B, and an external appliance control unit 14 that can be located within the subject's surrounding environment and which is in communication, for example by wired or wireless communication, with the mouthpiece 12. With reference to FIG. 2, the mouthpiece 12 and the appliance control unit 14 can comprise the following components.

The components that can be positioned within the mouth include a tracer unit 22 and the mouthpiece 12. The mouthpiece 12 can comprise sensors 16 arranged in a coordinated array within the mouth; a wireless transmitter 20, which can comprise a miniature antenna 24; an analog to digital converter (ADC); and power management circuitry 28, which can include a battery.

The tracer unit 22 can, in some embodiments, comprise a magnet, which can be contained within a biocompatible non-ferromagnetic fixture (e.g., gold, platinum, a polymeric material, or combinations thereof) that is non-obstructively affixed to tongue T, as shown in FIGS. 2 and 3A-3B. "Affixed to the tongue" as used herein refers to secured to the tongue such that tracer unit 22 is not easily dislodged from the tongue and tracks tongue movement accurately. That is, the tracer unit 22 is secured tightly enough to tongue T such that fine movements of tongue T are not lost to the sensors 16 due to wobble or other unnecessary motion of the tracer unit 22. For example, the tracer unit 22 can be mounted on a post, an example of which is illustrated in FIG. 38, that is pierced through the tongue or tracer unit 22 can be embedded within the tongue T. Instead of pierced or implanted tracer units 22, a subject can have small tracer units 22 attached to their tongue T by small plastic clips, as exemplarily shown in FIGS. 39A-39B or with elastic bands. It is also possible to temporarily attach the tracer to the subject's tongue using a waterproof biocompatible tissue adhesive such as Dermabond® (Johnson & Johnson, New Brunswick, N.J.) or Cyanodent® (Ellman International Inc., Oceanside, N.Y.). In essence, the tongue T can carry the tracer unit 22 as it moves.

The magnet can in some embodiments be a permanent magnet exhibiting straight-line normal demagnetization curve properties. The magnet generates a magnetic field inside the mouth and outside proximal to the face that changes with tongue movements, and thus provides real time information about the tongue position and orientation (i.e., direction) with respect to the lower or upper jaw coordinates (the sensor 16 locations). A permanent magnet that generates the magnetic field can be a small, passive, and inherently wireless component leading to user convenience and requiring no power source or replacement. That is, the sensors 16 can be magnetic sensors and can be activated by a permanent magnet. The system power requirement can be limited to the sensors and the wireless link over a short range (e.g., 2 meters), which can be designed to be low power by time-division-multiplexing (TDM), i.e., turning only one sensor on at any particular time, and other circuit design techniques, as disclosed herein. Therefore, the battery size can be small and its lifetime sufficiently long to reduce burden on the subject.

In some embodiments, the magnet can be a flexible magnet, a rare earth magnet or a ceramic magnet. Exemplary rare earth magnets useful for incorporation within the tracer unit 22 include but are not limited to neodymium iron-boron (NdFeB) magnets and samarium-cobalt (SmCo) magnets. Table I lists properties of several exemplary magnets suitable for use with the presently disclosed subject matter.

TABLE I

Characteristics of Materials Used in Permanent Magnets

| Material | $B_r$ (Gauss) | $H_c$ (Oersteds) | $BH_{max}$ (MGOe) |
|---|---|---|---|
| Flexible | 1,725 | 1,325 | 0.6 |
| Ceramic 1 | 2,200 | 1,900 | 1.1 |
| Ceramic 5 | 3,950 | 2,400 | 3.6 |
| SmCo 18 | 8,600 | 7,200 | 18 |
| SmCo 26 | 10,500 | 9,200 | 26 |
| NdFeB 35 | 12,300 | 11,300 | 35 |
| NdFeB 41 | 13,050 | 12,500 | 41 |
| NdFeB 42 | 13,200 | 12,500 | 42 |
| NdFeB 43 | 13,300 | 12,500 | 43 |
| NdFeB 45 | 13,700 | 12,500 | 45 |
| NdFeB 48 | 14,200 | 12,500 | 48 |
| NdFeB 50 | 14,500 | 12,500 | 50 |
| NdFeB 52 | 14,800 | 12,500 | 52 |

Still referring to FIG. 2, the sensor 16 can in some embodiments comprise an array of sensors. In some embodiments, sensors 16 are magnetic sensors, such as, for example, Hall-effect sensors, magnetoinductive sensors (e.g., MICROMAG™ from PNI Corporation, Santa Rosa, Calif.) and/or magnetoresistive sensors (e.g., serial numbers HMC1303, HMC1512, and HMC6052 available from Honeywell International, Inc., Plymouth, Minn.) when the tracer unit 22 comprises a magnet. Magnetic sensors, which are available in various sizes, such as about $3 \times 2 \times 0.75$ mm$^3$ (see, e.g., FIG. 4 illustrating Allegro A1391 (Allegro Microsystems, Inc., Worcester, Mass.) micropower 3 V linear Hall-effect sensor with tri-state output and user selectability), can be incorporated in a dental fixture and mounted on posts attached to the outside of the upper and/or lower teeth in the form of an orthodontic brace. Alternatively, soft form-fitting plastic dental fixtures can be used to conform to each subject's oral anatomy, while holding the sensors. The sensors 16 can be stationary with respect to the jaw coordinates and gather information about movements and orientation of the permanent magnet that is attached to the tongue as the tracer unit 22. The sensors 16 convert the magnetic field intensity (B) from the magnet to a proportional analog output voltage. For example, linear Hall-effect sensors convert the magnetic flux density that is vertical to their surface to a proportional voltage, which can be measured as a continuous real-time analog signal output. Therefore, they respond to lateral, distal, and rotational movements of a magnetic tracer unit 22, as depicted in FIGS. 5A-5B.

Power management circuitry 28 can be linked with a battery and provide for control of power distribution to sensors 16. A small battery such as a button cell can provide sufficient power to mouthpiece 12 components for a long duration, for example up to several weeks. Power management circuitry 28 scans through sensors 16 at a predefined rate and turns them on one at a time to save power. In an exemplary embodiment, a single sensor 16 draws power at any time in order to reduce power consumption.

In an exemplary embodiment, the battery can be a rechargeable battery that can be charged by a wired or a wireless system. Wired charging of a battery is well known in the art and is as simple as connecting the battery (or its module/apparatus) to a power providing outlet. Over time, the battery charges and then can be reused upon charging.

As for wireless charging, as illustrated in FIGS. 11A-11C, a power charging station 1100 can be provided to interact with the power management circuitry 1210 of a mouthpiece 1200 illustrated in FIGS. 12A-12D in order to charge the built-in rechargeable batteries 1215, 1220 of the mouthpiece 1200. As mentioned herein, in some embodiments, the sensor system of apparatus 10 can comprise the mouthpiece 1200. In addition to the features and/or elements of the mouthpiece 1200, it can further include at least one rechargeable battery 1215, 1220. In some embodiments, the mouthpiece 1200 can include a secondary coil 1205 for interacting with a primary coil 1110 of the recharging unit 1100, shown in FIGS. 11A-11C.

In some embodiments, the mouthpiece 1200 can include the sensors 1201, one or more rechargeable batteries 1215, 1220, and a secondary coil 1205. Over time, and specifically when operating, the sensors can drain the power of the rechargeable battery 1215, 1220). To recharge the battery, the mouthpiece 1200 can be placed in proximity to a charging station 1100, as shown in FIGS. 11A-11C. In some embodiments, the mouthpiece can be inserted into a charging container 1105 of the charging station 1100. The primary coil(s) 1110 of the charging station 1100 can inductively couple onto the secondary coil(s) 1205 of the mouthpiece 1200 in order to charge the mouthpiece batteries 1215, 1220. Exemplarily, the primary coils 1110 can emit a magnetic field to induce power to be wirelessly transmitted and received by the secondary coil 1205. The rechargeable battery 1215, 1220 receives the magnetic field and stores power for later usage. In an exemplary embodiment, the mouthpiece 1200 can be hermetically sealed in a package 1225.

Users can operate the present system throughout the day without the need for recharging the battery 1215, 1220. At night, before going to sleep, when users no longer need to control their environments, they can remove/have removed the mouthpiece 1200 from their mouth either by themselves or with the help of a caregiver and place it in proximity to the power charging station 1100, for example within its container 1105. The batteries 1215, 1220 fully recharge over night and the next they, the mouthpiece 1200 will be ready for use. In an exemplary embodiment, the charging container 1105 can be water resistant, such that it can be filled with antiseptic fluid such as mouthwash to sterilize the mouthpiece 1200 and keep it fresh to be used the next day.

Referring back to FIG. 2, the sensor control unit 18 can process sensor signals from an analog signal to a digital signal. For example, the sensor control unit 18 can include an analog to digital converter (ADC) 26, which can be equipped with a multiplexer that has as many input channels as the number of magnetic sensors 16 in the array, and can take one or multiple samples from the analog output of sensor 16, which is turned on by power management circuitry 28. This results in a time division multiplexed (TDM) series of samples, which are then converted to a serial data bit stream by ADC 26 before being transmitted across, for example a wired or wireless link to appliance control unit 14. In an exemplary embodiment, the serial data bit stream is stored in an intermediate temporary first-in-first-out (FIFO) buffer to be transmitted at a high rate when the buffer is full. The communication link (e.g., via the wireless transmitter 20 and the antenna 24) can be faster than the sampling rate required for this application. Therefore, the intermediate buffer can result in power saving by reducing the duty cycle of transmitter 20.

Continuing with reference to FIG. 2, a transmitter unit such as wireless transmitter 20, can be incorporated into sensor control unit 18 along with the digitization blocks (e.g., ADC 26) and power management blocks (e.g., power management circuitry 28), and modulates the buffered serial data into a wireless signal, such as for example an RF signal and transmits it to an external receiver. In an exemplary embodiment, the transmitter operates in the industrial-scientific-medical (ISM) band.

Figure 12A:
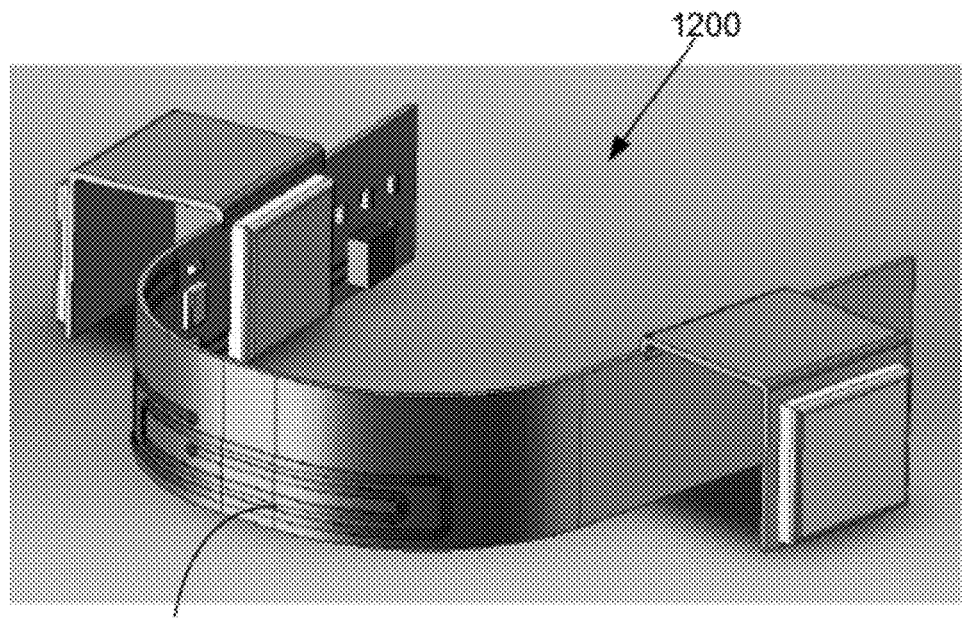
FIGS. 12A-12D are perspective views of a mouthpiece adapted to be recharged, in accordance with an exemplary embodiment of the present invention.
Figure 12B:
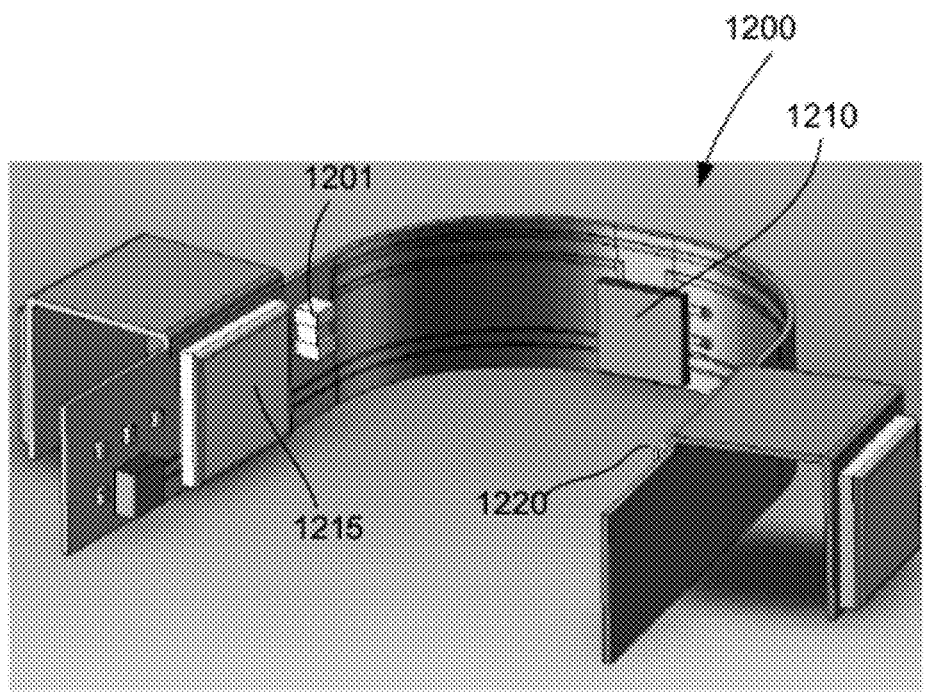
Figure 12C:
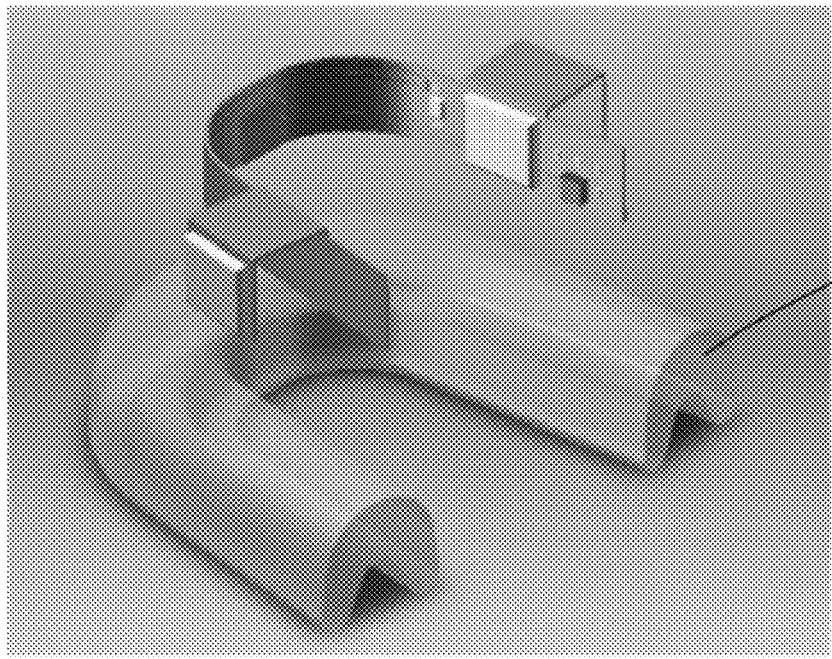
Figure 12D:
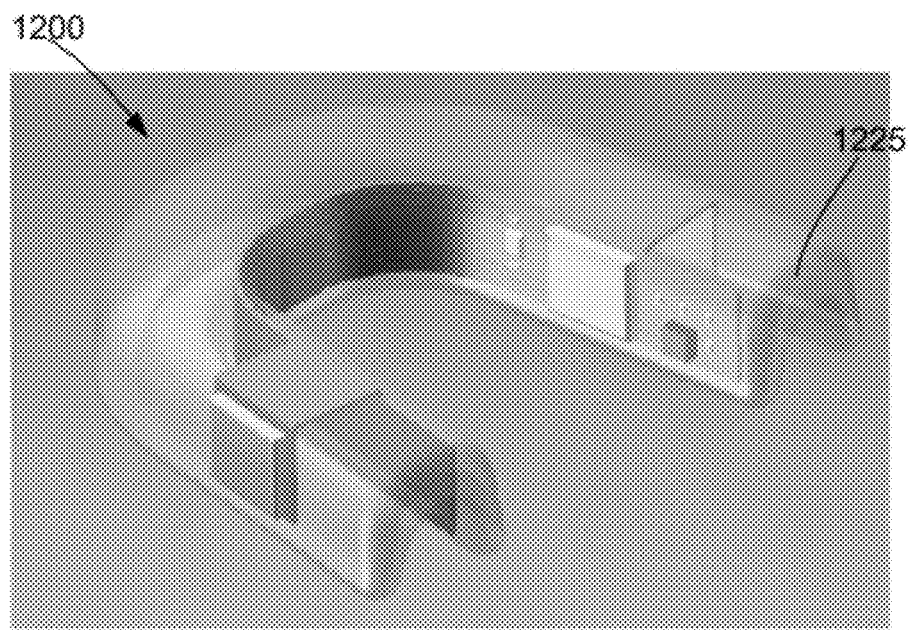

FIG. 2 further illustrates that a wireless transmitter 20 can comprise antenna 24, which can be designed for the transmitter specific operating frequency (carrier frequency). The antenna 24, which can improve the range of the transmitted signal, can also be incorporated into sensor control unit 18, along with the wireless transmitter 20, the ADC 26, and the power management circuitry 28. The sensor control unit 18 can be mechanically supported by a dental fixture and electrically connected to sensors 16. In an embodiment illustrated in FIGS. 3A-3B, the sensor control unit 18 can be located below tongue T, such that it does not interfere with the biological tongue functions in speech and food ingestion. In another embodiment of the present system, the sensor control unit 18 can be distributed on the mouthpiece along the outer or inner surface of the teeth, as shown in FIGS. 12A and 12B.

The appliance control unit 14 can receive a sensor signal from sensor control unit 18 by way of a receiver, which can be in some embodiments and as shown in FIG. 2, a wireless receiver 30. The wireless receiver 30 can detect, demodulate, demultiplex, and decode different channels of the sensor control unit 18 outputs. In some embodiments, the sensor control unit 18 can process the sensor signal to a command signal for communication to an appliance 32, either directly or by way of appliance control unit 14. In other embodiments, and as shown in FIG. 2, the appliance control unit 14 can comprise a processor/controller unit 34 that translates the sensor signal to a control signal and then transmits the control signal to appliance 32 to effect control of appliance 32. In particular, the processor/controller unit 34 processes the sensor outputs to determine the motion of the tongue and translates the motion to a digital or analog command for control of the appliance 32.

As illustrated in FIG. 2, in one embodiment of the presently disclosed subject matter, the wireless receiver 30 and its antenna 36 can be incorporated as an integral component of appliance control unit 14. The appliance control unit 14 can be a commercially-available device modified to function as intended with the presently disclosed subject matter. Exemplary devices can include or be a mobile phone, a smartphone, a PDA, a computer, and a media player. A media player can include or be any device suitable for displaying images, and/or playing sounds and/or video. The appliance control unit 14 can include a processor, memory, an input interface, and/or an output interface. The appliance control unit can also provide the subject (e.g., user) with visual or audio feedback related to the menu being selected or the function being performed. The appliance control unit can include a graphical user interface (GUI), which displays the results of the subject's selections and the current status of the assistive apparatus.

Figure 6A:
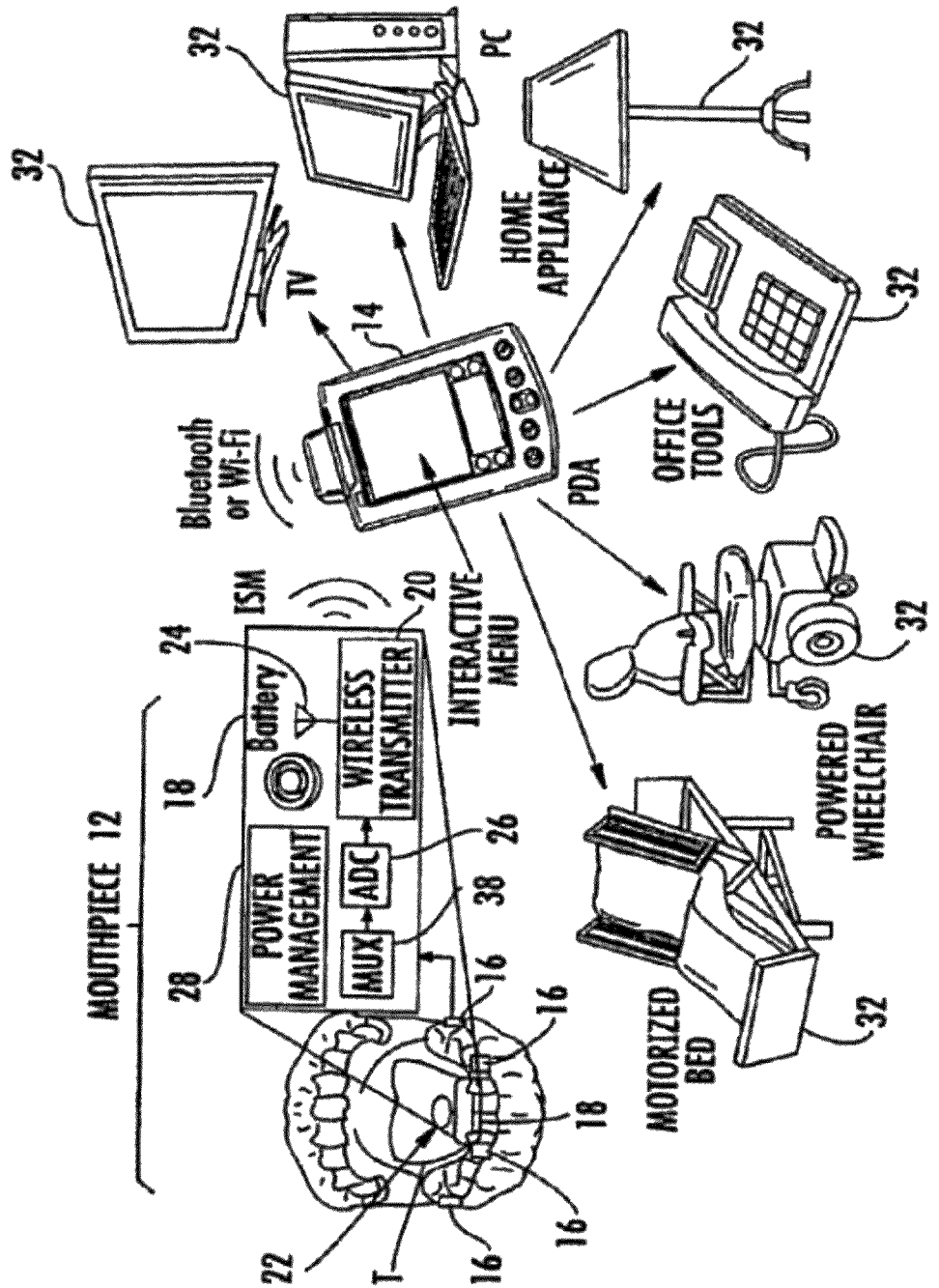
FIG. 6A is a schematic drawing of an assistive apparatus insertable into a user's mouth, showing interaction of the various components with each other and an appliance to be controlled, in accordance with an exemplary embodiment of the present invention.

FIG. 6A schematically depicts a particular embodiment of assistive apparatus disclosed herein, with specific components and functioning to interact with multiple appliances 32. The tracer unit 22 comprises a magnet and is affixed to tongue T. The sensor control unit 18 comprises power management circuitry 28, which distributes battery power between the sensors 16 and other circuit blocks. The power management circuitry 28 scans through magnetic sensors 16 at a rate well above the speed of tongue T movements (e.g., about 100 Hz) and turns them on, one at a time, in order to save power and increase the battery life. The analog sensor outputs can then be time division multiplexed (TDM) onto a single analog line by a multiplexer (MUX) 38, digitized by the ADC 26, modulated, and transmitted to the external part of the system, appliance control unit 14, which in FIG. 6A is exemplarily shown as a PDA, across a wireless link between the wireless transmitter 20 and the wireless receiver 30 in the industrial-scientific-medical (ISM) band, for example. The PDA used for this embodiment as appliance control unit 14 can be equipped with an ISM-band receiver, which is commercially available.

Figure 6B:
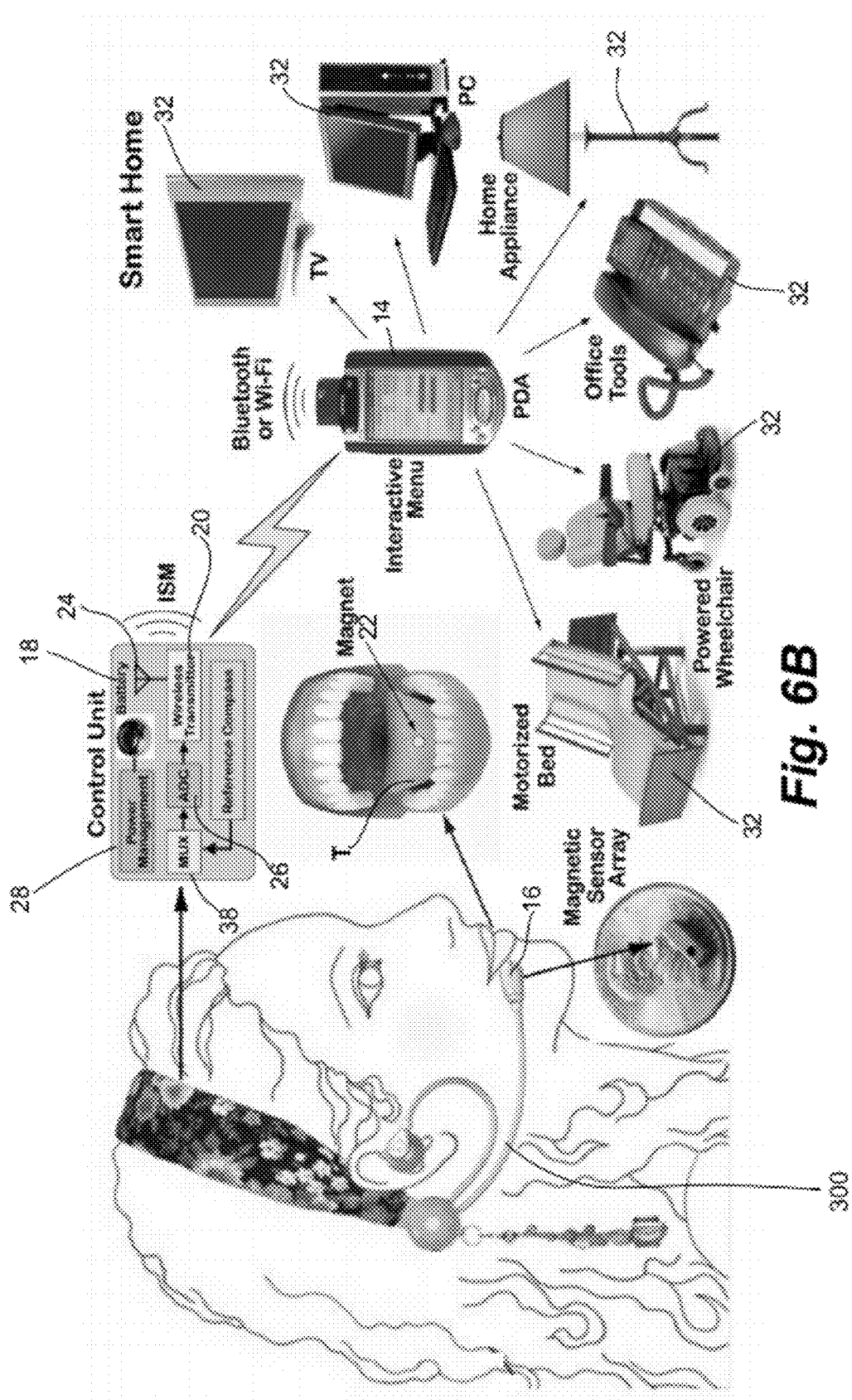
FIG. 6B is a schematic drawing of an assistive apparatus positionable external to the user's mouth, showing interaction of the various components with each other and an appliance to be controlled, in accordance with an exemplary embodiment of the present invention.

Now referring to FIG. 6B (as well as FIG. 42, FIGS. 43A-43B and FIGS. 44A-44B), the appliance control unit 14 can be located close to the subject, for example worn by the subject on a belt or attached to a wheelchair. As a result, the sensor control unit 18 power can be very small as the transmission range does not need to exceed about 1-3 m, for example. The signals received by the PDA can be demodulated and demultiplexed to reconstruct the individual sensor outputs. The PDA can either process the sensor signals by itself or wirelessly transmit them to a processing system 40 (e.g., a PC) that is within the user's environment via BLUETOOTH® or Wi-Fi, for example. By processing the sensor signals, which are proportional to the intensity of the magnetic field perpendicular to the surface of every sensor 16, the real-time position and orientation of the permanent magnet within tracer unit 22 with respect to the sensor array constellation, and consequently the tongue within the oral cavity can be determined.

The software running on appliance control unit 14 (PDA in FIGS. 6A-6B) or a computer connects these real-time position/orientation dots (vectors) and extracts a trajectory of tongue T movement. The software can then translate the tongue T movements into cursor movements on the PDA or PC screen, similar to a mouse pointer. They can also be translated to many functions, such as left-click, right-click, and double-click, in a mouse, or proportional left, right, up, down, and pressing of a button in a joystick, or to control other appliances (e.g., on/off for a light or change in motion or position for a motorized bed or a powered wheelchair). It is also possible to assign a specific tongue movement to temporarily disable assistive apparatus 10 (e.g., standby mode) when the subject wants to talk, eat, sleep, etc. and re-enable it by another dedicated tongue movement.

By assigning certain control functions to particular tongue movements in the software, it is possible to customize assistive apparatus 10 for each individual user based on his/her oral anatomy, lifestyle, and disabilities. These customized control functions, which can also be adaptive over time, can then be used to operate a variety of appliances 32 including phones, home appliances, office tools, powered wheelchairs, and/or motorized beds either directly from the PDA or indirectly through the PC, as shown in FIG. 6.

Exemplary embodiments of the present invention also relate to methods for remote control of an appliance by a subject. In some embodiments, the method comprises providing in the mouth of a subject a tracer unit such that a change in position and/or orientation of the tongue changes position or orientation of the tracer; changing a position (and/or orientation) of the tracer unit by moving the tongue, which can change the field generated around the tracer unit, for example, when the tracer unit comprises a magnet; detecting the position of the tracer unit; generating a sensor signal based on the position of the tracer unit; and transmitting the sensor signal to an appliance control unit or directly to an appliance, wherein the sensor signal effects control of the appliance. In some embodiments, the position of the tracer unit can be detected after processing the sensor signal. In some embodiments, the tracer unit comprises a magnet, as disclosed herein.

In some embodiments, an assistive apparatus disclosed herein is utilized for remote control of the appliance. The apparatus can comprise in some embodiments the tracer unit non-obstructively affixed to the tongue, at least one sensor for detecting the position of the tracer unit and adapted for non-obstructive placement proximal the tracer unit and a sensor control unit for transmitting the sensor signal to the appliance based on the detected position of the tracer unit. In some embodiments, the at least one sensor comprises an array of sensors and the apparatus further comprises power management circuitry for controlling power distribution to the plurality of sensors. In some embodiments, the appliance is selected from the group consisting of a personal computer, a wheelchair, a bed, a telephone, a home appliance, and a speech synthesizer.

In some embodiments, the apparatus comprises an appliance control unit for receiving the sensor signal from the sensor control unit, translating the sensor signal to a control signal, and transmitting the control signal to the appliance to thereby control the appliance. In some embodiments, the appliance control unit can be a smart device, such as for example a personal digital assistant, a mobile phone or a personal computer.

In some embodiments, the subject may be partially or completely disabled, such as for example a quadriplegic subject and the apparatus provides for control of appliances that facilitate control of a disabled subject's environment so that the subject can be at least partially self-sufficient. For example, in some embodiments the appliance is a personal computer, a wheelchair, a bed, a telephone, a home appliance, and/or a speech synthesizer.

Besides allowing for control of appliances by a disabled subject, the presently disclosed assistive apparatus can facilitate communication with others by the subject either via typed text on a computer or, for example, by augmentative and alternative communication (AAC) systems. Thus, once a disabled subject becomes capable of effectively using a computer by way of the assistive apparatus disclosed herein, the subject can easily benefit from a wide range of other computer-based AAC devices and software that have already been developed for people with various types of disabilities. For example, the assistive apparatus can facilitate speech generation, which can provide tremendous benefit to subjects who are unable to talk, as a result of tracheotomy, apraxia of speech, or Amyotrophiclateral Sclerosis (ALS). The ability to make a few specific movements with the tongue can be interpreted by the system software as specific words. These selected words can then be generated by a speech synthesizer that operates on the same computer. Currently these individuals, who might also be severely disabled, need to press several buttons and basically type what they want to say. By using the presently disclosed apparatus, they can not only type what they want in a much easier way, and can also dedicate an unlimited set of tongue movements to the various words that they use more often and therefore, after some training reach communication speeds comparable to naturally-speaking individuals.

In other embodiments, the subject is not disabled and the apparatus is used by the subject to manipulate complex appliances and/or function in difficult environments. For example, the subject can be an astronaut, a pilot, a scuba diver, or a soldier and the apparatus and methods disclosed herein are utilized to facilitate manipulation of the subject's environment.

For example, when astronauts leave their spaceship to enter the open space for space walks or when they land on another planet, they need to wear a heavy and thick space suit that severely limits their movements. Even though the gloves of the space suits allow some arm and finger movements, precise movements are difficult. There have also been reports of the suite mechanical joints being locked or worn off as a result of sand and dust entering the joints. Using an assistive apparatus disclosed herein, the astronauts can use their tongue as a "third arm" to control a device wirelessly without any mechanical movement through the suite joints. For example the astronauts can control robotic arms with their tongue. Also for long-term space missions, astronauts need to minimize their energy consumption, and therefore every movement counts. As such, if they can communicate with the spaceship computers using their tongue, they can be more efficient and consume less energy compared to moving their arms and fingers.

Similar limitations exist for scuba divers that need to perform specific tasks under water. These individuals, especially when operating in deep water, also need to wear suits that limit movements of their arms and fingers. They can use their tongue along with an assistive apparatus disclosed herein to perform many specific functions, such as controlling an underwater robotic system. In this case, however, the wireless magnetic sensor signals can be transferred to the external part of the system using sonar or optical links, which are known to propagate better in water.

The assistive apparatus can also help the pilot and other crew of agile combat aircrafts to control the plane or communicate with the command center under high-G physical stress, when effective limb functions or even speech is hindered in the noisy cockpit. By tracking the tongue position, the assistive device disclosed herein can be even used to indicate whether the pilot is conscious or not. Therefore the other crew or the central command can take on control of the aircraft.

Military personnel in stealth missions can also use the apparatuses, systems and methods disclosed herein when any mechanical and apparent movement with their hands and arms can generate sound or vibrations that might reveal the location of the soldier or cause enemy reaction. In exemplary cases, the soldier can perform many functions such as talking to the central command unit or even triggering a weapon only by moving their tongues, which cannot be seen or heard or noticed by the enemy.

As noted herein, embodiments of the apparatus can function by tracking the location and trajectory of a tracer unit using one or more sensors. As such, the assistive apparatus measures the location and/or orientation of the tongue and the trajectories of the tongue movements inside the mouth cavity, which is an important factor in speech therapy and speech analysis. Those individuals with speech problems can easily wear the assistive apparatus temporarily, for example, in the form of a dental clip and a speech therapist can attach the magnet to a specific spot on their tongue with a small unobtrusive tongue clip (see, e.g., FIGS. 39A-39B) or a biocompatible tissue adhesive (e.g., DERMABOND®, Johnson & Johnson or Cyanodent®, Ellman International). As a result, the speech therapist can observe, analyze, and correct the 3-D tongue movements in real time while the patient pronounces different words.

In some embodiments, methods are provided for tracking movement, position, or both of a tongue in a subject. In some embodiments, the method comprises providing in the mouth of a subject a tracer unit such that a change in position (and/or orientation) of the tongue changes position of the tracer; optionally changing a position of the tracer unit by moving the tongue; detecting the position of the tracer unit; generating a signal based on the detected position of the tracer unit; and analyzing the signal to thereby track movement, position, or both of the tongue. In some embodiments, the signal can be transmitted to a computer for analysis and determination of tongue movement and/or position, which can aid in speech analysis and/or therapy. In some embodiments, tongue movement, position, or both are tracked a desired number of times over a time period to generate a tongue movement pattern. The tongue movement pattern can then be compared to a standard tongue movement pattern as part of a speech analysis program, a speech therapy program, or both.

The apparatus utilized for the methods can in some embodiments comprise the tracer unit non-obstructively affixed to the tongue (e.g., temporarily with a clip or a biocompatible tissue adhesive), at least one sensor for detecting the position of the tracer unit and adapted for non-obstructive placement proximal the tracer unit, and a sensor control unit for transmitting the sensor signal to a computer for analysis based on the detected position of the tracer unit. In some embodiments, the at least one sensor comprises an array of sensors and the apparatus further comprises power management circuitry for controlling power distribution to the plurality of sensors, as disclosed herein.

EXAMPLES

The following non-limiting examples are included to illustrate modes of the presently disclosed subject matter. In light of the present disclosure and the general level of skill in the art, those of skill will appreciate that the following non-limiting examples are intended to be exemplary only and that numerous changes, modifications, and alterations can be employed without departing from the scope of the presently disclosed subject matter.

Example 1

Wooden Apparatus Prototype

The first prototype system was developed to move a cursor on a PC screen based on the location of a tracer unit (a permanent magnet in this Example) relative to four Hall-effect magnetic sensors (Melexis, sensitivity >9 mV/G). The sensors were attached to wooden stands and placed at four comets of a trapezoid. This configuration roughly resembles how the sensors can be located with respect to one another when positioned on the outer surface of the lower teeth. Two sensors controlled cursor movements along the x direction and the other two, movements along the y-direction. For initial testing the sensors were spaced about 4 cm apart. This distance was even larger than the required sensor spacing in the oral cavity, ensuring that the same technique can be used in a live subject setup. The sensor data was read into an NI-DAQ PCI-6023E data acquisition card available from National Instruments, Texas Signal processing and GUI were developed in the LABVIEW® (National Instruments Corp., Austin Tex.) environment. A small disk shaped permanent magnet (RadioShack, Fort Worth, Tex.; model no. 64-1895, ⅛" rare earth magnet) was used as a tracer unit and mounted on a cardboard stand at the same height as the sensors and moved in the space between the sensors. Detailed specification of the permanent magnet and equations governing its magnetic field strength are discussed in Example 3 herein below.

The LABVIEW® code for this prototype system provides two modes of operation:

1. Proximity Detection: The cursor movement is controlled by the sensor closest to the permanent magnet, with a "dead-zone" for the resting position of the magnet in which none of the sensors have control over the cursor. The proximity detection mode is similar to a switching (on/off) operating mode. For example, if the magnet is within a certain range of the front left sensor as set by a software threshold, the cursor moves to the left. In an improved version of the software, proportional controlling capability was added to the system such that an increment in the sensor output in a certain direction would accelerate the cursor movement in that direction.

2. Motion Detection: In this mode, in addition to the proximity requirement (of having the magnet close to one of the sensors), there is an additional requirement for the magnet to be in motion, i.e. the system looks for movement of the magnet in addition to its position relative to the sensors. For example, the cursor will not move no matter how close the magnet may be to the sensor if the magnet is held steady. This mode was provided for better and more accurate control over cursor movements by resembling a computer mouse. For instance, this mode proves to be effective when the cursor has to be moved in small increments at a time. Motion detection is performed by comparing the derivative of the sensor array outputs with an adjustable threshold level.

Discussion of Example 1

Even though it is possible to determine the absolute position of the permanent magnet (on the tongue) in the confined space of the mouth cavity based on the sensor array outputs, this may not always be the desired way for controlling the cursor movements. This is because of a convenience issue. If the cursor position is solely determined by the position of the magnet, when the tongue is moved back to its resting position, the cursor would also move back with it. In comparison to the way a computer mouse functions, such a movement may not be desirable, as the cursor position needs to be retained after each sweep of the magnet. Therefore, it can be desirable for the cursor to only follow the magnet relative movements compared to its previous position.

In a computer mouse, for moving the cursor over long distances across the screen it becomes necessary to lift the mouse off the surface, when it reaches the boundary of the mouse pad or normal working area, and reposition it somewhere in the middle. A single sensor could be used to detect both to and fro linear motion of the magnet. In an effort to address an issue of no practical way of actually lifting the magnet off the oral cavity space to stop its effect on the sensors, in some embodiments, at least two sensor outputs can be processed to derive each direction of linear movement. With additional signal processing, certain tongue movements can be defined as cursor movement disabling/enabling actions.

The concerns stated above can be overcome partially or fully based on classifying certain tongue movements as those intended for cursor motion, and other movements for other tasks such as mouse right/left or single/double clicks. The deciphering of the type of tongue movement from sensor array output signals can be provided in the signal processing software. One task of the software then can be to clearly and unambiguously distinguish/decouple one tongue movement from another.

Example 2

Subject Testing Apparatus

Mouthpiece

A prototype assistive apparatus was devised to evaluate the feasibility and performance of the presently disclosed assistive devices. One purpose of the prototype device was to move a cursor on a computer screen based on the location of a tracer unit (a permanent magnet (e.g., see Table II)) relative to four Hall-effect magnetic sensors (e.g., model A1321, Allegro Microsystems, Inc., Worcester, Mass.). Four Allegro A1321 ratiometric linear Hall-effect sensors with 5 mV/G sensitivity were installed along with 0.1 pF surface mount decoupling (SMD) capacitors in cavities created in a SHOCK DOCTOR MAX™ mouth guard (Shock Doctor, Inc., Plymouth, Minn., U.S.A.). The sensors readily provide temperature compensated linear voltage output proportional to the vertical magnetic field. The front two sensor outputs were used to control the cursor movements along the X direction and the rear two, movement along the Y direction. The arrangement of sensors was at the corners of a parallelogram. A set of six wires was used for supply and sensor output connections.

Control Hardware and Wireless Link

The ADC, control hardware, and wireless link were implemented using the CROSSBOW TELOS™ Research Platform (Crossbow Technology, Inc., San Jose, Calif.). This platform provides a low-power microcontroller (TI MSP430) including an 8-channel ADC, and an IEEE 802.15.4 radio transceiver with up to 250 kB/s data rate across 30 m indoor range for transmission and reception of the digitized sensor array data and adjustment/calibration commands. A TPR2400 mote and a TPR2420CA mote (Crossbow Technology, Inc.) were used, either of which could be configured as a transmitter or receiver. In this system, the internal mouthpiece incorporates the Hall-effect sensors, which are hardwired to the transmitter mote and powered by 4 size-AA batteries in a pack that can be carried in a shirt pocket. The receiver mote sits in the USB port of a personal computer, which runs the assistive apparatus system software in LABVIEVV®, and derives power directly from that port. The motes run the open-source TinyOS operating system, code for which is written in the NesC language.

TABLE II

| 64-1895 ⅛" RARE EARTH SUPER MAGNET* SPECIFICATIONS | |
|---|---|
| Material | Neodymium-Iron-Boron |
| Residual Induction (Br) | 10,800 Gauss |
| Coercive Force (HC) | 9,600 Oersted |
| Peak Energy Density (BHmax) | 30 MGO |
| Magnetizing Force (HS) | 35,000 Oersted |
| Curie Temperature | 310° C. |
| Density | 7.4 g/cm3 |
| Diameter | 4.7 mm |
| Thickness | 1.2 mm |

*RadioShack, Fort Worth, Texas

Software

The transmitter mote scans through an array of 4 ADC channels in a round-robin fashion. The data is organized into packets and transmitted wirelessly to the receiver. A radio-to-serial link program running on the receiver mote sends the packets containing sensor readings to the USB port. The code for Telos-B/LABVIEW® interfacing has been written by making use of the LABVIEW® serial port access resources. The packet data is deciphered to interpret the sensor readings contained therein before being passed to the cursor control GUI code.

The GUI has 2 modes of operation. (1) Proximity Detection (PD) Mode: The cursor movement is controlled by the sensor closest to the magnet, with a "deadzone" for the resting position of the tongue in which none of the sensors have control over the cursor. For example, if the magnet is within a certain range of the front left sensor as set by a software threshold, the cursor moves to the left. (2) Motion Detection (MD) Mode: In addition to the proximity requirement, there is a need for the magnet to be in motion, i.e., the system looks for movement of the magnet in addition to its position relative to the sensors. The cursor will not move no matter how close the magnet may be to the sensor if the magnet is held steady. This mode is provided for better control over cursor movement, for instance when it has to be moved in small increments at a time. Motion detection is performed by comparing the derivative of each sensor output to a threshold.

The LABVIEW® GUI developed for the prototype tongue drive system displays a large rectangular marker as a target in a random position for tracking by a smaller circular cursor. Proportional control is incorporated in the system by accelerating the cursor (moving by a larger step-size) the closer the magnet is held to a sensor. The marker disappears and reappears at a different location when the subject reaches it with the cursor and executes a "tongue click". Left and right mouse-clicks are available in this system using the tongue movement. If the subject quickly flicks the magnet towards one of the front sensors starting from the deadzone, it is considered a tongue click. These special tongue movements allow the subject to "select" and "drag" an icon on screen represented by a target marker. The GUI software has tuning controls in the form of amplitude thresholds for PD mode, differential thresholds for MD mode, and thresholds for sensing tongue clicks.

It should be noted that adaptation and learning capability of the brain helps the subject to quickly learn how to use the presently disclosed assistive apparatus very effectively and quickly. Another advantage of the presently 30 disclosed assistive apparatus is that a substantially unlimited number of specific tongue movements can be defined and dedicated to specific functions based on the subject's preferences and abilities. These movements can then be fine tuned over time for each individual subject. For example, special tongue movements allow the subject to "select" and "drag" an icon on the screen. The GUI software also has several adjustable control parameters in the form of amplitude thresholds, gains, filter bandwidths, etc. that can optimize the performance of the apparatus in different conditions.

Example 3

Permanent Magnet and Hall-Effect Sensor Experiments

Magnetic Induction (B) and Magnetic Field Strength (H)

The magnetic fields generated by currents and calculated from Ampere's Law or the Biot-Savart Law are characterized by the magnetic field B measured in Tesla. But when the generated fields pass through magnetic materials which themselves contribute internal magnetic fields, ambiguities can arise about what part of the field comes from the external currents and what comes from the material itself. It has been common practice to define another magnetic field quantity, usually called the "magnetic field strength" designated by H. It can be defined by the relationship:

$$H = B_0/N_0 = B/\mu_0 - M$$

and has the value of unambiguously designating the driving magnetic influence from external currents in a material, independent of the material's magnetic 20 response. The relationship for B can be written in the equivalent form:

$$B = \mu_0(H+M)$$

H and M will have the same units: amperes/meter (SI) or Oersted (CGS). To further distinguish B. from H, B is called the magnetic flux density or the magnetic induction. The quantity M in these relationships is called the magnetization of the material.

Another commonly used form for the relationship between B and H is $$B = \mu H$$

where $$\mu = K_m \mu_0$$

No being the magnetic permeability of space and $K_m$ the relative permeability of the material. If the material does not respond to the external magnetic field by producing any magnetization, then $K_m = 1$.

The B–H Curve

The basis of permanent magnet design is the B–H curve, or hysteresis loop, which characterizes each magnet material. This curve describes the cycling of a magnet in a closed circuit as it is brought to saturation, demagnetized, saturated in the opposite direction, and then demagnetized again under the influence of an external magnetic field.

The second quadrant of the B–H curve, commonly referred to as the "Demagnetization Curve", describes the conditions under which permanent magnets are used in practice. A permanent magnet will have a unique, static operating point if air-gap dimensions are fixed and if any adjacent fields are held constant. Otherwise, the operating point will move about the demagnetization curve, the manner of which must be accounted for in the design of the device.

The three most important characteristics of the B–H curve are the points at which it intersects the B and H axes (at Br—the residual induction—and $H_c$—the coercive force—respectively), and the point at which the product of B and H are at a maximum ($BH_{max}$—the maximum energy product). Br represents the maximum flux the magnet is able to produce under closed circuit conditions. In actual useful operation permanent magnets can only approach this point. He represents the point at which the magnet becomes demagnetized under the influence of an externally applied magnetic field. $BH_{max}$ represents the point at which the product of B and H, and the energy density of the magnetic field into the air gap surrounding the magnet, is at a maximum. The higher this product, the smaller need be the volume of the magnet. Designs should also account for the variation of the B–H curve with temperature.

When plotting a B–H curve, the value of B is obtained by measuring the total flux in the magnet (Ø) and then dividing this by the magnet pole area (A) to obtain the flux density (B=Ø/A). The total flux is composed of the flux produced in the magnet by the magnetizing field (H), and the intrinsic ability of the magnet material to produce more flux due to the orientation of the domains. The flux density of the magnet is therefore composed of two components, one equal to the applied H, and the other created by the intrinsic ability of ferromagnetic materials to produce flux. The intrinsic flux density is given the 5 symbol Bi where total flux $B = H + B_i$, or, $B_i = B - H$. In normal operating conditions, no external magnetizing field is present, and the magnet operates in the second quadrant, where H has a negative value. Although strictly negative, H is usually referred to as a positive number, and therefore, in normal practice, $B_i = B + H$. It is possible to plot an intrinsic as well as a normal B–H curve.

One Dimensional Measurements of Magnetic Field Strength

The strength of a magnetic field drops off exponentially over distance. For magnet materials with straight-line normal demagnetization curves such as Rare Earths and Ceramics it is possible to calculate with reasonable accuracy the flux density at a distance X from the pole surface (where X>0) on the magnet's centerline under a variety of conditions.

Figure 7A:
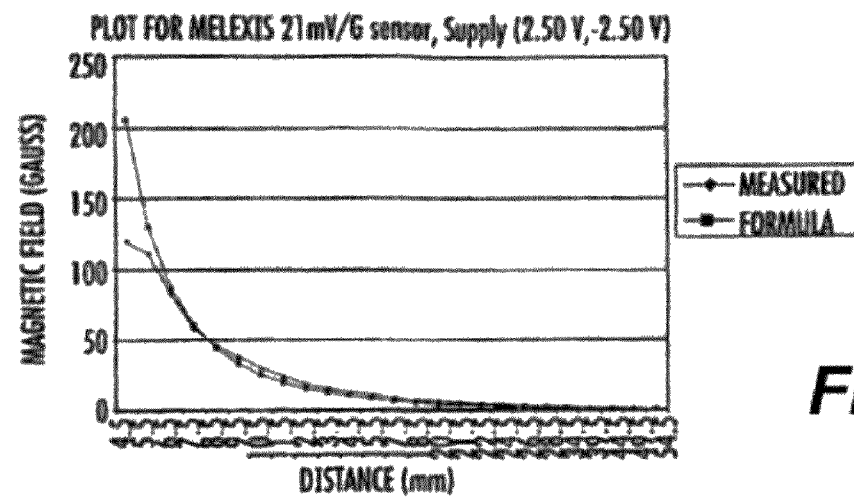
FIG. 7A-7C are graphical representations showing magnetic field intensity (Br) versus distance (x) plots for Melexis 21 mV/G (FIG. 7A), Melexis 9 mV/G (FIG. 7B), and Allegro 1.31 mV/G (FIG. 7C) Hall-effect sensors, in accordance with an exemplary embodiment of the present invention.
Figure 7B:
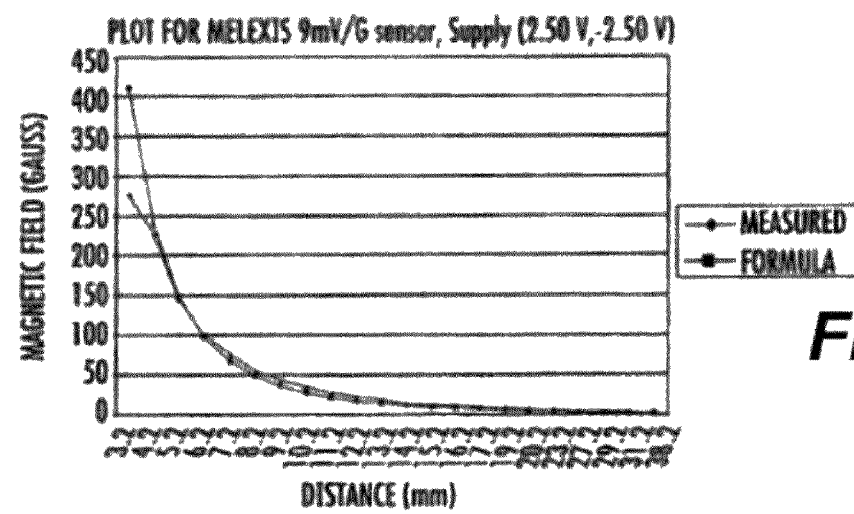
Figure 7C:
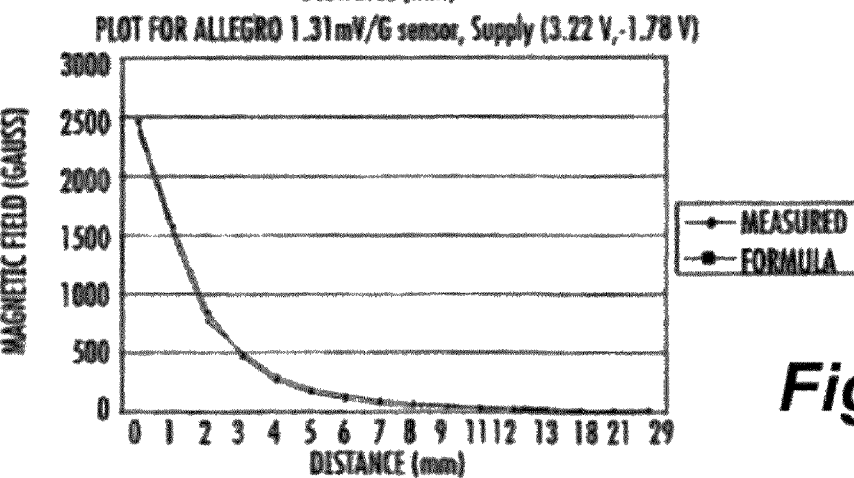

For a cylindrical or disc shaped magnet with a radius of R and Length L, the magnetic induction at the centerline of the magnet a distance X from the surface can be calculated by the following formula, where Br is the Residual Induction of the material In order to verify the theory as given by the above equation with experimental results, a wooden apparatus was constructed with the Hall-effect sensor attached to one wooden stand and the magnet to another, as disclosed in Example 1. Using this setup, the Hall Sensor was fixed in position and the magnet was shifted at different distances from the sensor, along a straight line. The permanent magnet used was a Single ⅛" rare earth magnet (model 641895 from RadioShack) which exemplary specifications are summarized in Table II. The Hall-effect sensors used were from Melexis (Concord, N.H.) with 21 mV/G and 9 mV/G sensitivities and from Allegro Microsystems with 1.31 mV/G sensitivity. For all 3 sensors, the experimental results, shown in FIGS. 7A-7C, matched theoretical predictions with reasonable accuracy.

Two Dimensional Measurements of Magnetic Field Strength

The same apparatus utilized in the 1-D measurements and disclosed in Example 1 was used to characterize the magnetic field of a permanent magnet in a plain (2-D). The utility of these experiments was to predict and observe trends of the magnetic induction, B, variations with respect to relative sensor and permanent magnet positions. When both sensor and magnet are located perpendicular to a 2-D plain, B changes with x, y, and (I), which are distance along X axis, distance along Y axis, and relative orientation of the sensor and magnet, respectively. Since no simple closed form equation for magnetic field in 2-D when sensor and magnet dimensions are comparable to their relative distance is available, the experimental data was compared with the results from the FEMLAB® Magnetostatics Modeling module (Comsol Inc., Stockholm, Sweden). FEMLAB® is an interactive environment to model single and coupled phenomena based on partial differential equations (PDE).

Figure 8A:
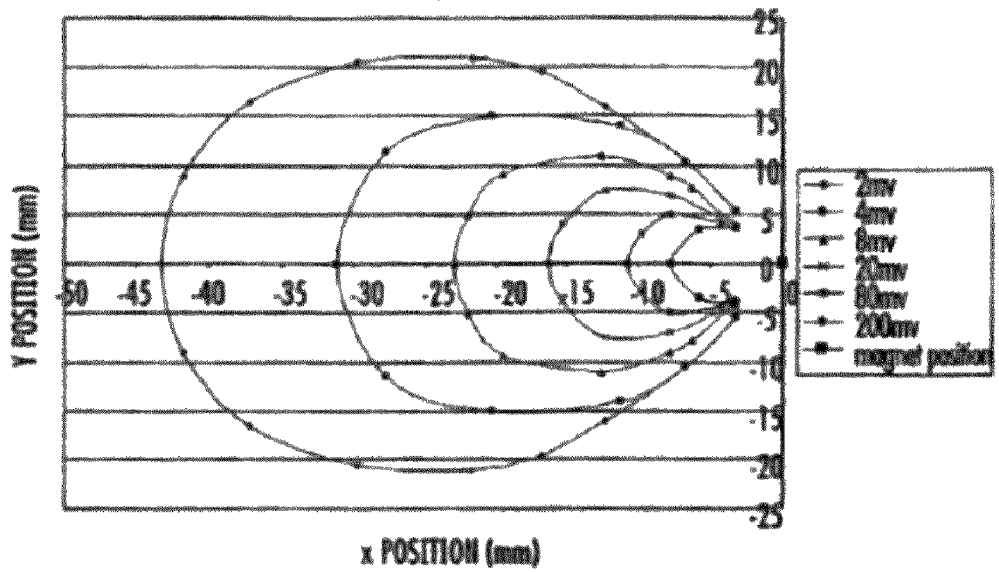
FIGS. 8A-8B are graphical representations showing experimentally measured isopotential curves for magnet centerline perpendicular to the plane of a Hall-effect sensor, i.e., sensor and magnet were in parallel planes (FIG. 8A) and FEMLAB isopotential curves for magnet centerline perpendicular to plane of a Hall-effect sensor (FIG. 8B), in accordance with an exemplary embodiment of the present invention.
Figure 8B:
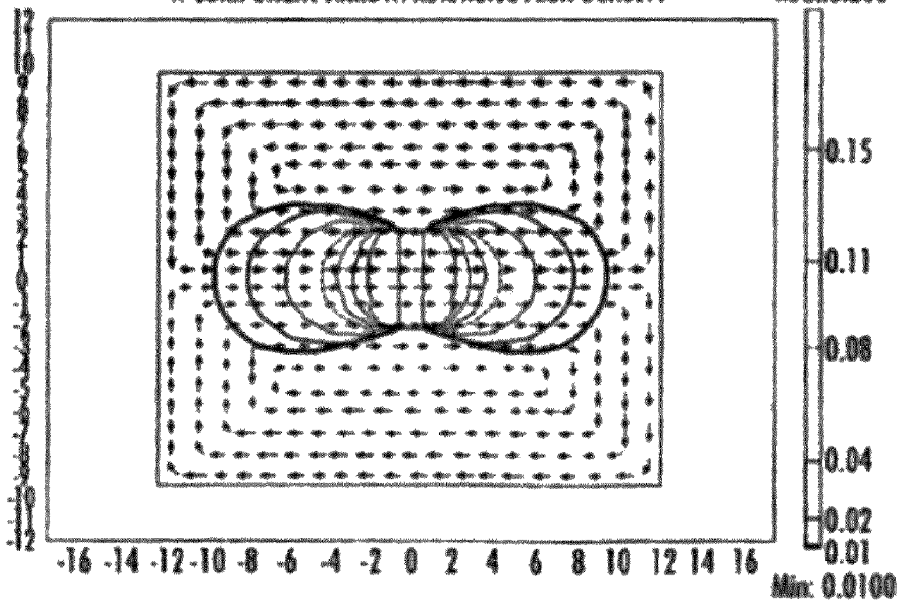

In all of the following experiments, the position of the sensor was kept constant and the magnet was moved with respect to the sensor while measuring the sensor output voltage, which is monotonically related to B according to the 1-D experiments disclosed herein. Then the magnet positions which resulted in constant sensor output voltage (constant B) where connected to one another to create a set of isopotential curves. A FEMLAB® 2-D model comparable to the RadioShack 64-1895 ⅛" rare earth magnet specification was also constructed, which included the following parameters:
1. Magnet Length=1.2 mm
2. Magnet Height=4.7 mm
3. Magnet Material Relative Permeability==5000 (assumed)
4. Magnet Residual. Induction=Br=10800 Gauss Case I: Isopotential Curves for Magnet Centerline Perpendicular to Plane of Hall Sensor In this setup, the Hall Sensor (Allegro 1.31 mV/G, Supply=3.22 V, −1.78 V, Quiescent Output=0.83 mV) was fixed in position and the magnet (RadioShack 64-1895 ⅛") was positioned at different points in the 2-D plane at the same height as the sensor with its centerline always perpendicular to the plane of the Hall sensor, i.e., sensor and magnet were in parallel plains. FIG. 8A shows the experimental isopotential curves resulting from this experiment. The equivalent FEMLAB® post-simulation result is seen in FIG. 8B. In order to obtain these curves, the x-component of the magnetic flux density was plotted as contours, since the Hall sensor only responds to the flux density perpendicular to its plane.

Figure 9A:
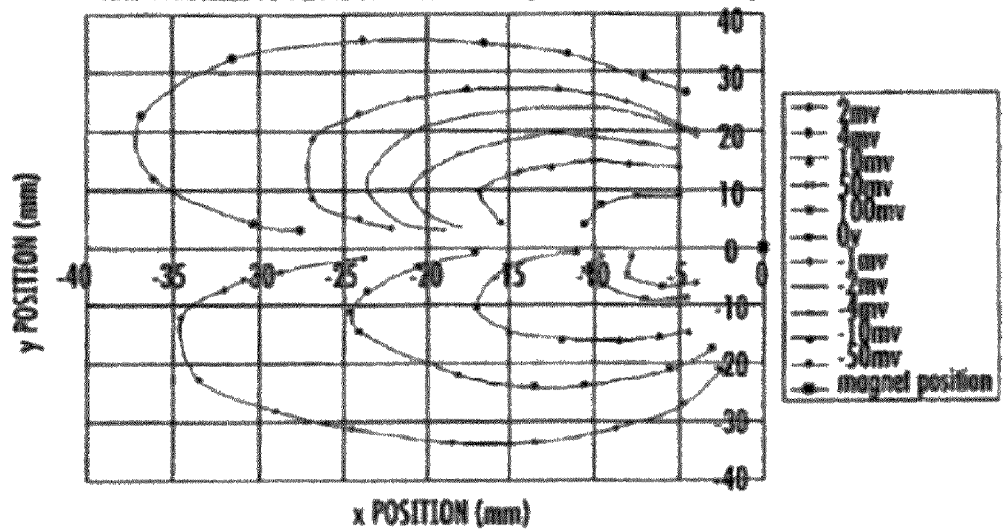
FIGS. 9A-9B are graphical representations showing experimentally measured isopotential curves for magnet centerline horizontal and parallel to plane of a Hall-effect sensor, i.e., sensor and magnet are in perpendicular planes (FIG. 9A) and FEMLAB isopotential curves for magnet centerline horizontal and parallel to plane of a Hall-effect sensor (FIG. 9B), in accordance with an exemplary embodiment of the present invention.
Figure 9B:
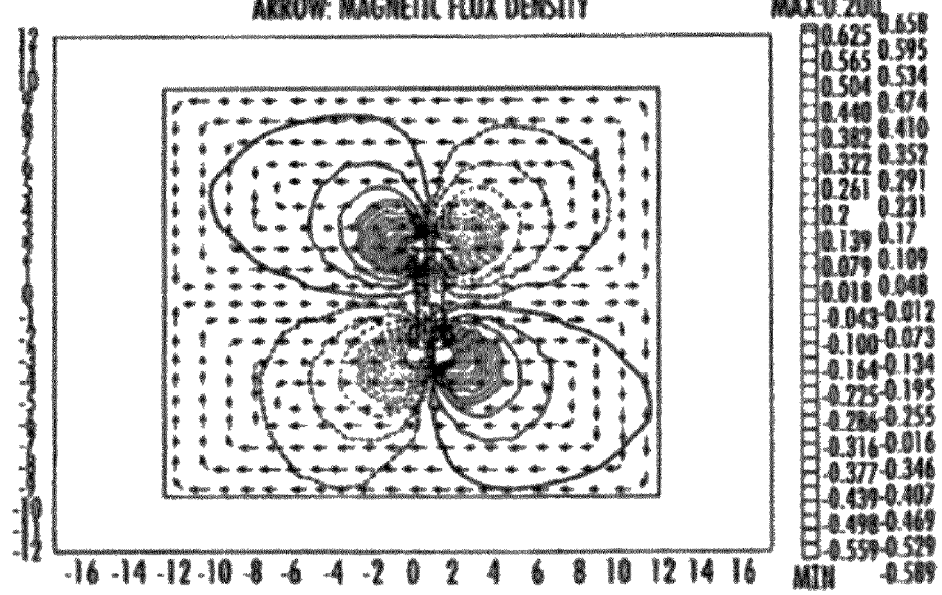

Case II: Isopotential Curves for Magnet Centerline Horizontal and Parallel to Plane of Hall-Effect Sensor In this setup, the Hall Sensor was fixed in position and the magnet was positioned at different points in the 2-D plane at the same height as the sensor with its centerline always horizontal and parallel to the plane of the Hall sensor, i.e., sensor and magnet were in perpendicular plains. FIG. 9A shows the experimental isopotential curves resulting from this experiment. The equivalent FEMLAB® post-simulation result is shown in FIG. 9B. In order to obtain these curves, the y-component of the magnetic flux density was plotted as contours.

As can be seen from a comparison of simulation with experimental data, in Case I and Case II, the curves are similar in nature. The magnet model can be further refined and its parameters tweaked until an exact a match is obtained, if desired.

Figure 10:
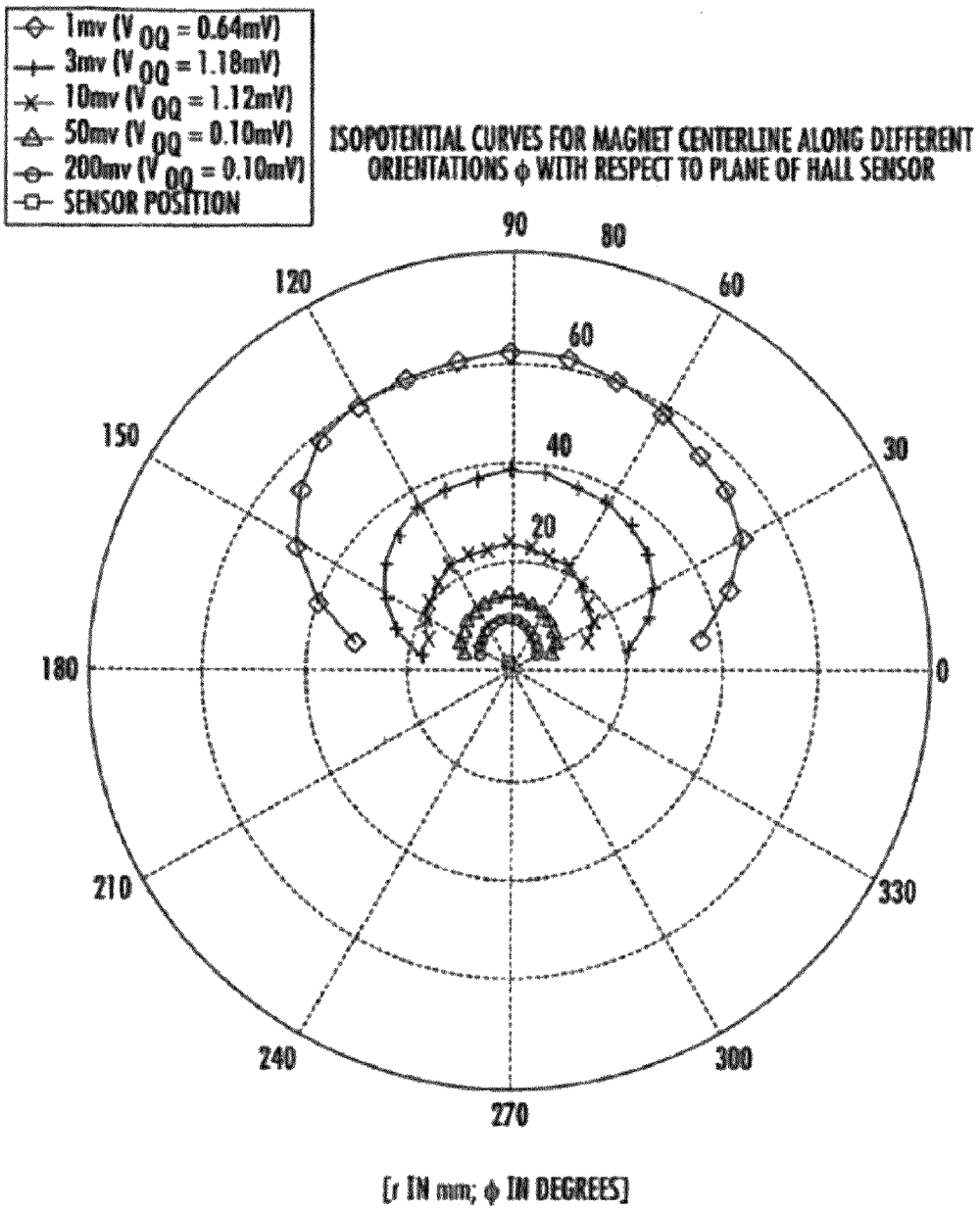
FIG. 10 is a graphical representation showing experimentally measured isopotential curves for magnet centerline along different orientations with respect to plane of a Hall-effect sensor (relative to sensor), in accordance with an exemplary embodiment of the present invention.

Case III: Isopotential Curves for Magnet Centerline Along Different Orientations cp with Respect to Plane of Hall-Effect Sensor In this setup, the Hall Sensor was fixed in position and the magnet was positioned at different points in the 2-D plane at the same height as the sensor with its centerline along different orientations cp with respect to plane of Hall sensor. FIG. 10 shows the experimental isopotential curves resulted from this experiment.

Example 4

Development of Next Generation Assistive Apparatus

The assistive apparatus disclosed herein can employ ECO™, an ultra-compact low-power wireless sensor node, which has been developed at the Center for Embedded Computer Systems at the University of California in Irvine (UC-Irvine) for real-time motion monitoring of infants. An attractive feature of the ECO™ sensor node is its small size, which is about 12×12×7 $mm_3$ including a 48 mAh rechargeable battery that can easily fit inside the mouth. ECO™ has a power management system in the form of a step up regulator, which produces a constant 3 V supply for the sensors regardless of the gradually dropping battery voltage. The microcontroller used in ECO sensor node (nRF24E1; Nordic Semiconductor, Oslo, Norway) has a built-in 9-channel ADC and a 2.4 GHz transmitter with 1 Mbps data rate. Therefore, almost no additional circuitry is needed.

The average power consumption of the ECO sensor node with the transmitter on is about 14 mA and with the transmitter off is about 4 mA. In the standby mode, ECO sensor node consumes about 60 pA. The A1391 Hall-effect sensor consumes about 3.2 mA when operational and about 25 pA in sleep mode. Therefore, ECO sensor node and four sensors consume about 160 pA in standby mode and about 17.3 mA when active (one sensor on at a time). If the firmware keeps the ECO sensor node in the standby and active modes in 90% and 10% of the times, respectively, the current consumption of the assistive apparatus mouthpiece will be about 2 mA. Thus a 48 mAh battery can last about 24 hours. Therefore, the battery needs recharging only every 2 or 3 days. Alternatively, a 560 mAh non-rechargeable battery can last about 280 hours or more than 2 weeks before it needs to be replaced.

The assistive apparatus can also include a control unit designed specifically for the presently disclosed applications based on a custom PCB using a combination of custom and commercial ASICs. This design can be even smaller and consume less power than an apparatus using the ECO sensor node because the ECO™ sensor node has several components such as acceleration and light sensors that are not necessary for the assistive apparatus disclosed herein. In addition, smaller and more capable, micro-controllers and commercial ASICs with even lower power consumption can be developed and can be incorporated into embodiments of the assistive apparatus.

As mentioned, the assistive apparatus can comprise microcontroller firmware for the sensor control unit, which can be developed in concert with the apparatus. This process can employ sample codes from the UC-Irvine project and the support available from the microcontroller's manufacturer (nRF24E1: 2.4 GHz Transmitter/MCU/ADC available from Nordic Semiconductor). The firmware can be developed to facilitate providing continuous real-time sensor data at a high rate to the appliance control unit, while saving power by maximizing the amount of time when different sensor control unit components are held in the sleep mode.

Example 5

Development of Signal Processing Algorithms for Detection of the 3-D Position and Orientation of Tracer Unit The apparatus tested in Example 2 was fully functional by simply associating each sensor output to one major direction (N, S, E, and W). Using sensor outputs to indicate the 3-D position and orientation of the magnet inside the mouth can result in further benefits to the assistive apparatus, such as dedicating specific tongue trajectories to predefined commands and functions. For developing these algorithms powerful FEA modeling and simulation tools, such as Comsol Multiphysics (FEMLAB®) Electromagnetics module (Comsol Inc., Stockholm, Sweden) and MAXWELL® 3D (Ansoft, Pittsburgh, Pa., U.S.A.), can be utilized.

Example 6

Development of the GUI and Driver Software for Subject Interface

Required assistive apparatus software can be developed on a processing system in C++, Java, MATLAB, LABVIEW®, and other programming languages under, for example the WINDOWS XP® operating system (Microsoft Corporation, Redmond, Wash.). After the software is developed and debugged on PC, it can be transferred to a smart device, for example a PDA, using WINDOWS® MOBILE® operating system. In order to save battery power on the sensor control unit, the unit can be configured to not perform any processing on the sensor signals. The raw samples can be directly transmitted to the external smart device, where all the processing algorithms are applied to the received signals after the samples are time division demultiplexed.

Mouse functions can be replaced with the assistive apparatus functions, such that the subject would not need to run any other software or learn any new environment or GUI other than the WINDOWS® operating system itself. The mouse functions can be a small subset of the assistive apparatus functions. Considering the flexibility of the presently disclosed assistive apparatus capabilities, the subject can literally define a substantially unlimited number of functions by creating a library of his/her specific tongue movements.

Another component of the presently disclosed apparatus software is a library of drivers and applications to interface with other equipments and home/office appliances as shown in FIG. 6A-6B. Fortunately, the PC is already a hub for replacing or communicating with most of home/office appliances and WINDOWS® already includes many of these drivers. Additional device drivers can be specifically developed for the assistive apparatus, such as interfacing with a powered wheelchair or motorized bed.

Tongue Drive System

In an exemplary embodiment, the system can be described as a tongue drive system for driving a particular apparatus. There are many advantages to using the tongue over other parts of a moving subject. For example and not limitation, first, because the tongue and the mouth occupy an amount of sensory and motor cortex that rivals that of the fingers and the hand, they are capable of sophisticated motor control and manipulation tasks; this is evident from their usefulness in swallowing and vocalization. Second, the tongue movements in the oral cavity are fast and offer many degrees of freedom. Third, the tongue is connected to the brain by the cranial nerve, which generally escapes severe damage in spinal cord injuries and is often one of the last parts of the body to be affected in most neuromuscular degenerative disorders such as ALS. Fourth, the tongue muscle is similar to the heart muscle in that it does not fatigue easily. Fifth, an oral device involving the tongue could be mostly hidden from sight inside the oral cavity, thus offering a cosmetic advantage and a degree of privacy for the user. Sixth, the tongue muscle is not afflicted by repetitive motion disorders that can arise when a few exoskeletal muscles and tendons are regularly being used. Seventh, the tongue is not influenced by the position of the rest of the body, which may be adjusted for maximum user comfort. Eighth, the tongue can function during random or involuntary neurological activity such as muscular spasms. Ninth, tongue movements are very natural, effortless, and do not need a lot of thinking or concentration. And tenth, non-invasive access to the tongue movements is possible.

Accordingly, there are many advantages to the tongue drive system. In addition to the advantages of using the tongue as the control means, there are still other advantages. Some non-limiting examples include continuous proportional control, easy to learn functionality, its small size, low power consumption, robustness, flexibility and adaptability, easy usage, and modularity.

For continuous proportional control, the signals from the magnetic sensors are functions of a continuous proportional position-dependent property, namely the magnetic field intensity. A small number of sensors are able to capture an unlimited number of tongue positions and movements. These sensors are advantageous over switch-based devices in that the user can communicate with his/her environment in a much more natural and faster way. The user is saved the trouble of operating multiple switches in a sequential or parallel way.

Functionality of the tongue drive control is easy to learn. In alternative assistive technologies that emulate an ordinary computer mouse, besides the primary method for moving the mouse pointer, an additional input device such as a switch needs to be included for the mouse button functions (a.k.a. mouse clicks). In the tongue drive system, the additional switches are unnecessary because tongue movements can be assigned to a button press, drag and drop, double-click, and the like.

The size of the tongue drive system can have a small footprint. The sensors and their associated interfacing circuitry are monolithic integrated circuits (IC), which can be miniaturized into a compact hermetic package that can be easily fitted within a dental retainer inside the mouth cavity or on headset outside the mouth. The wireless interface and system energy source (battery) can also be very small and incorporated within the retainer. The electronics can be included on one application-specific IC (ASIC) chip, which can be packaged with a small battery and embedded inside an orthodontic brace.

The tongue drive system consumes low power. The sensors can be activated by a permanent magnet, which is an inherently passive and wireless component. The system power requirement is thus limited to the sensors and the wireless link to the data processing unit (PC or PDA).

The tongue drive system is robust. Unlike many alternative technologies, embodiments of the present method can operate satisfactorily even in the presence of noise, interference or involuntary body movements. By properly implementing a noise cancellation strategy, the system has high resilience to the interference of the external magnetic fields such as the earth magnetic field as well as tongue movements due to the speaking, coughing or other daily activities.

The tongue drive system is both flexible and adaptable. Many aspects of the tongue drive system can be customized through software parameter adjustments for a particular individual's oral anatomy, needs, capabilities, and lifestyle. The tongue drive system can serve as a platform that can address a variety of needs of different individuals at different levels of disability.

The tongue drive system is easy to use. Individuals do not need to concentrate on the movements or be in a specific physical position or mental state to be able to use the tongue drive system. Learning the movements is easy and the system can be adaptive and fine-tuned over time.

The tongue drive system has modularity. The system can be built in the form of a standard module. With little or even no modifications, it can be easily linked with a wide variety of commercially available assistive technologies, and augmentative and alternative communication (AAC) devices, such as powered wheelchair, on screen keyboards, speech synthesizers, and the like.

Exemplarily, embodiments of the tongue drive system (TDS) are depicted in FIGS. 6A-6B (and FIG. 42, FIGS. 43A-43B and FIGS. 44A-44D). A tracer unit can be carried by the tongue (as shown in FIGS. 3A-3B). In some embodiments, the tracer unit can be a small permanent magnet, which may be coated by a biocompatible non-ferromagnetic material (e.g., gold, platinum, or polymers). For protection and security, the tracer can be further connected to a string or other means outside the mouth to prevent the tracer from being swallowed or falling into the user's lungs (e.g., if a tracheotomy is used by the user). The tracer can be carried by the tongue by many ways, including but not limiting to using a tongue clip (FIGS. 39A-39B), tissue adhesive, tongue piercing (FIG. 38), or implantation, which may be dependent on the user's preference. The magnetic field generated by the magnetic tracer inside and around the mouth varies due to tongue movements.

Variations of the magnetic field intensity (B) can be detected by an array of magnetic sensors mounted on a headset 300 outside the mouth; for example, see FIG. 6B. For instance, the headset can be similar to a head-worn microphone. Alternatively, as shown in FIGS. 6A and 12A-12D, the sensors can be mounted on a dental retainer positionable inside the mouth, similar to an orthodontic brace. These sensors can be stationary with respect to one another. The tracer moves independently with respect to the sensors. In an exemplary embodiment, to conserve power, one sensor can be activated on its own to measure the magnetic field in its measurement direction at a time.

The sensor outputs can be sampled and multiplexed by an ultra low power microcontroller (MCU), and then wirelessly transmitted to an external receiver. The receiver can be connected to or included in a personal digital assistant (PDA) or portable computer (PC). The control unit may include the power management circuit, which can regulate the output voltage of a power source to a relatively low and stable voltage, for further reducing the power consumption and extending the life of the battery.

In an exemplary embodiment, the magnetic sensors, the preliminary signal conversion/processing, power management, and wireless data transmission electronics can be integrated on a single ASIC, which can be powered by a miniaturized rechargeable battery. The chip can be packaged along with the battery and incorporated in an orthodontic brace to minimize the size of electronics inside the mouth.

After the sensor signals are captured by the PC/PDA, which is positioned near the user, including but not limited to being attached to the user's clothing, bed, or wheelchair, a sensor signal processing (SSP) algorithm, running on the PC/PDA, can classify the sensor signals and convert them into user control commands. Each of these commands represents a particular tongue movement or position and can be customized based on user's abilities, oral anatomy, personal preferences, and lifestyle. These commands then can be used to wirelessly communicate with and operate a variety of devices in user's environment.

The user can also define a particular command of tongue movement to switch the tongue drive system into standby mode when he/she wants to sleep or engage in a conversation or eating. Later on, the tongue drive system can be brought back online with another dedicated tongue movement. Alternatively, the tongue movements associated with user commands can be defined such that they are sufficiently different from the tongue positions and movements that occur during speech and digestion. In this case, the SSP algorithm can discriminate between signals from tongue commands and those originated from natural tongue movements resulted from speech, eating, swallowing, coughing, or sneezing.

Figure 13A:
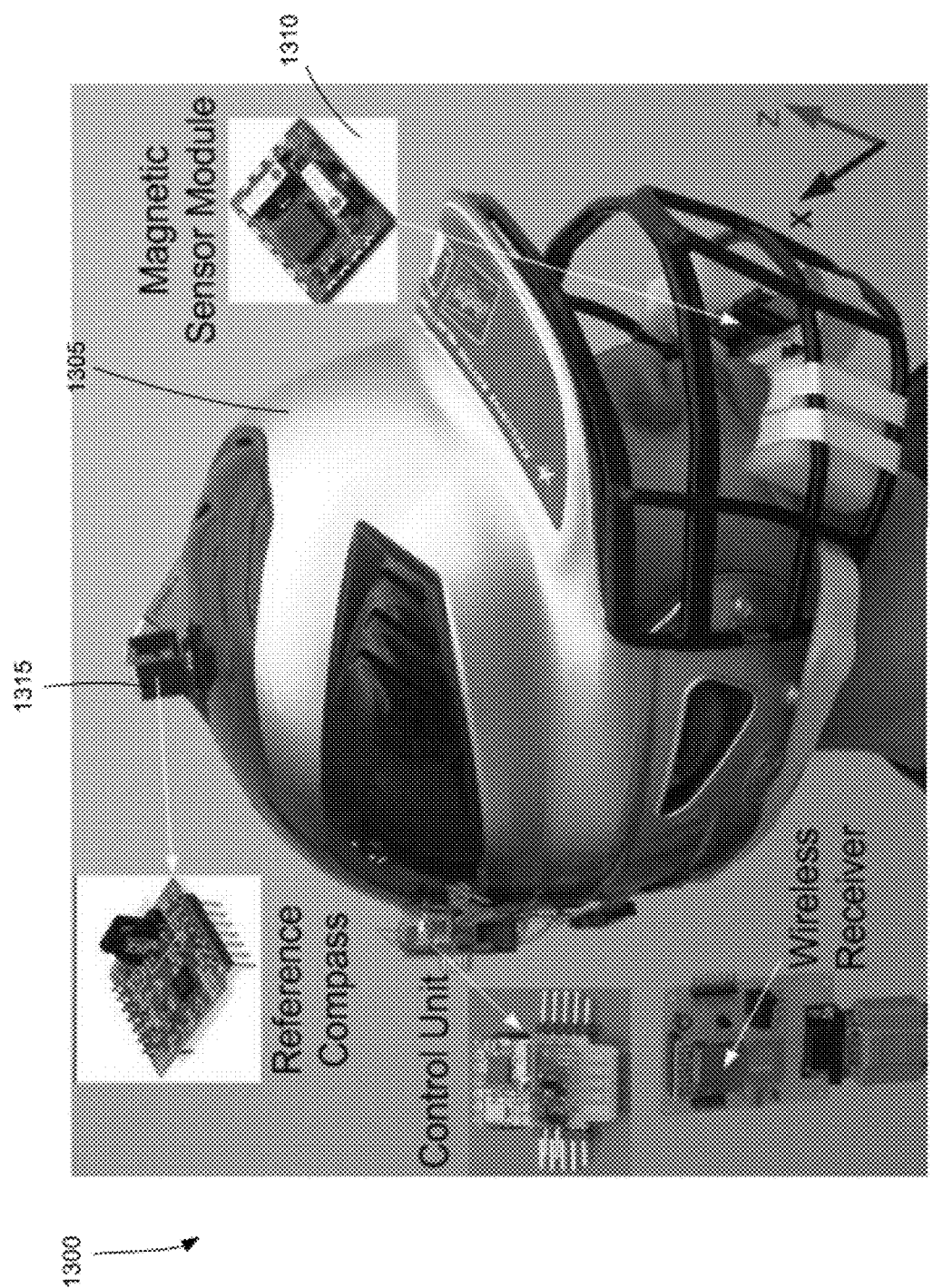
FIG. 13A is a perspective view of a helmet carrying the tongue drive system, in accordance with an exemplary embodiment of the present invention.
Figure 13B:
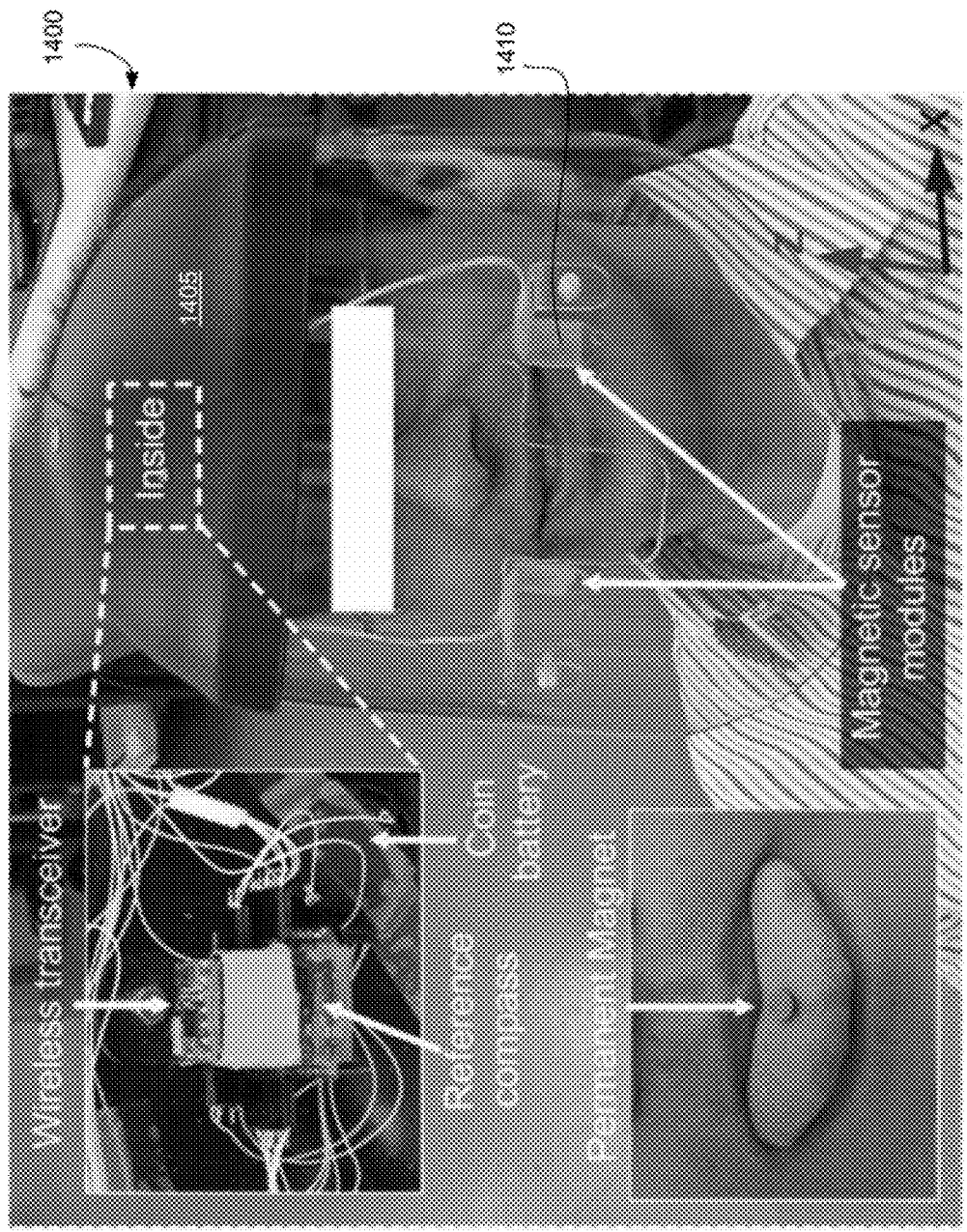
FIG. 13B is a perspective view of a face-shield carrying the tongue drive system, in accordance with an exemplary embodiment of the present invention.

An external tongue drive system (TDS) prototype 1300, as depicted in FIG. 13A, was built on a baseball helmet 1305 to facilitate optimal positioning of the sensors and other system components. A similar prototype 1400 was also built on a face-shield 1405, as shown in FIG. 13B, using the same kind of components. A purpose of these prototypes was to demonstrate the possibility of using an array of magneto-inductive sensors to effectively detect the movements of the tongue and translate them into different mouse functions to emulate a mouse for computer access. In an exemplary embodiment, six basic commands can be defined for left, right, up, and down cursor movements as well as left- and double-click gestures. As long as the SSP algorithm runs on the processing system no additional GUI or learning is necessary and users can directly make use of any piece of software or operating system that is operable by a mouse.

In some embodiments, small cylindrical rare earth permanent magnets were used as magnetic tracers. A pair of two-axis magnetic field sensor modules 1310, 1410 (e.g., PNI, Santa Rosa, Calif.) was mounted symmetrically at right angles on the face-shield close to the user's cheeks. They were close enough to the magnetic tracer to pick up the magnetic field variations resulted from the tongue movements. Each two-axis module 1310, 1410 contained a pair of orthogonal magneto-inductive sensors, shown in FIG. 13A insert. One sensor was placed along the X-axis, another sensor was placed along the Y-axis, and two sensors were placed along the Z-axis with respect to the helmet imaginary coordinates. A PNI three-axis sensor module 1315, acting as a reference three-dimensional compass, was used to measure and remove the external magnetic interference (EMI) resulted mainly from the earth magnetic field. This additional sensor was also mounted on the top of the helmet.

All seven sensor outputs, which were already in digital form, were sent serially to an ultra low-power microcontroller (e.g., Texas Instruments part number MSP430, Dallas, Tex.). The microcontroller receives a plurality of samples per second from the sensor. In an exemplary embodiment, the microcontroller receives up to 11 samples per second from each sensor, while activating one module at a time to reduce power consumption. The control unit reads and compares the right sensor module outputs with a pre-defined threshold value to locally check if the user has issued a standby/on command. This threshold can be defined as the minimum sensor output when the magnet is about 20 mm away from that sensor module. If the user holds his/her tongue close to the right module (e.g., less than about 20 mm) for more than two second, the system status can be switched between operational and standby.

When the system is in the operational mode, all seven sensors are read and their samples are packaged in one data frame and wirelessly transmitted to the processing system across an ISM-band wireless link (about 2.4 GHz) that is established between two identical low power transceivers (e.g., nRF2401A, Nordic Semiconductor, Norway). The receiver-side microcontroller can transfer the received data to the processing system through an RS-232 or Universal Serial Bus (USB) port for additional processing. The specifications of the tracer, magnetic sensor modules, and control unit are summarized in Table III.

TABLE III

EXTERNAL TDS PROTOTYPE VERSION
I EXEMPLARY SPECIFICATIONS

| Specification | Value |
| --- | --- |
| Control Unit | |
| Microcontroller | Texas Instruments - MSP430F1232 |
| Control unit dimensions | 22.5 × 18 × 16 mm³ |
| Clock frequency | 1 MHz |
| Sampling rate | 11 samples/second/sensor |
| Wireless transceiver | Nordic nRF2401 @ 2.4 GHz |
| Wireless module dimensions | 15 × 12 × 3 mm³ |
| Operating voltage/current | 2.2 V/~4 mA |
| Magnetic Sensor Module | |
| Magnetic sensors | PNI magneto-inductive, Micromag2 |
| Sensor dimensions | 6.3 × 2.3 × 2.2 mm³ |
| Sensor module dimensions | 15 × 12 × 3 mm³ |
| Sensor resolution/range | 0.015 µT/1100 µT |
| Sensor inductance | 400-600 µH @ 100 kHz, 1 Vp-p |
| Magnetic Tracer | |
| Source and type | RadioShack rare-earth super magnet: 64-1895 |
| Size (diameter and thickness) | Ø 5 mm × 1.3 mm |
| Residual magnetic strength | 10800 Gauss |

The high resolution magneto-inductive sensors 1310, 1410 not only read the magnetic field variations resulted from the movements of the magnetic tracer inside the mouth, but also the EMI (electromagnetic interference) from a variety of external sources, the most important of which is the earth magnetic field (EMF). The EMF varies due to rotations and movements of the user or when positioned near a DC magnetic field. Eliminating the effects of EMI is necessary to increase signal-to-noise ratio (SNR), enhance the tongue drive command interpretation, and reduce probability of errors.

In an exemplary embodiment, an additional 3-D sensor module 1315 can be used, which may be mounted sufficiently far from the magnetic tracer to only measure the ambient field (EMI). In an exemplary embodiment, this additional 3-D sensor module can be mounted on the top of the helmet or external device. The information received from the additional 3-D sensor module 1315 can help predict and cancel the EMI at the location of the other two 2-D sensor modules 1310, 1410 that are closer to the tracer.

In other words, the outputs of the reference compass contain the EMI information, while the outputs of the other 2-D modules (e.g., those near the jaw of the user) include both EMI and tracer info. Because the EMI source is often far from the sensors, its magnetic flux can be considered uniform and unidirectional around all sensors. This field would create a "common mode signal" at the output of all sensors. The common mode signal can be eliminated by subtraction, after applying proper transformations that would take into account the difference between sensor orientations. Therefore, we can reliably relate different sensors' EMI components using linear coordinate transformation, as long as they do not move with respect to one another.

$$\begin{cases} X_L = a_{xL} X_E + b_{xL} Y_E + c_{xL} Z_E + d_{xL} \\ Z_L = a_{zL} X_E + b_{zL} Y_E + c_{zL} Z_E + d_{zL} \end{cases} \quad (1)$$

$$\begin{cases} X_R = a_{xR} X_E + b_{xR} Y_E + c_{xR} Z_E + d_{xR} \\ Z_R = a_{zR} X_E + b_{zR} Y_E + c_{zR} Z_E + d_{zR} \end{cases}$$

wherein ($X_L$, $Z_L$) and ($X_R$, $Z_R$) are the EMI components of the X and Z sensors on the left and right symmetrical 2-D modules, respectively, and $X_E$, $Y_E$, and $Z_E$ are the 3-D reference sensor outputs. The linear coefficients are a, b, c, and d, which can be determined by multi-linear regression algorithm. These linear coefficients stay constant as long as the relative position and orientation of the 3-D and 2-D modules is fixed.

Once the linear relationships between the reference compass and 2-D modules are setup and the EMI components of the 2-D modules are predicted, the outputs of each 2-D module can be subtracted by its associated value predicted by the reference compass. The result is a significant reduction in the EMI components of the 2-D sensors, while the tracer components are retained with minor changes. As a result, the effects of EMF and other sources of EMI are diminished and the signal-to-noise ratio (SNR) is increased.

Figure 14:
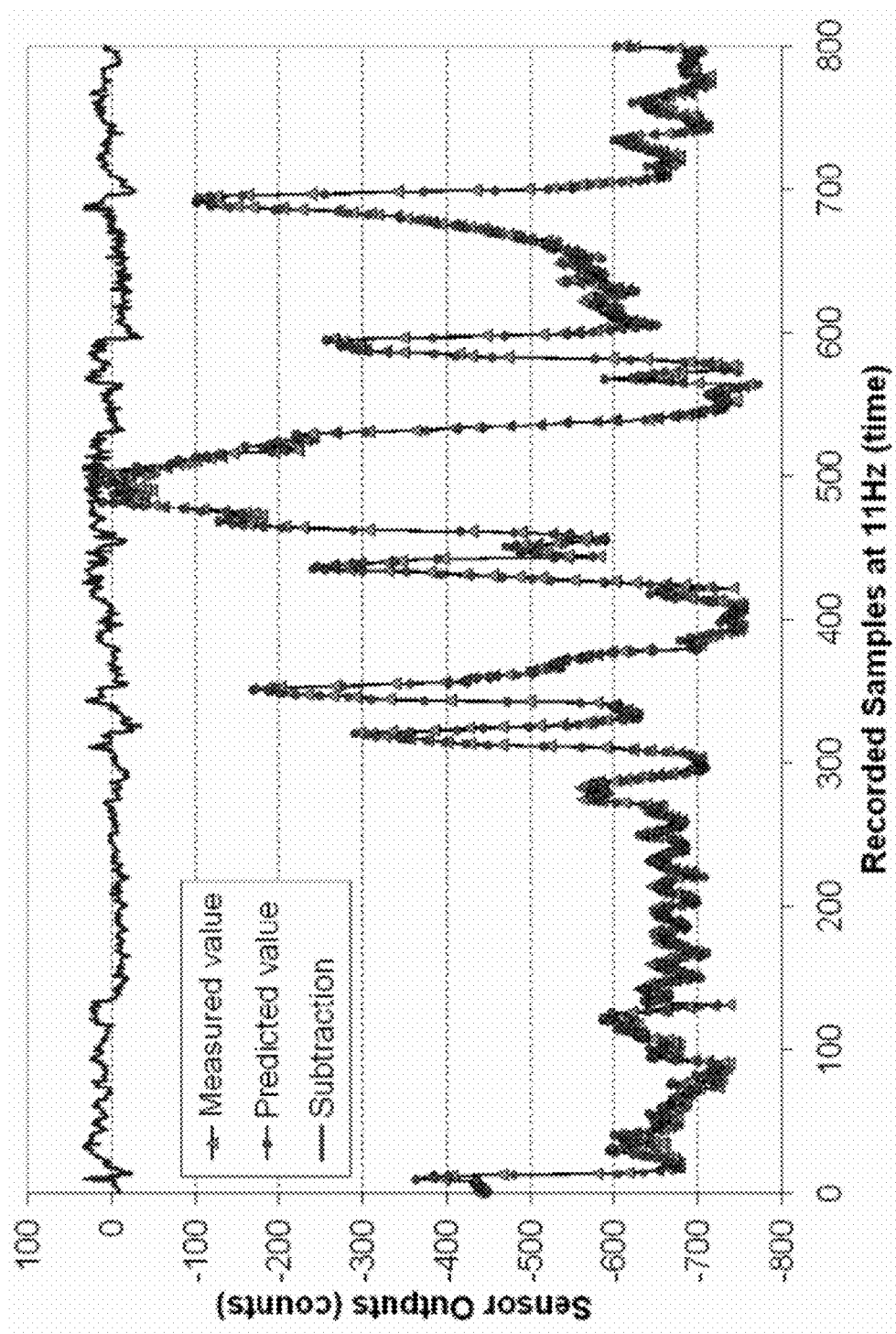
FIG. 14 is a graphical representation of measured output waveforms of a two-dimensional magnetic sensor (e.g., marked with triangles) and a predicted waveform based on linear transformation of the reference compass outputs (e.g., marked with circles), and subtraction of these two in order to remove the effects of external magnetic field variations (e.g., trace near top), in accordance with an exemplary embodiment of the present invention.

FIG. 14 graphically represents the measured output waveforms of a 2-D magnetic sensor (marked with triangles) and the predicted waveform based on linear transformation of the reference compass outputs (marked with circles), when the prototype is shifted and rotated in the lab without a nearby magnetic tracer. It can be seen that this algorithm can closely predict the EMI components at the 2-D sensor output and the subtracted signal is effectively free of EMI (the top most trace).

The SSP algorithm running on the processing system can be developed in the LabVIEW environment and includes two main parts: feature extraction and command classification.

1) Feature Extraction (FE):

The FE algorithm can be based on principal component analysis (PCA), which runs after a training session and during normal system operation. PCA can be implemented to reduce the dimensions of the incoming sensor data. This can result in a more efficient and less computationally intensive command classification process.

To better discriminate the tongue movements, increase the possible number of commands, and reduce the error rate in command classification, a sliding window of three acquired samples after EMI cancellation was considered. Increasing the size of this window could increase the classification accuracy at the cost of heavier computations. The computational load, however, can be limited especially when SSP runs on a PDA or smartphone. Therefore, it was important to reach a compromise.

During a training session, the user can associate a specific tongue movement or position to each command and repeat that command for a plurality of times, for example 10 times, by moving his/her tongue from its resting position after receiving a visual clue through a graphical user interface (GUI). Using this example, a total of 12 samples (three per sensor) can be recorded in 12-variable vectors for each repetition and labeled with the executed command. The FE algorithm can calculate the eigenvectors and eigenvalues of the covariance matrix in a 3-D space based on the training 12-variable vectors offline. Three eigenvectors with the largest eigenvalues (v1, v2, v3) are then chosen to make up the feature matrix, [v1, v2, v3]; this can mean extracting the most significant features of the sensor waveforms for each specific command.

Figure 15:
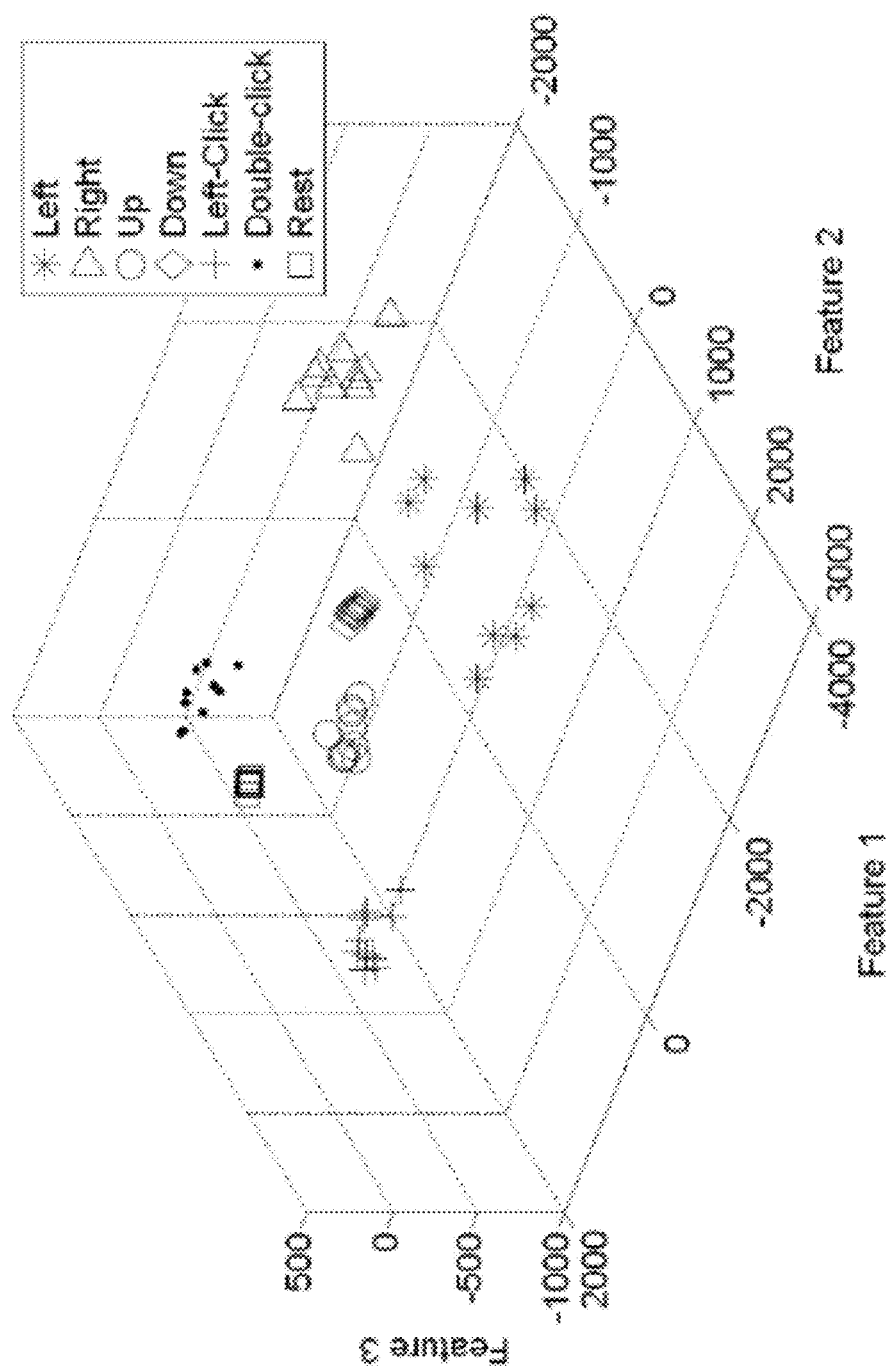
FIG. 15 is a graphical representation of data clusters representing different commands for the present system, in accordance with an exemplary embodiment of the present invention.

During the operation of the tongue drive system, compressed data vectors are produced from the raw sensor signals that come from the 3-sample sliding window using $$M = [v_1, v_2, v_3]^T \cdot M_0 \quad (2)$$

where $M_0$ is the 12 by 1 original data vector and M is the 3 by 1 compressed data vector. These compressed vectors have lower dimensions and therefore can be easier to classify. They contain the important features that help discriminating them from other commands when they form clusters in the virtual 3-D feature space, shown in FIG. 15.

2) Command Classification:

A K-nearest-neighbors (KNN) classifier can be used within the feature space to evaluate the proximity of the compressed incoming data points to the clusters formed during the training session. The KNN algorithm starts at the incoming new data point and inflates a spherical region until it contains K nearest training points. It associates the new data point to the command that has the majority of the training points inside that spherical region. After indication of the selected command, it will be executed by moving the mouse cursor on the screen or a mouse-click function at the cursor position. For the four movement commands, the cursor initially moves slowly to give the user finer control over. If the user, however, holds his/her tongue in a certain position, the cursor gradually moves faster until it reaches a maximum velocity.

The GUI works with the SSP to display the outputs. To facilitate command classification, the users can choose their tongue positions for different commands and also away from the mouth sagittal plane where most of the natural tongue movements occur. Even though not a command by itself, the first position is its resting position (i.e., null). Preferably, the other commands should be defined away from the tongue resting position.

Figure 16:
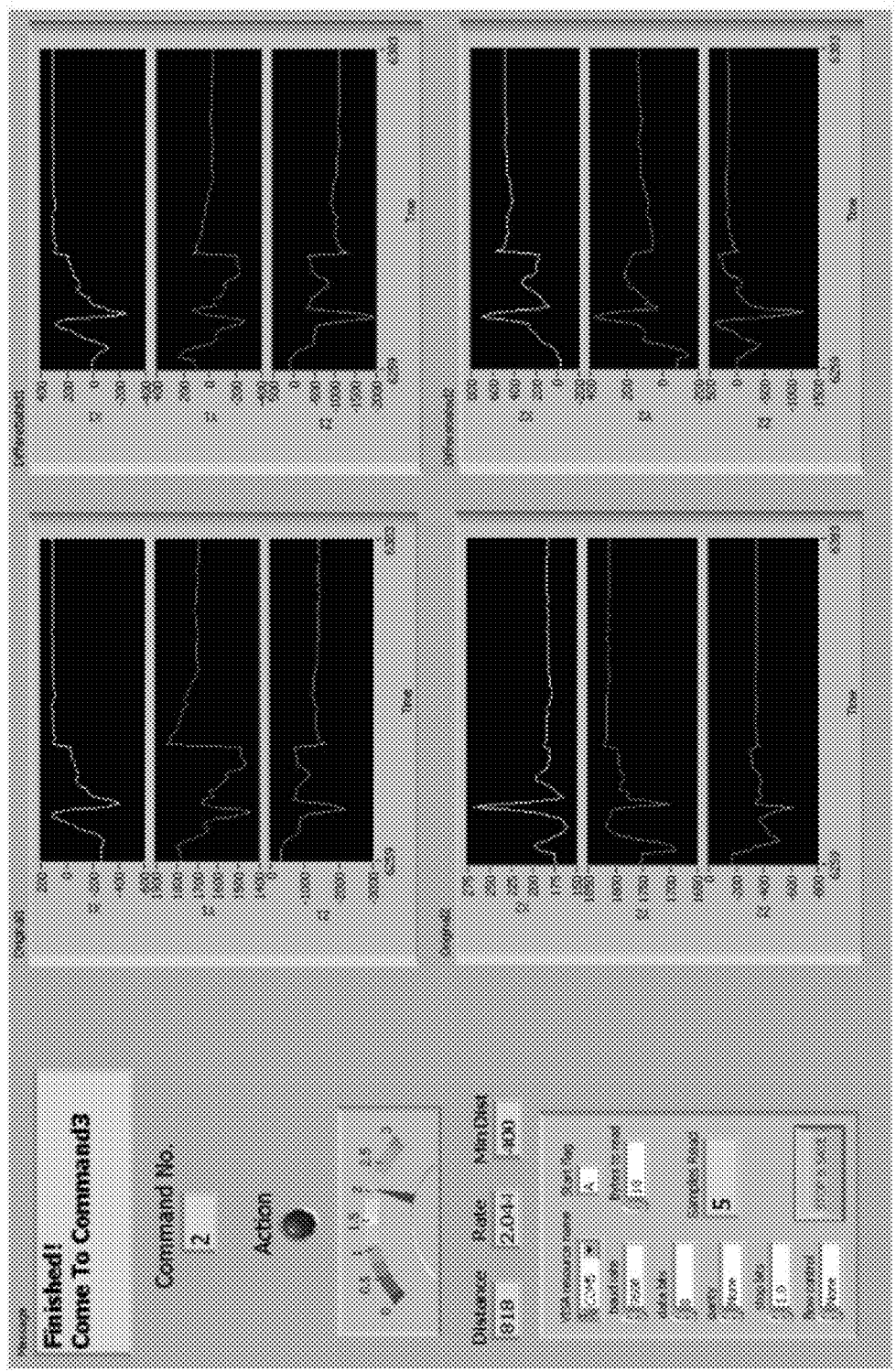
FIG. 16 is a view of a graphical user interface providing visual feedback of the tongue drive system for assisting users to find proper tongue positions and movement for different commands, in accordance with an exemplary embodiment of the present invention.

A visual feedback is included in the GUI in the form of displaying the tongue position in a virtual 3D mouth space, shown in FIG. 16. This GUI displays the "virtual position" of a magnet represented by a set of stars based on noise cancelled magnetic sensor output, in a virtual 3D mouth space. The stars move as the subject moves his/her tongue around. Therefore the positions of these stars in some senses reflect the positions of the magnet within subject's mouth. The subject may be asked to define each new command, such that the stars associated with that command are separated far enough from all other previously defined commands. Meanwhile, the subject may be asked to hold tongue stationary when defining a position for new command so that the points associated to that command in the virtual space converge to one point.

The command positions can then be saved and practiced for a few times to ensure that the user control of the command positions.

Figure 17:
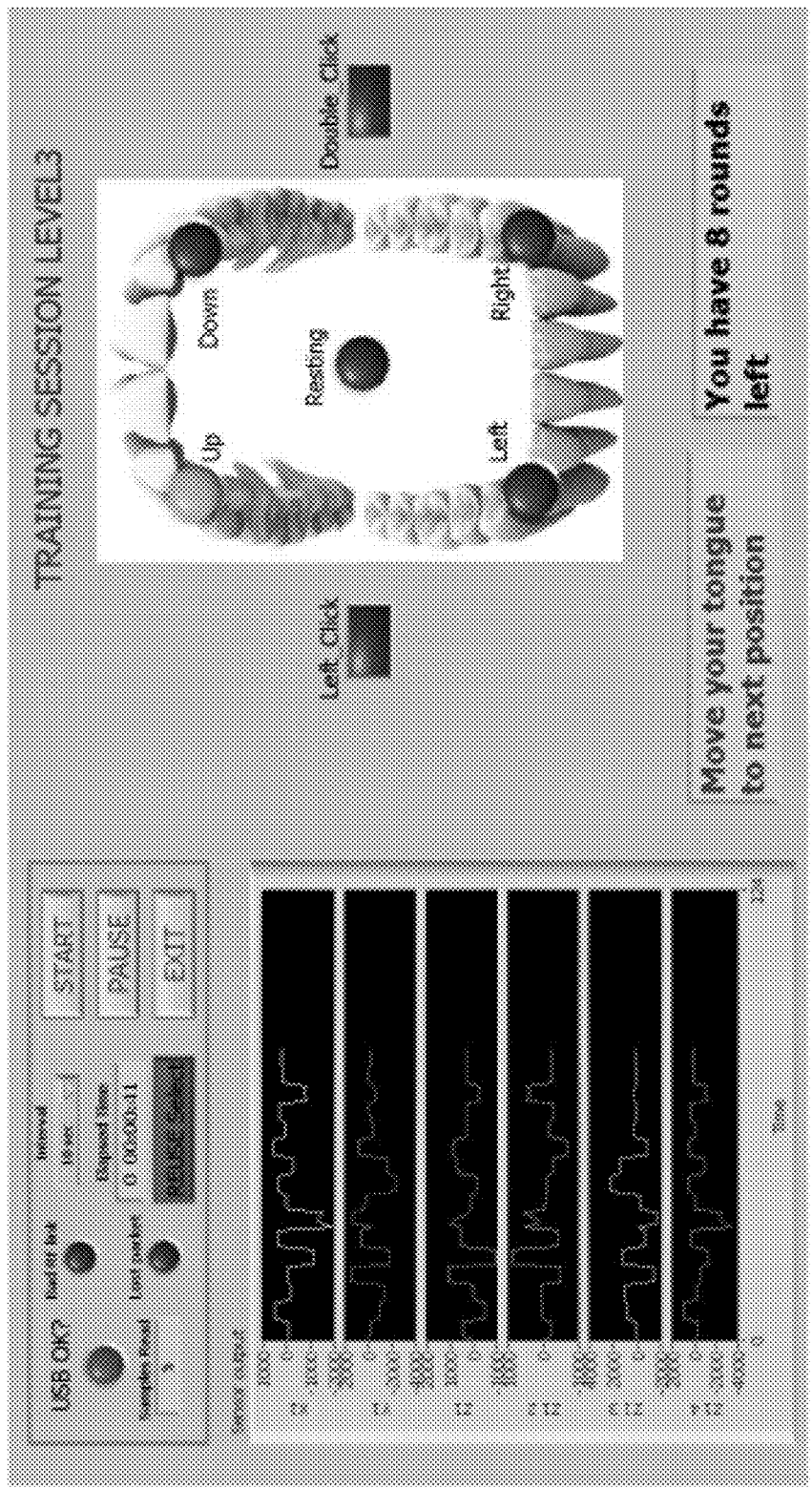
FIG. 17 is a view of a graphical user interface prompting a user to execute commands during a training command, in accordance with an exemplary embodiment of the present invention.

After the command-related tongue positions are defined and practiced, the user is ready to train the TDS. During the training session, the GUI, as depicted in FIG. 17, prompts the user to execute commands by turning on its associated indicator on the screen in certain intervals, e.g., three second intervals. The subject is prompted to issue a command by moving his/her tongue from its resting position to the corresponding command position when the command light is on, holding tongue stationary at that position when an auditory cue is playing, and then returning it back to the resting position when the light goes off. This procedure can be repeated, e.g., about 10 times, for the entire set of commands plus the tongue resting position. In an exemplary embodiment the result can be a total of about 70 training data points, which are processed offline to create the virtual feature space.

Figure 18:
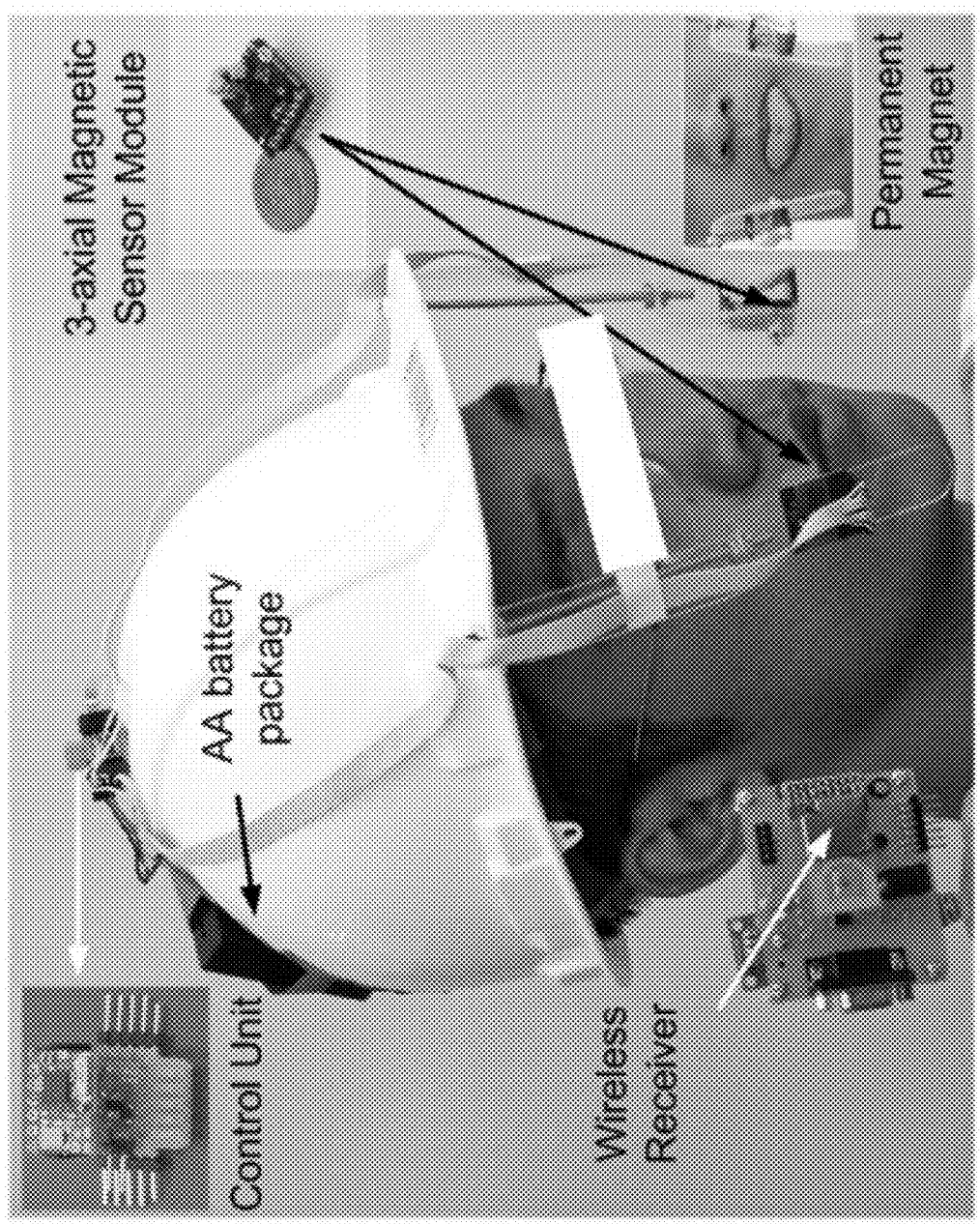
FIG. 18 is a perspective view of a hardhat carrying a tongue drive system, in accordance with an exemplary embodiment of the present invention.

In another embodiment, an external tongue drive system can use differential EMI cancellation, instead of using a three-dimensional reference compass to measure the EMI and subtract it from the sensor output as previously described. In a prototype, a pair of 3-axial magneto-inductive sensors can be mounted bilaterally on a hardhat, as shown exemplarily in FIG. 18, and thus implemented a new differential field cancellation algorithm to minimize the effect of EMI.

The outputs of each three-axial sensor module were transformed as if it was located at the position and orientation of the opposite module and subtracted from those outputs. As a result, the common-mode components in the sensor outputs, which were resulted from the EMI were cancelled out, while the differential-mode components resulted from the movements of the local magnetic tracer were retained and even magnified. The results were cancellation of the EMI and elimination of the reference module, which lead to additional power saving as well as a simpler and more compact TDS hardware.

Figure 19A:
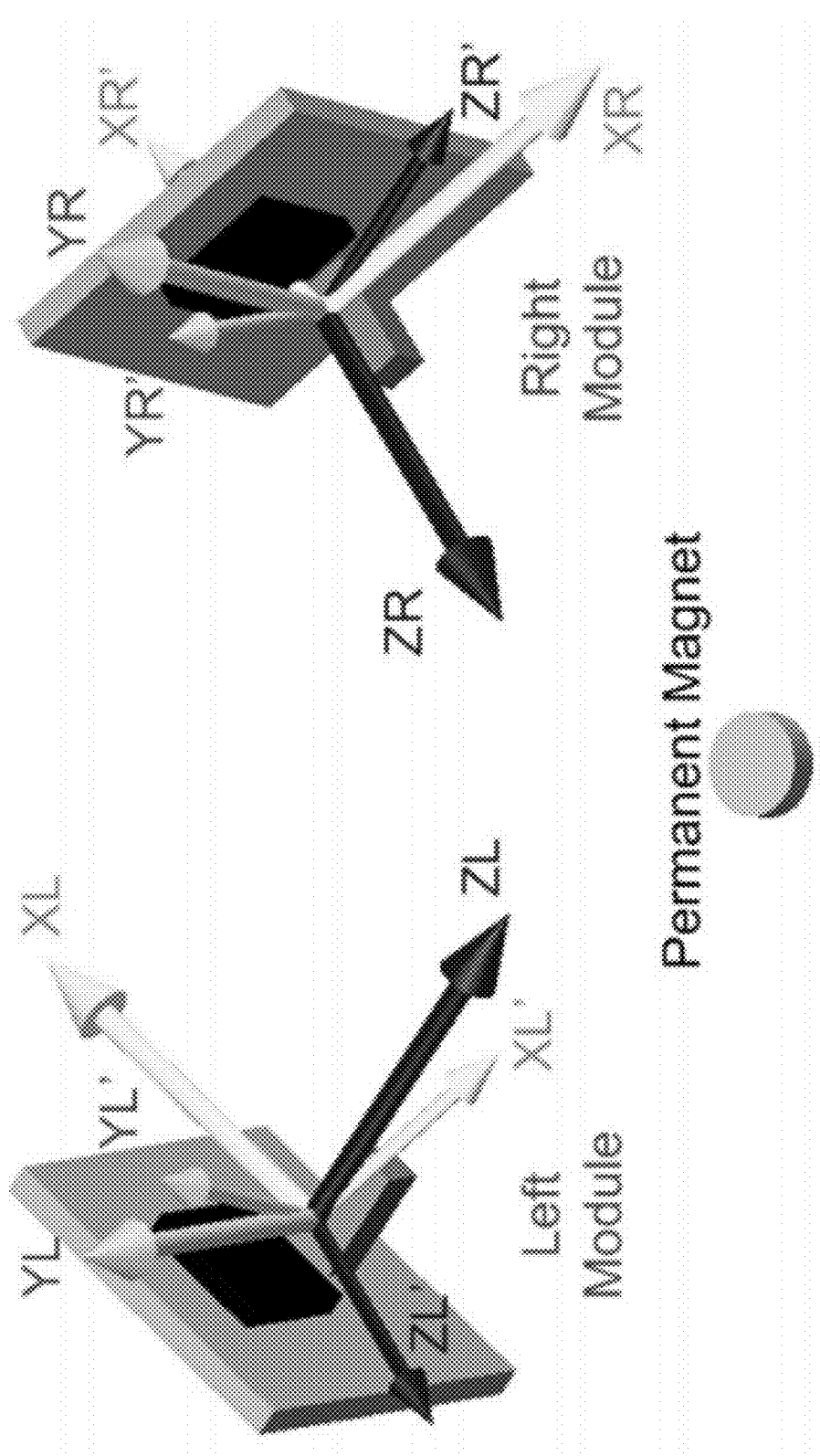
FIG. 19A illustrates relative position and orientation of three-axial sensor modules and the magnetic tracer attached to a user's tongue, where $X_L$, $Y_L$, and $Z_L$ are the three axes of the left module, and $X_R$, $Y_R$, and $Z_R$ are those of the right module, in accordance with an exemplary embodiment of the present invention.

FIG. 19A illustrates the relative position and orientation of the three-axial sensor modules and the magnetic tracer attached to the user's tongue, where $X_L$, $Y_L$ and $Z_L$ are the three axes of the left module, and $X_R$, $Y_R$ and $Z_R$ are those of the right module. Because the relative position and orientation of the two modules are fixed, based on coordinate transformation theory, we can mathematically rotate one of the modules and create a virtual module at the original location but parallel to the module on the opposite side $$\begin{bmatrix} X_L \\ Y_L \\ Z_L \end{bmatrix} = \mathfrak{R}_x(\theta_x) \cdot \mathfrak{R}_y(\theta_y) \cdot \mathfrak{R}_z(\theta_z) \cdot \begin{bmatrix} X_L \\ Y_L \\ Z_L \end{bmatrix} \quad (3)$$

where:

$$\mathfrak{R}_x(\theta_x) = \begin{bmatrix} 1 & 0 & 0 \\ 0 & \cos\theta_x & \sin\theta_x \\ 0 & -\sin\theta_x & \cos\theta_x \end{bmatrix},$$

$$\mathcal{H}_y(\theta_y) = \begin{bmatrix} \cos\theta_y & 0 & -\sin\theta_y \\ 0 & 1 & 0 \\ \sin\theta_y & 0 & \cos\theta_y \end{bmatrix},$$

$$\mathcal{H}_z(\theta_z) = \begin{bmatrix} \cos\theta_z & \sin\theta_z & 0 \\ -\sin\theta_z & \cos\theta_z & 0 \\ 1 & 0 & 1 \end{bmatrix}.$$

$\theta_x$, $\theta_y$, and $\theta_z$ are the rotation angles around the x, y, and z axes, respectively.

Because $\theta_x$, $\theta_y$, and $\theta_z$ are not known a priori and each sensor practically has a slightly different gain, we utilized a multi-linear regression algorithm to solve the linear coefficients in the following transformation equations which are derived from equation 3.

$$\begin{cases} X_L = a_{xL}X_L + b_{xL}Y_L + c_{xL}Z_L + d_{xL} \\ Y_L = a_{yL}X_L + b_{yL}Y_L + c_{yL}Z_L + d_{yL} \\ Z_L = a_{zL}X_L + b_{zL}Y_L + c_{zL}Z_L + d_{zL} \end{cases} \quad (4)$$

where a, b, c and d are the linear coefficients, which imply the relative orientations and gain differences between the two sensor modules, can be found by multi-linear regression algorithm.

Once the linear relationship between the two modules is setup, EMI source, which may be far from the sensors, can result in equal outputs among each module and its virtual replica on the opposite side. On the other hand, the sensor outputs resulted from the movements of the strong nearby magnetic tracer on the tongue can be different unless the magnet moves along the symmetrical plane between the two modules (e.g., along the sagittal plane). Therefore, by subtracting the outputs of each module (i.e., $Z_R$) from its associated virtual module (i.e. $Z_L'$), the EMI components can be canceled out or significantly diminished, while the tracer components can be amplified. As a result, the effects of EMI are minimized and the SNR is greatly improved.

Figure 19B:
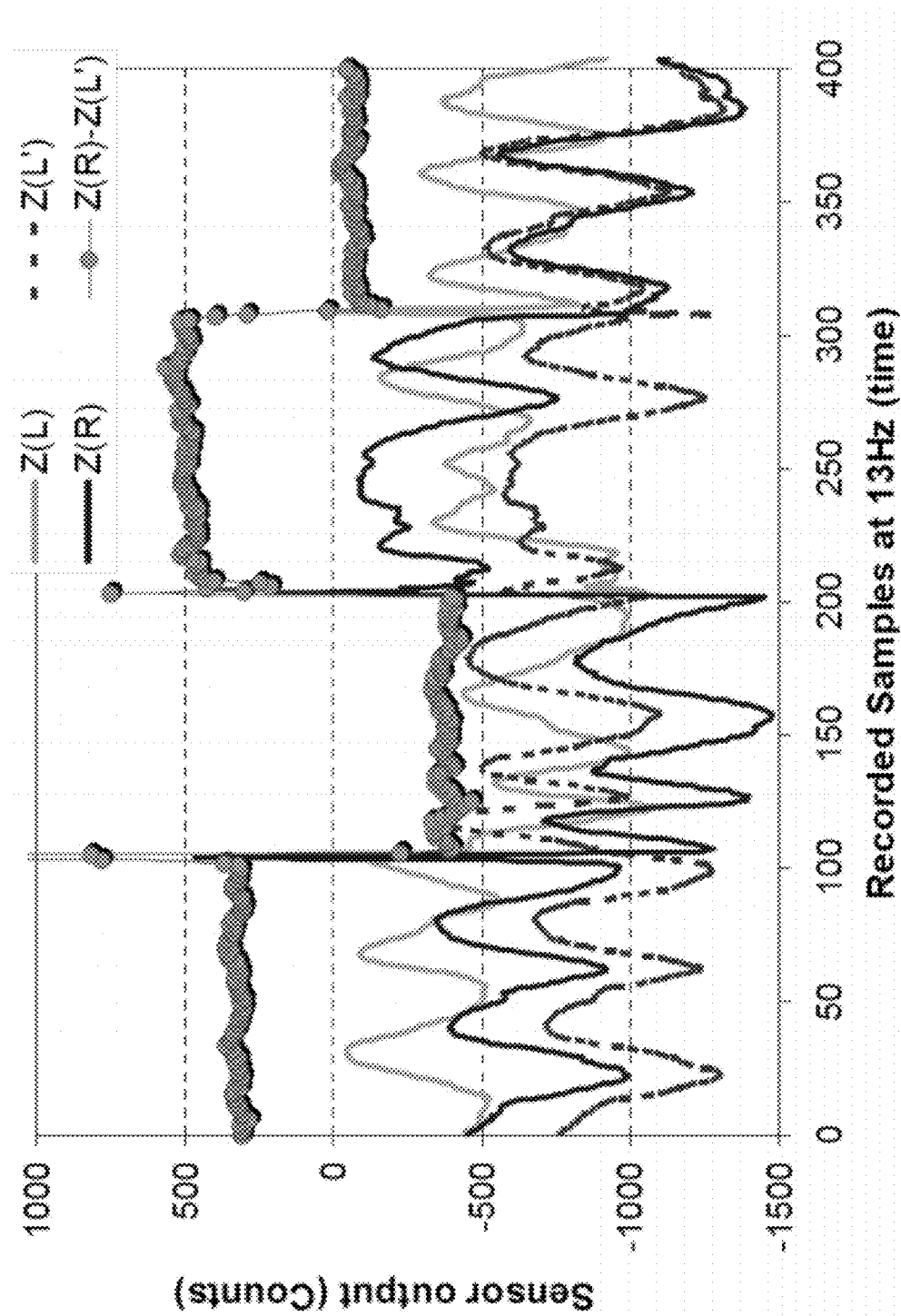
FIG. 19B is a graphical representation of exemplary output waveforms of the $Z_L$ and $Z_R$ sensors on the left and right module, respectively, the transformed $Z_L'$, as well as the differential result of $Z_R-Z_L'$ when a user, wearing a prototype tongue drive system, issues two left mouse commands while walking, in accordance with an exemplary embodiment of the present invention.

FIG. 19B illustrates a graphical representation of output waveforms of the $Z_L$ and $Z_R$ sensors on the left and right module, respectively, the transformed $Z_L'$, as well as the differential result of $Z_R$-$Z_L'$ when the user, wearing the prototype TDS, issues two left mouse commands while walking in the lab. The differential signal is cleaner and effectively free of EMI. Therefore, detecting and identifying the user command is made easier.

The SSP algorithm of this prototype can also be based on PCA and KNN. The SSP algorithm combines six differential outputs of the three samples to build an 18-variable data point. The key features of each data point can then be extracted by the PCA and reflected as a new sample onto a virtual 3-D space. The KNN algorithm classifies the incoming samples and associates them to particular commands that are defined during the training session.

In this system, the wireless receiver can be connected to the processing system, preferably, through a USB port instead of RS-232 port to make the connection compatible with a PDA or smartphone with USB port. The same visual feedback and training GUIs can also be used for this system.

In an exemplary embodiment, the tongue drive system is adapted to drive a powered wheelchair. Accordingly, in some embodiments, the system and apparatus includes a powered wheelchair interface (PWI).

As mentioned, the control commands generated by tongue drive system can be used to either access a computer or control the devices and equipments in user's environment such as a powered wheelchair (PWC). When the TDS is interfaced with a PWC, a laptop can replace the processing system (e.g., PC) to perform the sensor signal processing and transmit the command(s) to operate the PWC through interface circuitry. A function of interface circuitry is to convert the digital control commands translated by laptop to the compatible waveforms which can be recognized by PWC controller.

There are many approaches to link the external TDS prototype with a PWC, including a wired approach and a wireless approach.

Figure 20A:
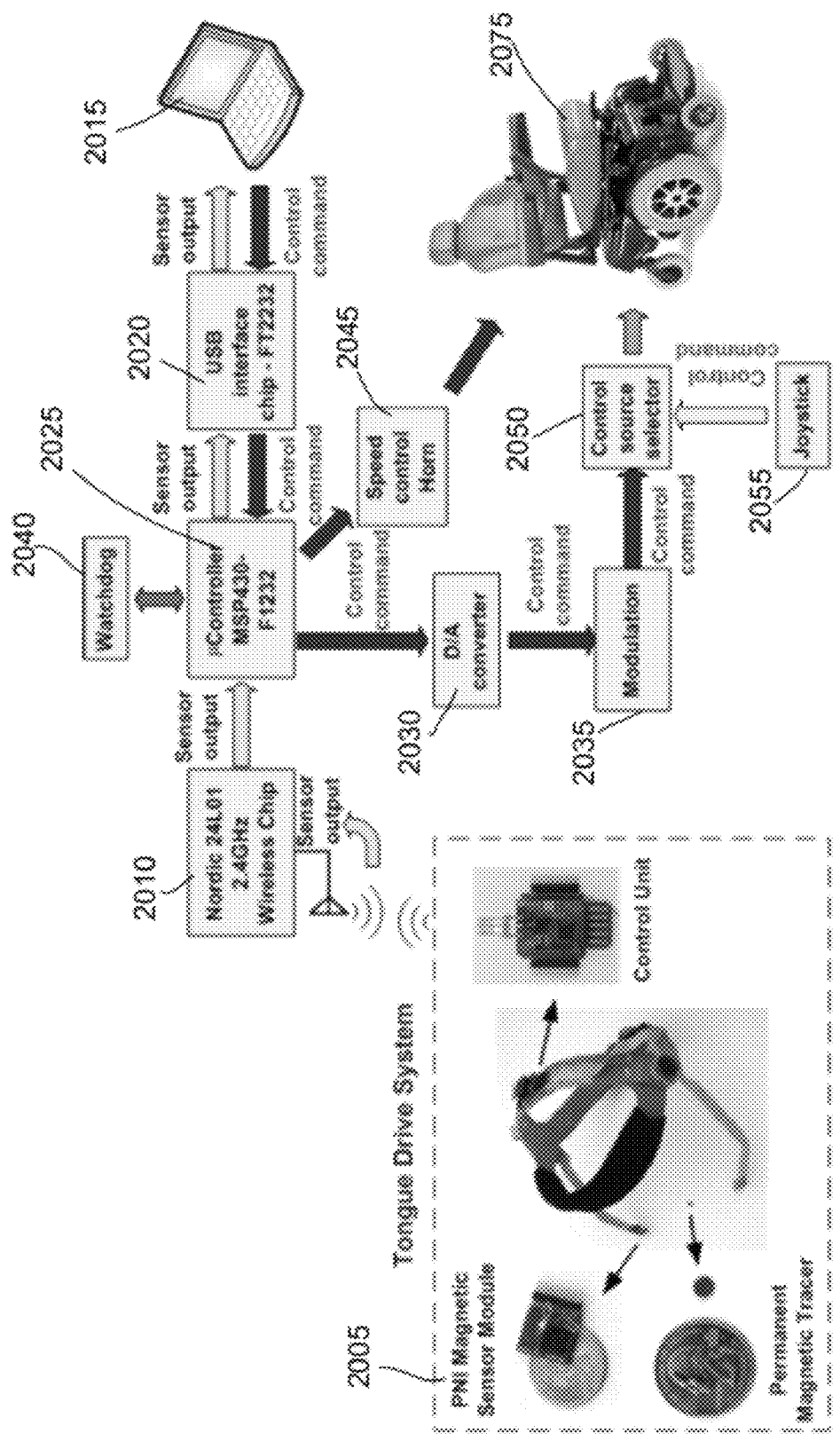
FIG. 20A is a block diagram of a wired tongue drive system-powered wheelchair interface, in accordance with an exemplary embodiment of the present invention.

In an exemplary embodiment, the wired approach may be implemented via a USB-based system. In this approach, the TDS-PWC interface circuitry can include a low power microcontroller, USB interface circuitry, watchdog, digital-to-analog converter (DAC), and control signal modulation circuitry combined with a wireless receiver, and connected to laptop through USB port (see FIG. 20A). The sensor outputs can be wirelessly transmitted by the TDS device 2005 to be captured by the receiver 2010, and forwarded to laptop 2015 for processing. After the SSP, which can operate on the laptop, has interpreted the user commands, the commands are sent back to the receiver through the same USB-connection 2020. An ultra low power microcontroller 2025 can drive an DAC 2030 (e.g., off-the-shelf) to convert the digital control commands from laptop 2015 to multi-channel analog signals. These analog signals can then be modulated by analog multiplexers 2035 to generate a set of rectangular waveforms which can emulate and replace the input signals from a traditional joystick to control the PWC 2075.

Some important features of this approach include:
A low power microcontroller (MCU) (e.g., MSP430F1232) can be responsible for generating the final control signal to operate the PWC 2075. The laptop does not directly access control of the PWC 2075. Therefore, in case the laptop is in standby mode and the MCU can not receive the correct commands, the MCU can zero all control signals to stop the PWC.

A local emergency stop command can be issued by the user, which can be directly recognized by the MCU 2025 to stop the PWC 2075 without passing through the SSP in laptop. Therefore, the PWC can be quickly stopped by issuing a dedicated emergency stop command to avoid accidents, for example and not limitation, when some unexpected problems happen in the SSP running in the laptop.

A watchdog integrated circuit chip 2040 can be added to reset the MCU 2025 in case the MCU 2025 itself runs out of work.

In addition to the movement control, the user also has access to the speed level adjustment and horning 2045.

A control source selector about 2050 allows user to choose the TDS 2005 or a joystick 2055 as the input device to control the PWC 2075. This provides a backup control method for the user who has some hand functions to temporarily operate the PWC 2075 using his/her hand in case the TDS system is out of order.

Figure 20B:
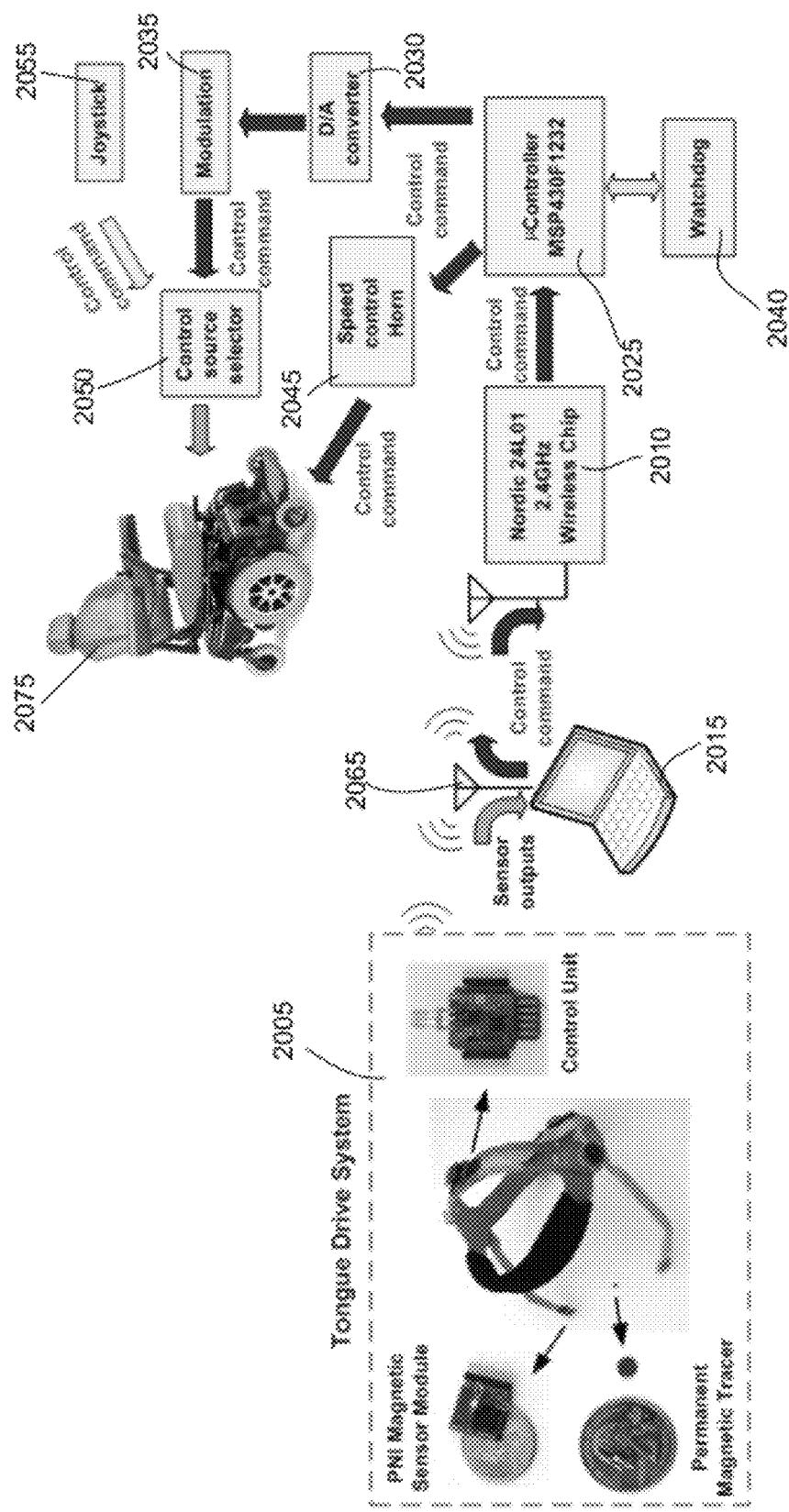
FIG. 20B is a block diagram of a wireless tongue drive system powered wheelchair interface, in accordance with an exemplary embodiment of the present invention.

In an alternative approach, i.e., the wireless approach, the USB wireless receiver on laptop side can be split into at least two parts, one of which is a dedicated wireless transceiver with USB interface to communicate with laptop and the other of which is a wireless receiver without USB connection combined with the interface circuitry and sitting at PWC side, as illustrated in FIG. 20B. The wireless transceiver 2065 can be connected to the laptop 2015 and thus firstly configured as a receiver. The wireless transceiver 2065 can receive the sensor outputs from the system 2005 and forward them to laptop 2015 for processing. After the laptop 2015 extracts the command(s) from this data, the same transceiver 2065 can be configured as a transmitter and wirelessly send out the control command at a different frequency to the PWC 2075 side receiver. On the PWC 2075 side, if a valid control command is received, the local MCU 2025 can start the same process as explained in previous approach to convert the command to a set of square waveform to control the PWC.

In this configuration, the TDS 2005 transmitter can bypass the laptop 2015 side receiver and directly transmit a local emergency stop command to the PWI circuit by properly setting transmission frequency and address. Therefore, even if the laptop 2015 is shut down or switched to standby mode, the control circuit can still stop the PWC when it detects the emergency command from TDS directly.

A potential benefit of this approach is that any devices in user's environment, as long as they are equipped with customized receiver and control circuit, can be controlled by the user using his/her tongue movement and TDS.

Figure 21:
FIG. 21 illustrates an exemplary tongue drive system prototype worn by an able-bodied subject to control a powered wheelchair, in accordance with an exemplary embodiment of the present invention.

As shown in FIG. 21, the TDS-PWC interface, which includes adapter circuitry and a GUI, adapted to operate on a laptop, has been developed to link a new external TDS prototype built on a headgear with, for example, an Alero-GP52 commercial PWC (e.g., Golden Technologies, Old Forge, Pa.). The adapter circuitry, depicted in the FIG. 21 inset, can receive control commands from the laptop, e.g., through a USB port, and converts them into rectangular waveforms (about four) that can be compatible with the VR2 motor drive controller (e.g., PG Drives Technology, Anaheim, Calif.).

Figure 22B:
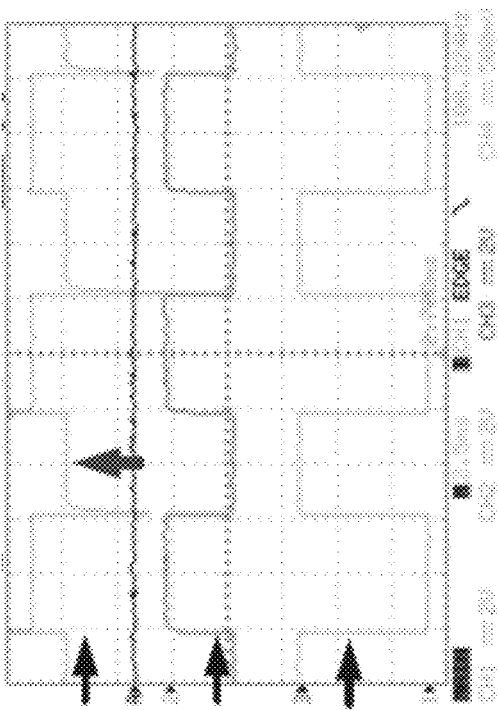
FIG. 22B is a graphical representation of a waveform of control signals generated by interface circuitry when the negative level of a control signal moves up when forward movement commands are issued, in accordance with an exemplary embodiment of the present invention.
Figure 22A:
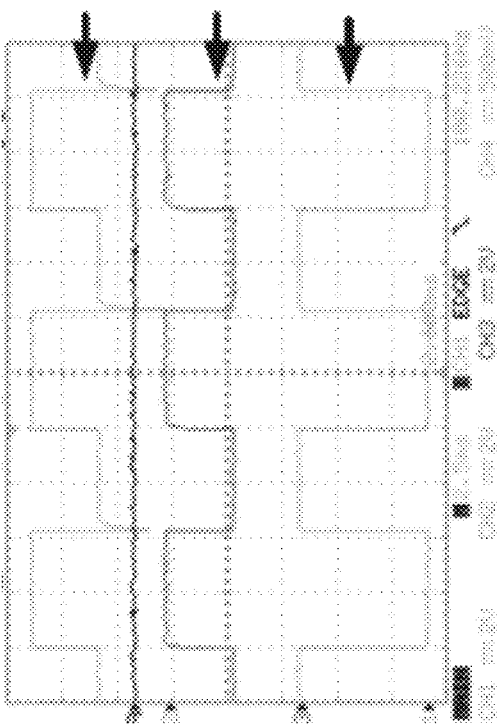
FIG. 22A is a graphical representation of a waveform of control signals generated by interface circuitry when a wheelchair is stationary while the control signal is resemble to the reference signal, in accordance with an exemplary embodiment of the present invention.
Figure 23:
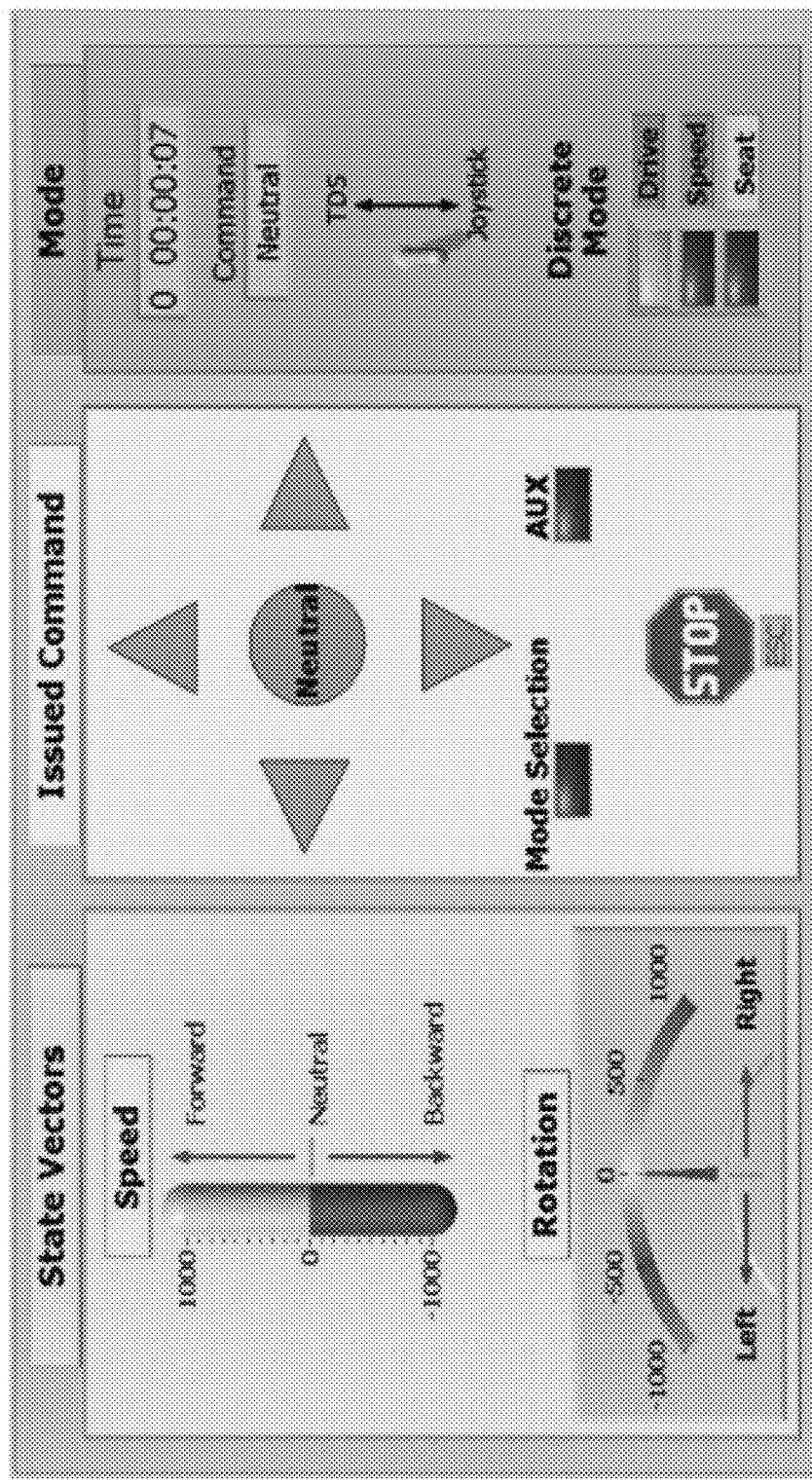
FIG. 23 illustrates a graphical user interface for powered wheelchair control, which provides a user with visual feedback on a current powered wheelchair movement, direction and speed, as well as feedback on a gear-shift system for a powered wheelchair control strategy, in accordance with an exemplary embodiment of the present invention.

FIGS. 22A-22B show graphical representations of the rectangular waveforms that substitute the inputs that VR2 can receive from its proportional joystick. The direction and speed of the PWC can be controlled by adjusting the lower level amplitudes of these rectangular waveforms. The GUI, shown in FIG. 23, provides the user with a visual feedback on the selected command, current direction and speed of the wheelchair, and the total operational time. A technician can fine tune the knobs located at the bottom of the GUI to compensate the slight deviations to the left or right during forward and backward movements of the wheelchair that are resulted from the inherent speed misalignment between left- and right-wheel. Watching the GUI, however, is not necessary during PWC operation. Hence, the laptop which also runs the SSP algorithm in the background can be hidden beneath the PWC seat, as shown in FIG. 21.

Considering there are some sorts of differences between tongue-based and hand-based PWC operation, at least three exemplary candidate control strategies can be implemented for TDS-based PWC control by compromising the safety, agility, convenience, and comfort issues. A user can select any of them based on their own preferences.

A first exemplary control strategy, known as discrete control, is the control with mutually exclusive commands. In this control strategy, a predetermined number of commands can control movement. In an exemplary embodiment, five commands out of a total of seven that are available in the TDS can be used to control the PWC movements: FORWARD, BACK, RIGHT, LEFT, and NEUTRAL. The last one, i.e., NEUTRAL, is issued when the tongue is in resting position (e.g., null), and returns the PWC to stationary state. At least two state vectors have been defined for linear movement (V_L) and rotation (V_A) respectively. The PWC linear and rotation speeds can be proportional to the state vector values. Positive V_L vector means the PWC is moving forward, while the negative V_L vector gives the PWC a backward speed. The larger V_L absolute value the faster PWC moves and the same strategy is applicable for rotation. Positive V_A can represent a right turn and the negative value can represent a left turn. The speed of rotation can be proportional to the absolute value of V_A. The definitions of five different control commands are as follows:

FORWARD: linear vector (V_L)++.
BACKWARD: linear vector (V_L)--.
RIGHT: rotation vector (V_A)++.
LEFT: rotation vector (V_A)--.
NEUTRAL: zero both linear and rotation vectors.

In some embodiments, new TDS commands can increase/decrease its relevant state vector by a fixed amount until a predefined maximum speed is reached in that direction. In some embodiments, if the user keeps issuing the same command, the PWC linearly accelerates and reaches the maximum speed in that direction. The NEUTRAL command, on the other hand, linearly decreases/increases the state vectors from a given direction to zero. By returning the tongue to its resting position, one can gradually bring the PWC to a standstill. Vector maximum levels and rate of change can be adjusted for each user.

State vectors are mutually exclusive, i.e., only one state vector can be non-zero at any time. If a new command changes the current state, for example from forward to left, the previous state vector has to be gradually returned to zero before the new vector can start changing. In an exemplary embodiment, the user may not change the PWC moving direction before stopping. This is a safety feature at the cost of slowing down the PWC maneuverability. Exemplarily, the speed of returning previous vector to zero is set to be five times faster than the increase/decrease speed of the following vector. The user can still quickly stop the wheelchair and switch to another movement state with minimum delay.

A second exemplary control strategy is to continuously control the system. In this strategy, the same vectors are defined and the speeds of the PWC are still proportional to these state vectors. The definitions, however, of five different control commands are slightly different:

FORWARD: linear vector (V_L)++.
BACKWARD: linear vector (V_L)--.
RIGHT: rotation vector (V_A)++.
LEFT: rotation vector (V_A)--.
NEUTRAL: zero the rotation vector while keep the current linear vector.

An exemplary modification versus is the function of NEUTRAL command. In the previously described control strategy (i.e., discrete control), the PWC can be brought back to stationary if the users moves their tongues back to resting position. In this strategy, however, the NEUTRAL command can reset the rotation speed to zero while leaving the linear movement speed as is. With this modification, the users do not have to hold their tongues at certain positions to maintain the speed but can return their tongues back to resting position for their maximum comfort after the wheelchair is accelerated to a certain speed. The wheelchair will keep moving in that speed until users issue a BACKWARD command to decrease the speed. As a result, the users' tongue is at its resting position for most of the time and it is more comfortable for long time usage.

Additionally, the vectors are no longer mutually exclusive, e.g., two vectors can be set to non-zero at same time. Consequently, the PWC can be steered when it is moving forward or backward. When the PWC is rotating, the forward/backward movement speed can also be adjusted. The wheelchair movement can be smoother and a curve track is possible under this strategy.

Another difference is the nonlinearity of movement and rotation gradient. This means that the increasing or decreasing steps of speed and rotation are not fixed, but increased over time. In other words, when user issues a command, the speed of movement/rotation changes slowly at the beginning and this change gradually becomes more dramatic if the user keeps issuing the same command. This function is useful when users not only want to fine tune the forward/backward movement speed but also need to stop the PWC in a short time. The users can make small movement or rotation adjustments by touching their tongues at command position for a short period. Users can also continuously issue the same commands for start, stop or rotate the PWC quickly.

A third exemplary control strategy is continuous control with gear shifting functionality. This type of control strategy can emulate the intuitive control of an able-bodied person when driving a car. By using an additional command, the gear shifting function can be introduced into the PWC control. Here, users can shift the gears to operate the PWC at different speed levels. Five different gears can be included in this strategy and explained below:

- N: Neutral. When the gear is in this position, the wheelchair keeps stationary no matter what movement commands are given, just like the Neutral position of a car.
- 1: First gear. The low speed level for indoor or crowd environment operation.
- 2: Second gear. The medium speed level for normal operation.
- 3: Third gear. The high speed level for outdoor operation.
- R: Reverse. Level for backup movement.

By holding the users' tongues at a pre-trained position for one second, users can issue a gear shifting command to shift the gear from N to R and then back to N. In some embodiments, users may have to stop the PWC before issuing a gear shift command.

Figure 24:
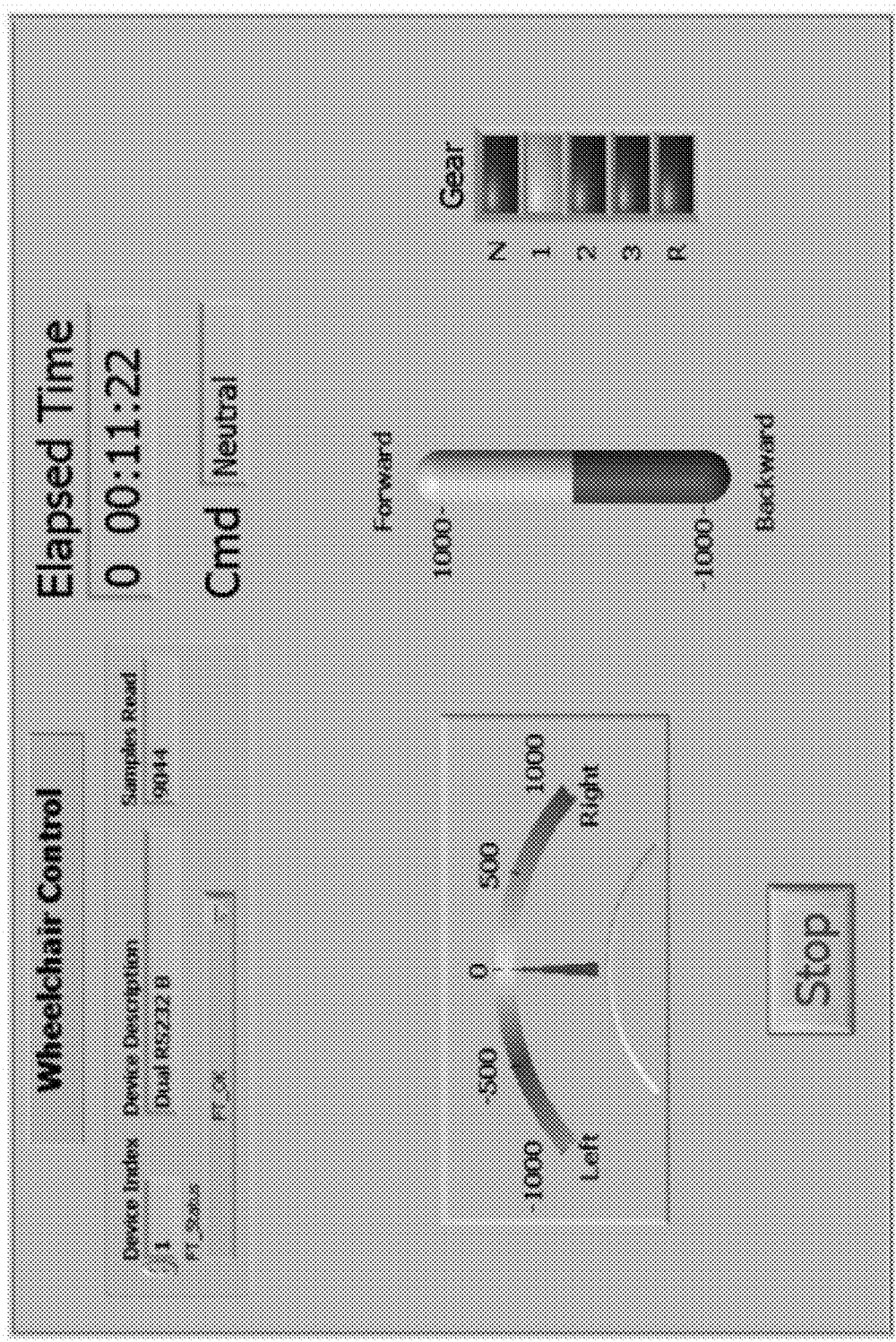
FIG. 24 illustrates a graphical user interface for powered wheelchair control, which provides a user with visual feedback on a gear-shift system for a powered wheelchair control strategy, in accordance with an exemplary embodiment of the present invention.

For example, another GUI, shown in FIG. 24, was tailored for this control strategy. In addition to showing the issued command and the current wheelchair movement states, the GUI further indicates the current speed level by turning on the relevant light on the screen. The indication can be implemented in hardware using a plurality of LEDs (e.g., five) sitting in the front panel of PWC controller. In that way, users can receive the feedback from the front panel of PWC controller and do not need to look at the computer screen.

The definitions of the commands are also slightly different:
- ACCELERATION: absolute value of linear vector ($|V\_L|$)++.
- BRAKE: absolute value of linear vector ($|V\_L|$) and rotation vector ($|V\_A|$)--.
- RIGHT: rotation vector ($V\_A$)++.
- LEFT: rotation vector ($V\_A$)--.
- NEUTRAL: zero the rotation vector while keep the current linear vector.
- GEAR SHIFT: Shift the gear from N to R and then back to N.

Because a reverse function can be included in the gear box, two linear movement control commands may affect the absolute value of $V\_L$ and are defined as acceleration and brake. The sign of $V\_L$ can be determined by the gear level. The $V\_L$ is about zero when the gear level is N; and $V\_L$ is negative if the gear level is R. Otherwise, $V\_L$ is positive. As a result, when users issue an acceleration command, the speed of PWC increases nonlinearly (similar to previous strategy) to a maximum value depending on which gear is selected. If R gear is selected, the maximum speed is set internally to be the same as level 1 and the acceleration command increases the backup speed. The brake command decreases both linear and angular speed to zero. The LEFT, RIGHT, NEUTRAL commands are same as those defined in previous strategy.

Tongue Drive System Examples

The following is another non-limiting example of the tongue drive system.

To minimize the training efforts and learning curve in human experiments, we decided to substitute the mouse computer input with the TDS prototype. A user familiar with operating a mouse in Windows operating system could directly use the TDS. We defined six individual commands in the TDS prototype GUI for up, down, left, and right cursor movements as well as single- and double-click functions.

Detailed human trial instructions were prepared ahead of the experiments, discussed with the subjects, and strictly followed to ensure that every subject follows the same procedure. A permanent magnet was disinfected using 70% isopropyl rubbing alcohol, dried, and attached to the subject's tongue, about one centimeter from its tip, using cyanoacrylic tissue adhesives (e.g., Cyanodent, Ellman International Inc., Oceanside, N.Y.). Drying the subject's tongue ahead of the tracer attachment could result in a better adhesion, but was not necessary. The subject then wore the external TDS prototype, and was allowed to familiarize himself/herself with the TDS and magnet on his/her tongue for up to about 15 minutes.

The subjects were then asked to search for the proper tongue positions for different commands with the assistant of visual feedback GUI. After all proper tongue positions have been found and practiced, the subjects were then instructed to go through the training session to define the control commands according the procedure explained in section 5.1 part D. Next, the subjects were required to complete following non-limiting tasks.

Test I: Percentage of Correctly Completed Commands Vs. Response Time

This test was designed to measure the TDS response time, which includes thinking about the command and its associated tongue movement, physical tongue movement transients, sampling the magnetic field variations, wireless transmission of the acquired samples, and the SSP computation delays. The shorter the response time is the better. It is not only important to issue commands quickly but also to detect them correctly and accurately. Consequently, we also considered the percentage of correctly completed commands (CCC %) along with the response time.

Figure 25:
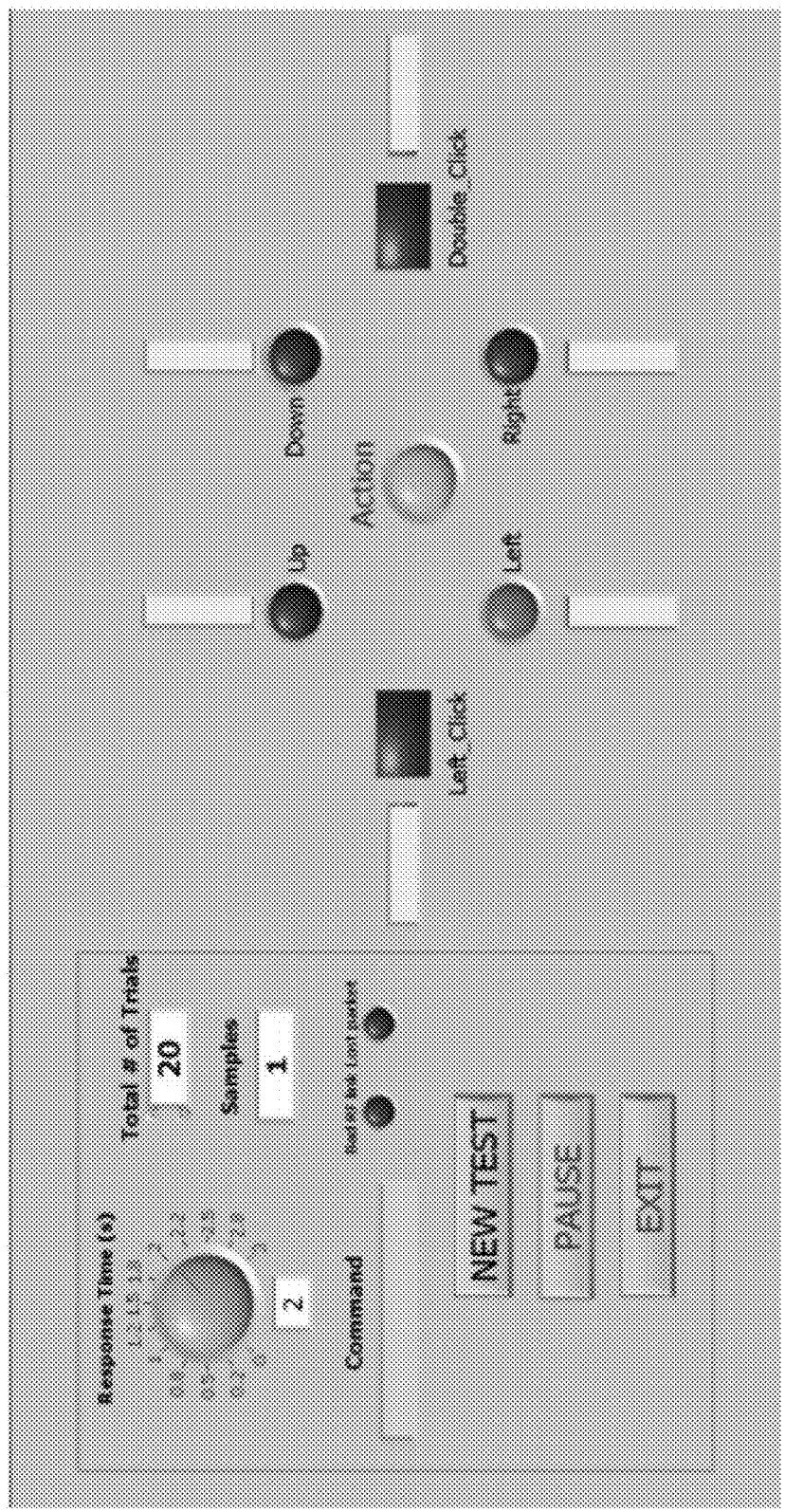
FIG. 25 illustrates a graphical user interface of the tongue drive control response time measurement, in accordance with an exemplary embodiment of the present invention.

Another GUI, shown in FIG. 25, was developed for this experiment to randomly select one out of six direct commands and turn its indicator on. The subject was asked to issue the indicated command within a specified time period T, while the "action" light was on, by moving his/her tongue from its resting position the same way that he/she had trained the TDS for that particular command. The GUI also provided the subject with real time visual feedback by changing the size of a bar associated to each command, which indicated how close the subject's tongue was to the position of that specific command. After about 40 trials at every time T=2, 1.5, 1, 0.8, and 0.6 s, in the order of larger to smaller periods, test results were generated by calculating the CCC % for each time period T.

Because the function and purpose of the TDS is similar to a BCI device, with the advantage of being minimally invasive, we can use some of the same figures of merit that are used to evaluate and compare the BCIs. One of these measures, known as information transfer rate (ITR), describes how much useful information the system can transfer from the user to a computer within a certain period of time. Various researchers have defined the ITR differently. We have calculated the ITR using Wolpaw's definition, $$ITR = \frac{1}{t}\left(\log_2 N + P\log_2 P + (1-P)\log_2 \frac{1-P}{N-1}\right) \quad (5)$$

where N is the number of individual commands that the system can issue, P=CCC % is the system accuracy, and T is the system response time in seconds or minutes. The advantage of this definition is that it takes into account many BCI parameters.

Figure 26A:
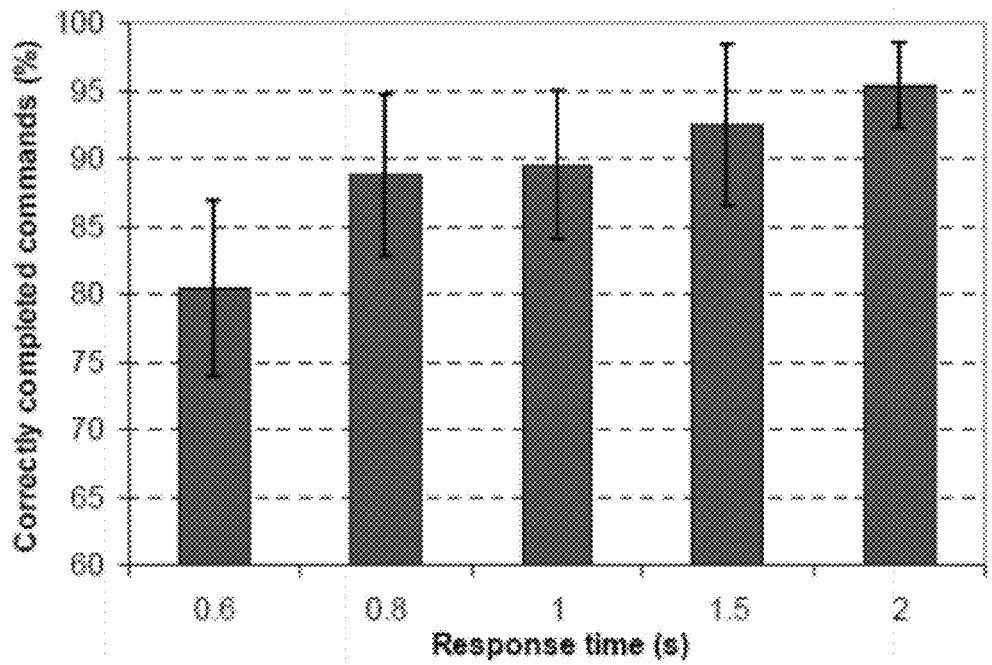
FIG. 26A is a graphical representation of a relationship between the percentage of correctly completed commands and the tongue system response time obtained from six exemplary human trials, in accordance with an exemplary embodiment of the present invention.
Figure 26B:
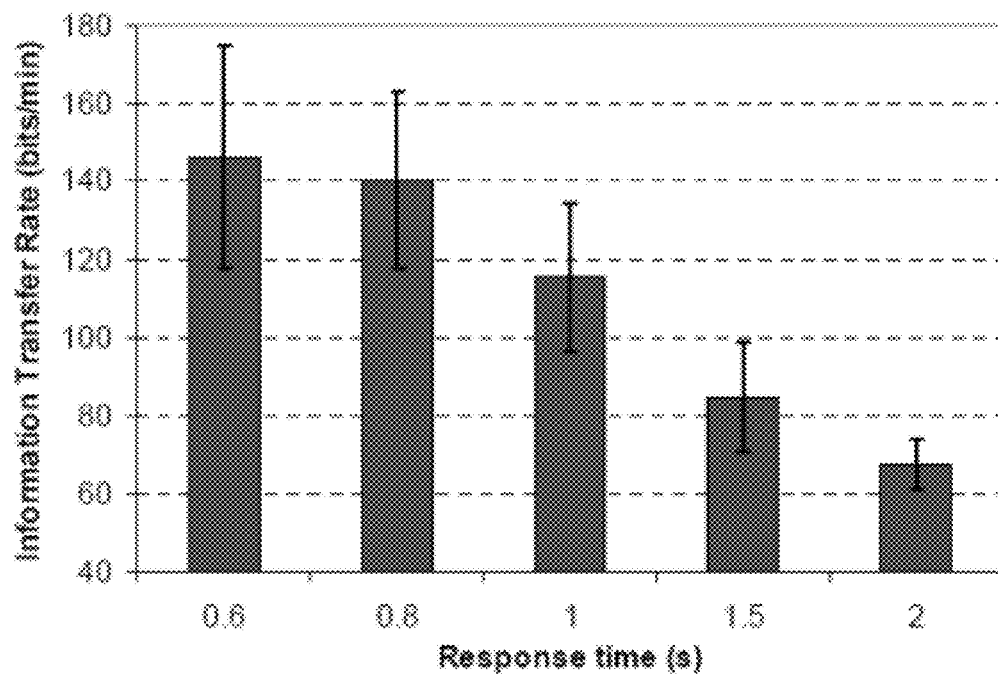
FIG. 26B is a graphical representation of a relation between the tongue drive system information transfer rate and the response time obtained from six exemplary human trials, in accordance with an exemplary embodiment of the present invention.

FIG. 26A shows a graphical representation of the average CCC % vs. response time for all six subjects. It can be seen that an average performance for a TDS beginner with CCC %>80% can be achieved with T≧0.6 s. FIG. 26B shows a graphical representation of the mean value and 95% confidence interval of the corresponding information transfer rate (ITR) for different response times. The highest ITR, which was achieved at T=0.6 s, can result from very short response time and moderate CCC %. For higher T, the ITR drops due to the slower response time of the system and less significant increments in CCC %. Nevertheless, from practical point of view, a good performance with CCC %≈90% can be obtained when T≧0.8 s, yielding an ITR of about 140 bits/min.

The preliminary results with the current prototype are already better than most BCIs and TCIs. Table IV compared the ITR achieved by present TDS prototype with other TCIs and BCIs.

TABLE IV

COMPARISON BETWEEN TDS AND OTHER BCIS/TCIS

| Reference | Type | Response Time (s) | Number of Commands | ITR (bits/min) |
|---|---|---|---|---|
| Wolpaw et al.[1] | EEG-BCI | 6~8 | 2-4 | 25.2 |
| Chen[2] | Indirect-BCI | 9.8 | 30 | 24.6 |
| Lau et al.[3] | TCI | 3.5 | 9 | 39.8 |
| Andreasen[4] | TCI | 2.4 | 5 | 57.6 |
| Huo et al.[5] | TCI | 1.5 | 6 | 87 |
| Present System | TCI | 0.8 | 6 | 140 |

[1]Wolpaw, J. R., Birbaumer, N., McFarland, D. J., Pfurtscheller, G., and Vaughan, T. M. Brain-computer interfaces for communication and control, Clinical Neurophysiology. 2002; 113: 767-791
[2]Y. L. Chen et al., "The new design of an infrared-controlled human-computer interface for the disabled," IEEE Trans Rehabilitation Eng., vol. 7, pp. 474-481, 1999.
[3]C. Lau, S. O'Leary, Comparison of computer interface devices for persons with severe physical disabilities, Am J. Occup. Ther., 47(11), pp. 1022-30, November 1993.
[4]L. N. S. Andreasen Struijk, "An inductive tongue controlled interface for control of computers and assistive devices," IEEE Trans. Biomed. Eng., vol. 53, pp. 2594-2597, 2006.
[5]X. Huo, J. Wang, M. Ghovanloo, Using magneto-inductive sensors to detect tongue position in a wireless assistive technology for people with severe disabilities, Proc. IEEE Sensors 2007, pp. 732-735, October 2007.

Test II: Maze Navigation

This experiment examines the TDS performance in navigation tasks in a controlled and safe environment on a computer screen. The subjects navigated the mouse cursor within a maze shown on the screen from a starting point by issuing a double-click (i.e., a start command) to a stopping point with a single-click (i.e., a stop command), while the GUI was recording the cursor path and measuring the elapsed time (ET) between the starting and stopping commands. The maze was designed to cause the user utilize most, if not all, the TDS commands, and the cursor was allowed to move towards the stop point only within the track. Whenever the user deviated from the track, the subject had to return the cursor back on the track and move it carefully, accurately, and as quickly as possible to minimize the ET. Every subject was asked to repeat this task for three times and the average ET was calculated.

Figure 27A:
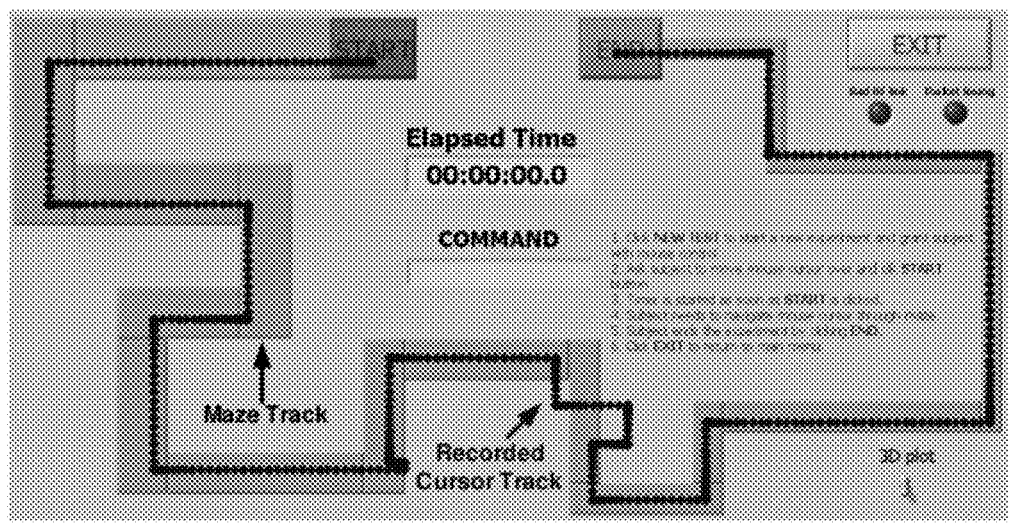
FIG. 27A is a view of a cursor path recorded during a maze navigation experiment imposed on a graphical user interface track, in accordance with an exemplary embodiment of the present invention.
Figure 27B:
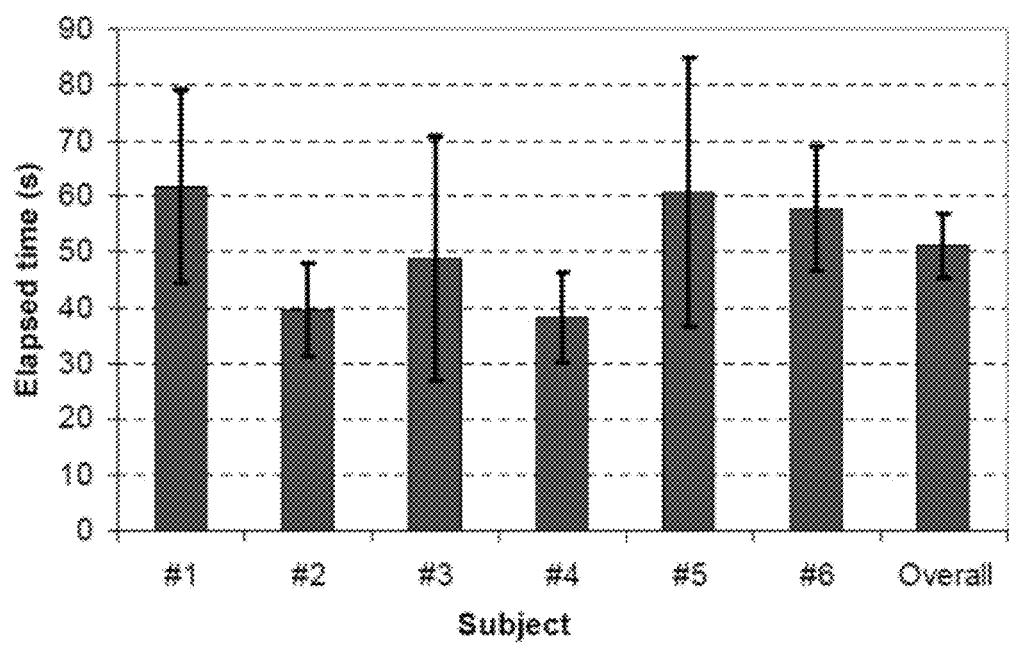
FIG. 27B is a graphical representation of mean values and 95% confidence interval of elapsed time for different subjects to complete a maze navigation experiment and the overall average of same, in accordance with an exemplary embodiment of the present invention.

FIG. 27A depicts one of the mouse cursor trajectories recorded during the maze navigation experiment, superimposed on the maze track displayed on the GUI. Although the subject has missed the track at some of the corners, the subject has managed to bring the cursor back on track and complete the task. The average ET of all 24 navigation experiments was about 51.19 seconds, as shown in FIG. 27B, which was about 2.5 times longer than the time required for one of the subjects to navigate the mouse cursor through the maze using his hand. Considering the fact that the subjects had much more prior experience in moving the mouse cursor with their hand than with their tongue, this experiment showed the potential of the TDS for performing complicated navigation tasks such as controlling a wheelchair in a crowded environment by quadriplegics.

Example

Another non-limiting example included human trials to evaluate the performance of TDS-PWC interface. Several experiments were designed and conducted to evaluate the performance of the TDS-PWC interface. Currently, the experiment results of one able-bodied 26 year-old male subject have been included. The experiment preparation including magnet attachment, system familiarization, and proper tongue position searching was completed according to the procedure explained in the above non-limiting example. During training session, the subject was asked to associate four tongue movements to the main four direction commands and his tongue resting position to the NEUTRAL command. The maximum PWC speed and rotation rates were set to about 0.5 m/s and about 36 degree/s, respectively. The acceleration time from about zero to the maximum was set to about 4 seconds in all directions. The deceleration time from maximum speed to stationary was set to about 1 second.

Test I: 90° Left-Turn Maneuver

Figure 28A:
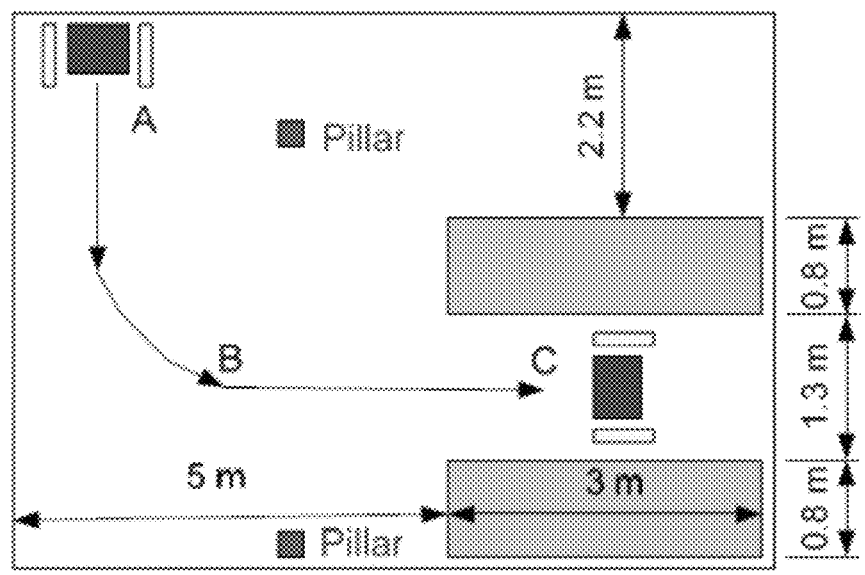
FIG. 28A is a view of a test for an experiment showing about a 90 degree left turn maneuver in the tongue drive system powered wheelchair test providing approximate powered wheelchair trajectory, in accordance with an exemplary embodiment of the present invention.

A purpose of this experiment was to familiarize the subject with the TDS-PWC interface. FIG. 28A depicts a layout of the user's environment and the approximate trajectory of the PWC. The subject was asked to start from position-A, and go forward by continuously issuing a FORWARD command. After reaching position-B, he was to make a left turn and enter a narrow aisle created by setting tables in a laboratory. The subject was allowed to make adjustments if he could not complete the task in one turn. Finally, he was asked to go straight and to reach destination-C. This test was successfully repeated five times.

Figure 28B:
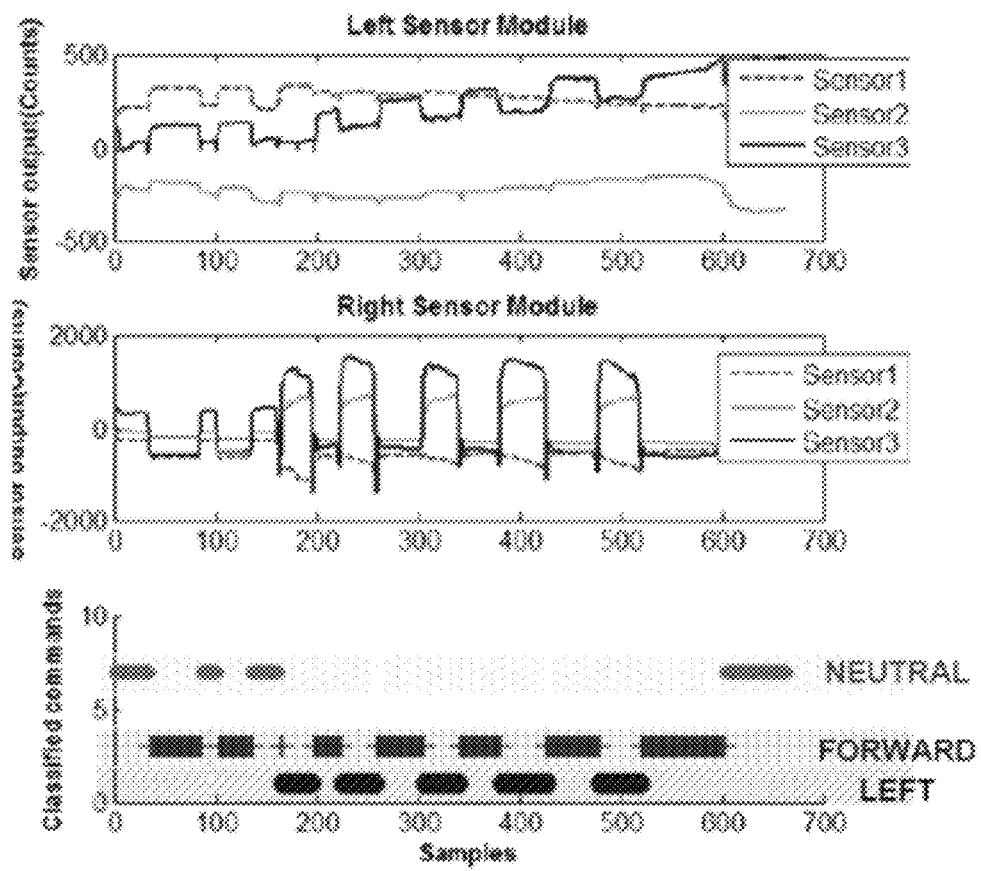
FIG. 28B is a graphical representation of results of a test for an experiment showing about a 90 degree left turn maneuver in the tongue drive system powered wheelchair test providing magnetic sensor output waveforms and classified control commands during said experiment, in accordance with an exemplary embodiment of the present invention.

FIG. 28B shows the magnetic sensor output waveforms and the issued commands that were recorded during one of these trials. As shown, the subject has made five smaller left turns followed by FORWARD commands to complete the required 90-degree turn and adjust the PWC to enter the aisle.

Test II: PWC Navigation in a Complex Path

Figure 29:
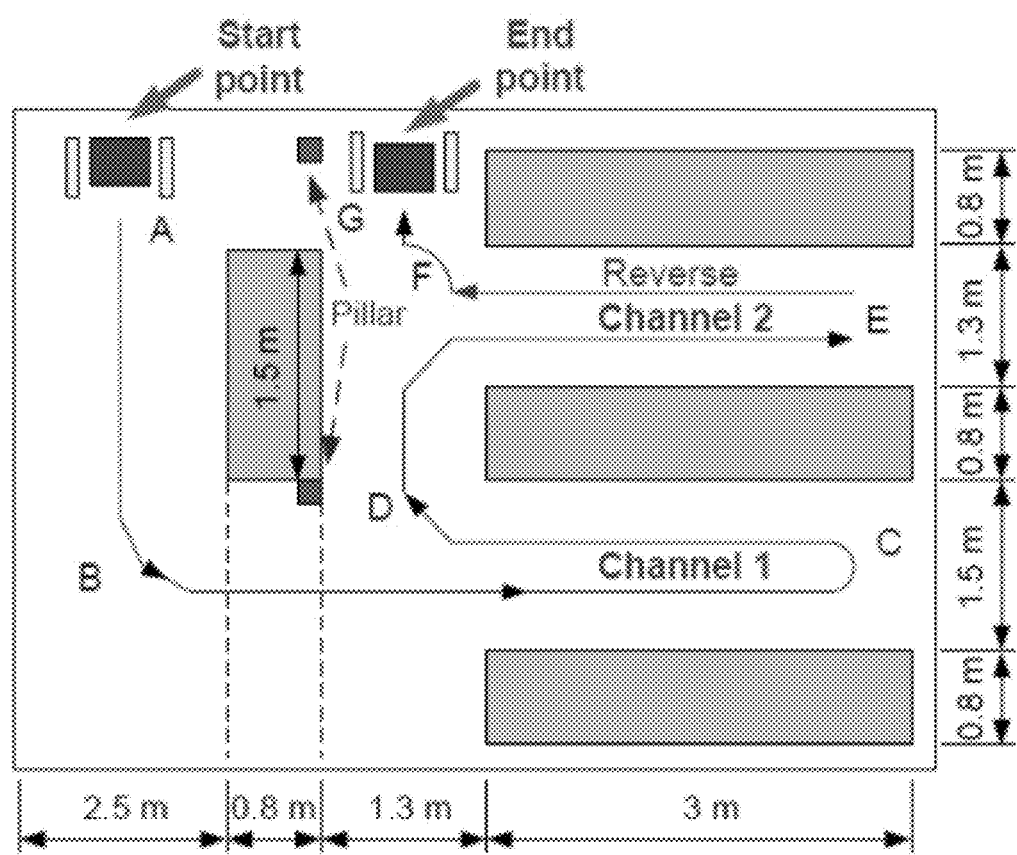
FIG. 29 is a view of a plan of a designated path showing the obstacles and approximate powered wheelchair trajectory for complex maneuvers in a tongue drive system powered wheelchair control test, in accordance with an exemplary embodiment of the present invention.

In this experiment, a complex path was created to require the subject to use all TDS-PWC control commands and perform various navigation tasks such as making a U-turn, backing up, and fine tuning the PWC direction in a limited space, while moving forward or backward. FIG. 29 shows an exemplary plan of the designated path and the approximate PWC trajectory. The channel-1 was wide enough for the subject to make a U-turn at position-C. The preferable way he could get out of channel-2 was to backup the PWC by issuing a BACK command from position-E and make some left and right fine adjustments along channels-2 to avoid hitting the preplaced obstacles. The subject made a 90 degree left turn at position-F and went forward to reach the destination-G. This task was also successfully repeated five times, and it took an average of about 145 seconds.

The tongue drive system is a wireless, unobtrusive, minimal invasive tongue-operated assistive device that is developed to enable people with severe disabilities to lead an independent self-supportive life by allowing them to control their environment using their tongue. One goal in development of the tongue drive system was to give a person that is paralyzed from neck below maximum flexibility in effectively using a computer and operating a wheelchair.

The system can wirelessly track the movements of the tongue by detecting the position of a permanent magnetic tracer secured on the tongue utilizing an array of magnetic sensors. The tongue movements can be translated into different commands and used to access a computer or control a motorized wheelchair, phone, TV, robotic arms, FES devices, or other equipments in user's environment.

The tongue drive system can not only help quadriplegics but also give an additional degree of control to able-bodied individuals when operating demanding machinery or vehicles. The tongue drive system provides an additional mechanism to aid a pilot, astronaut, or scuba diver communicate with the plane, spaceship, or submarine on-board computer, while operating other devices and controls with their hands and feet. It can also prove to be very useful in space or under water missions where the astronaut or scuba diver's hands and fingers are restricted in heavy and thick space or scuba diving suites.

In developed prototypes, an array of high sensitive magneto-inductive sensors are mounted onto a helmet, faceguard, hardhat or headgear and close to user's cheek to detect the magnetic field variation around user's mouth resulted from the movement of a small rare earth permanent magnet which is attached to user's tongue using tissue adhesive. After being wirelessly transmitted to a nearby processing system, the sensor outputs are fed into SSP algorithm based on principle component analysis (PCA) and K-Nearest-Neighbors (KNN) classifier and translated into different control commands. The translated commands can then be used to control the mouse cursor movements and emulate the button clicks in computer access.

Different external magnetic interference (EMI) cancellation techniques including using a 3-D electronics reference compass and a novel differential field cancellation algorithm can be implemented to minimize the effect of EMI, such as the earth magnetic field (EMF) variation due the movement and rotation of the user. Experiment results show that the sensor outputs after cancellation is much cleaner and effectively free of EMI. As a result, the signal-to-noise ratio (SNR) is enhanced and the accuracy of command interpretation is increased.

Lab-based human trials on six able-bodied male subjects have demonstrated that these TDS prototypes have the potential to substitute the lost arm and hand functions with tongue movements in accessing a computer by controlling the mouse cursor movements and button clicks with about direct commands. The minimum system response time was measured to be about 0.8 s with about 90% accuracy, and the information transfer rate was calculated as approximately 140 bits/min.

A customized TDS-PWC interface, comprising of an adapter circuitry and a graphical user interface (GUI), can link an external TDS prototype with a commercial powered wheelchair (PWC). Different PWC control strategy can be chosen based on user's preference. The human trials demonstrated that this TDS-PWC interface is fully functional, and can be used to control a PWC through about five individual commands.

Calibration

Figure 30:
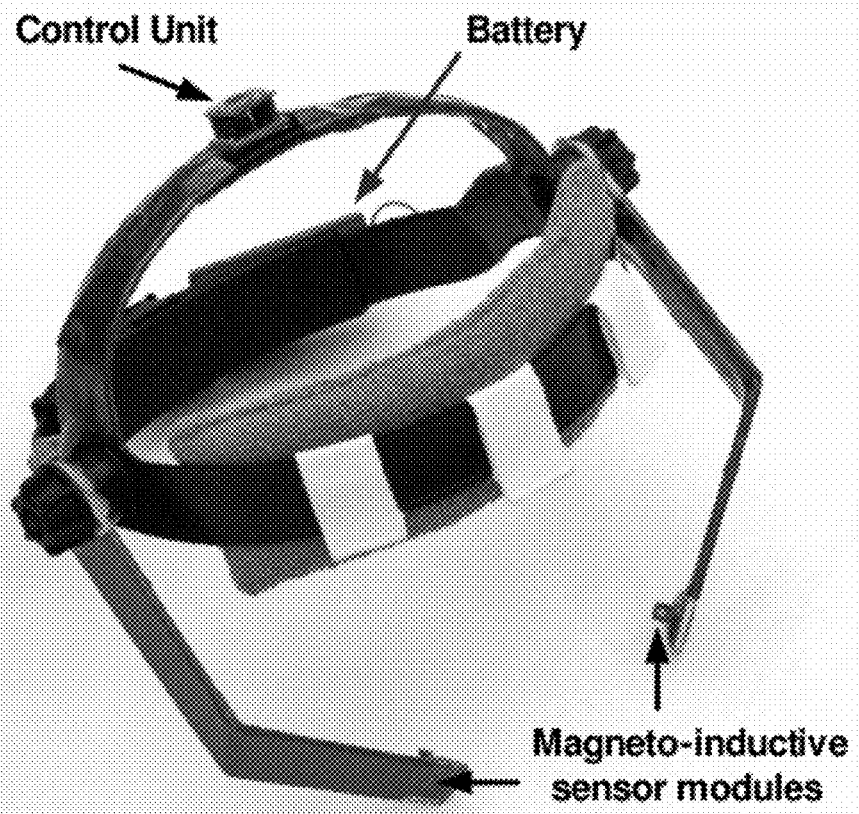
FIG. 30 is a perspective view of a headgear carrying embodiments of the assistive system, in accordance with an exemplary embodiment of the present invention.

In another exemplary embodiment, the tongue drive system can be built as an external tongue drive system, wherein a headgear is adapted to receive and interpret the magnetic field of the tracer unit. For example, an external tongue drive system (eTDS) can be built on a headgear to be adjustable for different subjects with different head sizes, as depicted in FIG. 30 (as well as FIGS. 43A-43B and FIGS. 44A-44D). In an exemplary embodiment, two 3-axial magnetic sensors can be mounted bilaterally on the headgear and a control unit is located on the top of headgear to collect the output of sensors and sent them out to the PC through a wireless link.

Figure 31:
FIG. 31 is a top view of a magnet used as a tracer unit, compared to a U.S. quarter coin, in accordance with an exemplary embodiment of the present invention.

In addition, the tongue drive system can include a tracer unit, which may be a magnetic tracer unit in some embodiments. For instance, a small permanent magnet in the size of Ø5 mm×1 mm and residual magnetization of 10800 Gauss at the surface can be used as the tracer for eTDS prototype. A depiction of this exemplary tracer is shown in FIG. 31, beside a U.S. quarter coin.

Further, the tongue drive system can include a wireless receiver. For example, a wireless receiver can be a USB wireless receiver. Wireless data can be transmitted from the headgear of the tongue drive system to be received by the USB wireless receiver and then fed to a processing system for further processing.

Moreover, a tissue adhesive can be used to adhere the magnet to the tongue. For example, cyanodent dental adhesive from Ellman International Inc., Oceanside, N.Y. can be used for this adhesion. Additionally, anti-magnetic tweezers can be used to hold the magnet when one applies glue onto the surface of magnet and put the magnet on the surface of the tongue.

In some embodiments, the tongue drive system utilizes a novel calibration process to calibrate the tracer unit to the external sensor system. A purpose of the calibration system is to enable the sensors to communicate properly with the magnet. The system calibration can obtain the linear regression coefficients used in stereo differential signal processing algorithm by recording and analyzing the pure environment magnetic field. A differential signal processing algorithm can cancel out the interference of external magnetic field when the subject is moving around. This process can be performed before attaching the magnetic tracer onto subject's tongue because the data fed into calibration program should only include the information related to the external magnetic field and not the magnetic tracer.

Initially, the user can communicate to the processing system that they are entering a calibration mode. For example, by clicking the CALIBRATION button on the main GUI window. A new GUI named CALIBRATION SESSION will show up, as shown in FIG. 32. Next, the user can change the Testing Data Point to 500 by moving the red slide (in oval of FIG. 32) all the way to the right. Then, the user can click the START button and ask the subject to move around near the experimental space, while moving his/her head and look around.

The GUI starts recording the sensor outputs and will automatically stop when a predetermined number of data points have been sampled, for example and not limitation, about 500 data points. During data recording, the user can observe the sensor output in the waveform chart, which should change along with subject's movement.

The calibration coefficients can be automatically calculated based on these data points and a data file can be created.

The operator can also open the created file, for example, in a MATLAB or like software program, and check the content. The operator may see six images (similar to FIGS. 33A-33B) showing the results of calibration. The curve along "0 counts" may stay around zero, which indicates that the external magnetic field has been effectively predicted and cancelled.

The variation of green curves within 100 counts is an acceptable calibration result. If the variation of any curve is larger than 100 counts, the operator may recalibrate the system by repeating the same above procedure. The system calibration is now completed.

After the system calibration is completed, the operator can follow non-limiting procedure to attach the magnet on the subject's tongue, e.g., using Cyanodent dental adhesive:

a) Wash the magnet with water (e.g., tap water), ensure the surface is clean and there is no residual adhesive.
b) Place the magnet in isopropyl alcohol (rubbing alcohol) for about 5 min for disinfection.
c) Remove the magnet with anti-magnetic tweezers, which tips have also been immersed in alcohol, and put it on a clean paper towel to dry.
d) Dry the subject's tongue. For example, ask the subject to hold his/her tongue out for about 2-3 min to dry. Alternatively, a hair dryer can be used at low heat to dry the tongue more quickly.
e) Remove the cap of a dental adhesive and apply one or two drops of glue on the magnet from its small bottle. Then, carefully replace the cap and seal the adhesive, because it can dry rapidly.
f) Pick the magnet with the tweezers and carefully attach the magnet to subject's tongue, about 5 mm from the tip, as shown in FIG. 3B.
g) Wait for about 1 min for the adhesive to dry. Press the magnet using tweezers from time to time during drying. Do not leave the tweezers on the magnet surface for too long because the residual adhesive on magnet may ultimately stick to the tweezers.
h) Ask the subject to move his/her tongue around inside the mouth to get familiar with the feeling of a magnet attached to his/her tongue. It may feel a bit odd at the beginning. The subject, however, will get used to it very soon.
i) The subject may also be asked to inform the operator at any point during the experiments, as soon as he/she feels that the magnet has become loose or detached from his/her tongue. In such situations, the operator should stop the experiment immediately, and the user should avoid swallowing or chewing the magnet by having it removed from his/her mouth.
j) The operator and subject can then decide whether to remove the residues, reapply the tissue adhesive, retrain the system, and continue with the experiments, or do the entire test at a later time.

Finding Proper Tongue Positions to Define Commands

In an exemplary embodiment, the user may find proper tongue positions to define certain commands. Initially, the subject may be positioned to sit about one meter away from a computer screen. Preferably, no obstacles are placed between the subject and a wireless receiver.

Figures 34, 35:
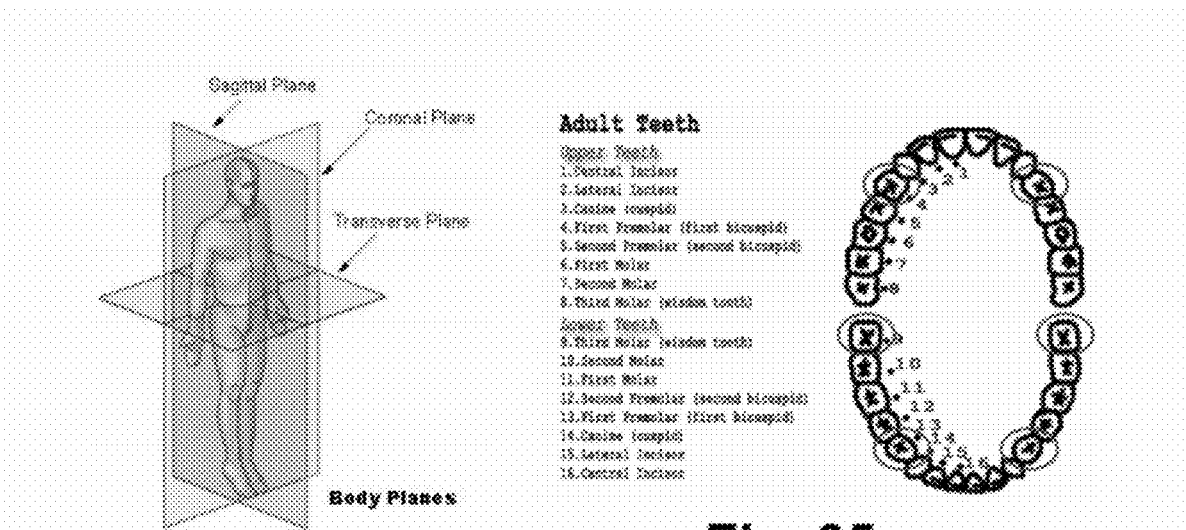
FIG. 34 is a conventional view of body planes of a human.
FIG. 35 is a diagram of adult human teeth indicating exemplary positions for defining the tongue drive system commands, in accordance with an exemplary embodiment of the present invention.

Then, the subject can determine recommended tongue positions for defining the TDS commands. In general, it is preferable that the user avoid defining any commands in the center of the mouth (i.e., sagittal plane) because those tongue movements are common during vocation and speech, as shown in FIG. 34. The TDS commands can be defined by touching different teeth by the tip of the tongue. It might not be easy for every subject to do that because the magnet is attached close to the tip and affects the flexibility of the tongue tip. In some embodiments, the subject can apply force to their tongue and push the magnet on the surface of different teeth to define the commands. The exemplary positions for defining the commands are:

Root of the fourth bottom tooth on the left—Left;
Root of the fourth bottom tooth on the right—Right;
Root of the fourth top tooth on the left—Up;
Root of the fourth top tooth on the right—Down;
The most left tooth/Left cheek—Click;
The most right tooth/Right cheek—Double-click,
which are identified in FIG. 35 (see ovals).

Figure 36:
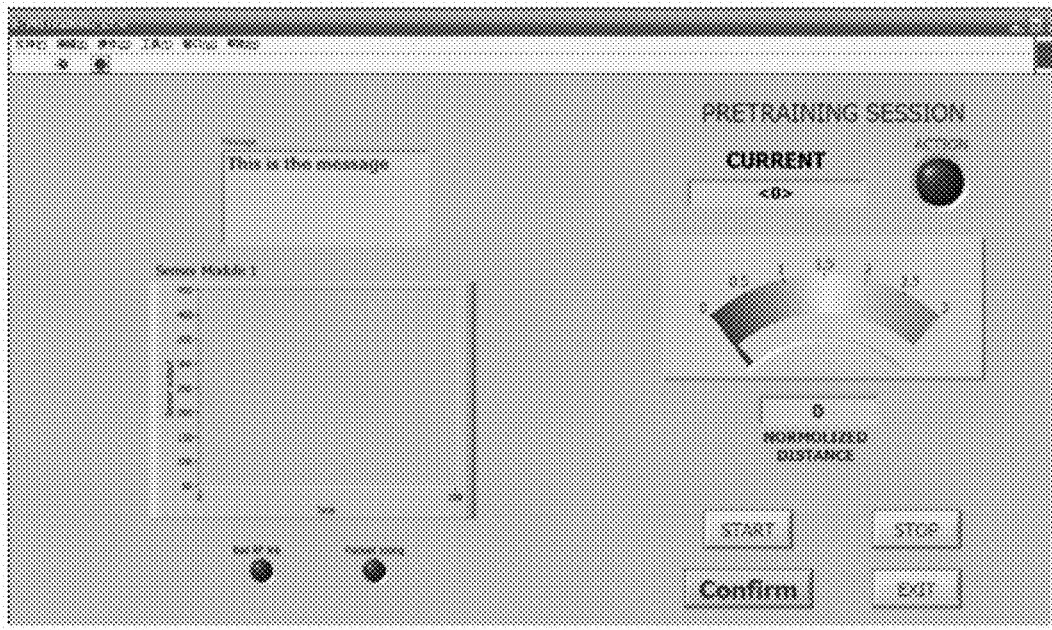
FIG. 36 is a view of a graphical user interface for a pre-training session, in accordance with an exemplary embodiment of the present invention.
Figure 37:
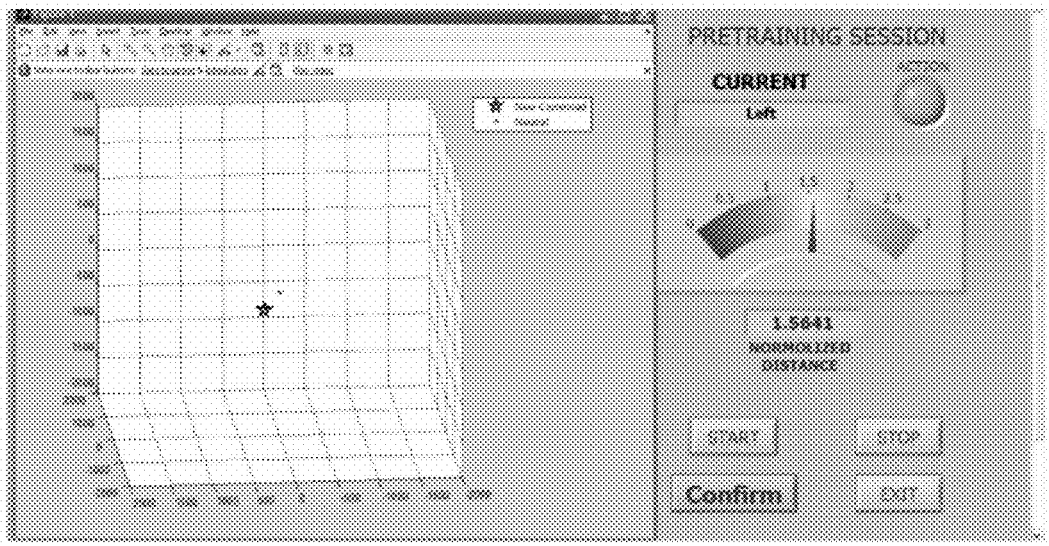
FIG. 37 is a view of a graphical user interface illustrating an exemplary configuration of MATLAB and LabVIEW windows demonstrating a three-dimensional representation of the tongue position in a pre-training session, in accordance with an exemplary embodiment of the present invention.

Then the operator can launch the pre-training GUI, as shown in FIG. 36 by clicking the PRE-TRAINING button on the main GUI. The operator can click the START button to start the pre-training session. A MATLAB figure may be opened over the pre-training session window. If it does not happen, one may need to click the figure tab on task bar to display the figure on top of the LabVIEW window. It may be necessary to adjust the size and re-position the figure so that the subject can clearly see what is being displayed in the figure. The operator next can confirm to have access by clicking the CONFIRM button located in the button right corner of the GUI. One exemplary configuration is shown in FIG. 37.

The operator can explain the principle and components of the pre-training GUI to the subject. The pre-training GUI displays the "virtual position" of magnet represented by a set of green stars based on calibrated magnetic sensor vectors, in a virtual 3D space. The green stars move as the subject moves his/her tongue around. Therefore, the positions of these stars in some senses reflect the positions of the magnet within subject's mouth. In order to find good position to define commands, the subject will be asked to move his/her tongue to different positions, while the operator observes the position of the green stars and determine whether the position is good or not. To determine whether it is a good definition or not is that the subject should be able to hold his/her tongue at that position stationary (the green stars converge to one points), and the distance between current position of the star and any previous positions are far enough to be distinguished.

Next, it may be necessary to help subject to find proper positions to define LEFT and RIGHT commands. Initially, the subject may rest his/her tongue at its original position. When the green stars are stabilized to one point, the user can click the CONFIRM button to register the position of NEUTRAL (RESTING) command. A registered command will be displayed as a set of fixed points in the space. FIG. 37 shows that the NEUTRAL command has been registered as blue dots and the green star continues moving with subject's tongue to identify next command.

The subject can move his/her tongue to LEFT command position. Then, the subject can wait until green stars are stabilized. In order to have a better view over a three-dimensional space, the operator can rotate the space by clicking the ROTATE 3-D button on MATLAB toolbar, and move the mouse cursor within the figure while the left-click button is held down. The LEFT command can be registered by clicking the CONFIRM button in the LABVIEW GUI. Continue RIGHT command with the same procedure. It may be desirable for the operator to make sure LEFT, RIGHT and NEUTRAL commands are separated as much as possible.

After the LEFT, RIGHT and NEUTRAL commands are all identified, the operator can click STOP button to stop the session and then click EXIT to return to the main GUI and continue with the next step.

Figure 40:
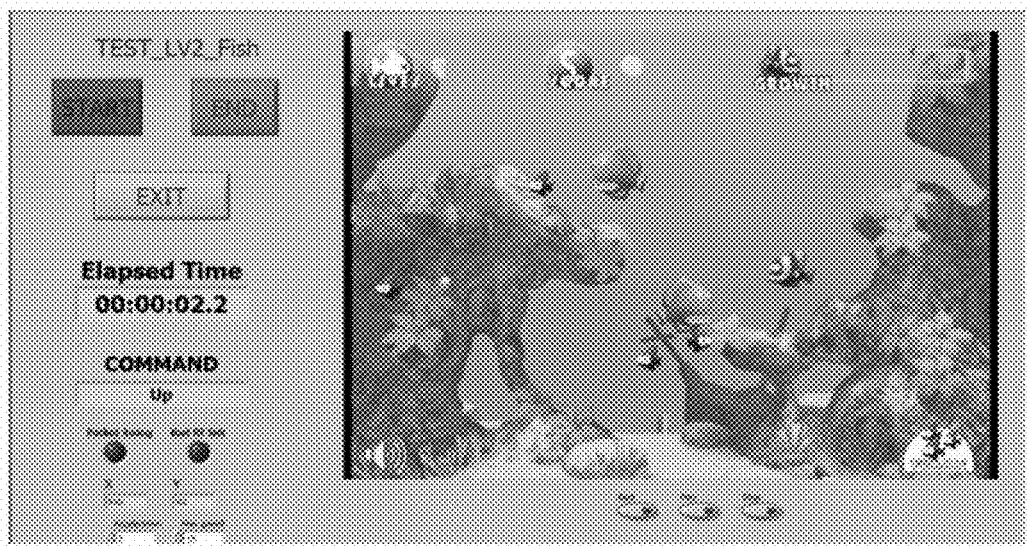
FIG. 40 is a view of a graphical user interface for a computer game that can be played using embodiments of the present invention, in accordance with an exemplary embodiment of the present invention.

Once the users successfully train the tongue drive system with their desired tongue commands, they can substitute the mouse their tongue motion as a way of accessing the computer, and start using their computers for a variety of tasks such as entertainment. FIG. 40 is a view of a graphical user interface for a free computer game called "Fish Tales" that uses four commands for cursor movements. It can be played using embodiments of the present invention, in accordance with an exemplary embodiment of the present invention.

Commands Adjustment

Figure 41:
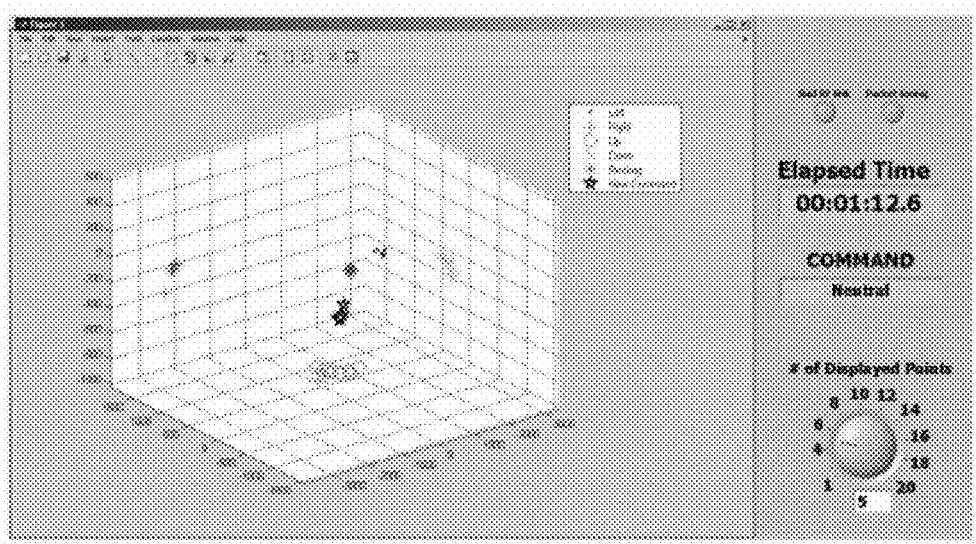
FIG. 41 is a view of a graphical user interface illustrating an exemplary configuration of MATLAB and LabVIEW windows demonstrating the three-dimensional representation of the tongue position after the training session along with graphical representation of data clusters representing different commands, in accordance with an exemplary embodiment of the present invention.
Figure 42:
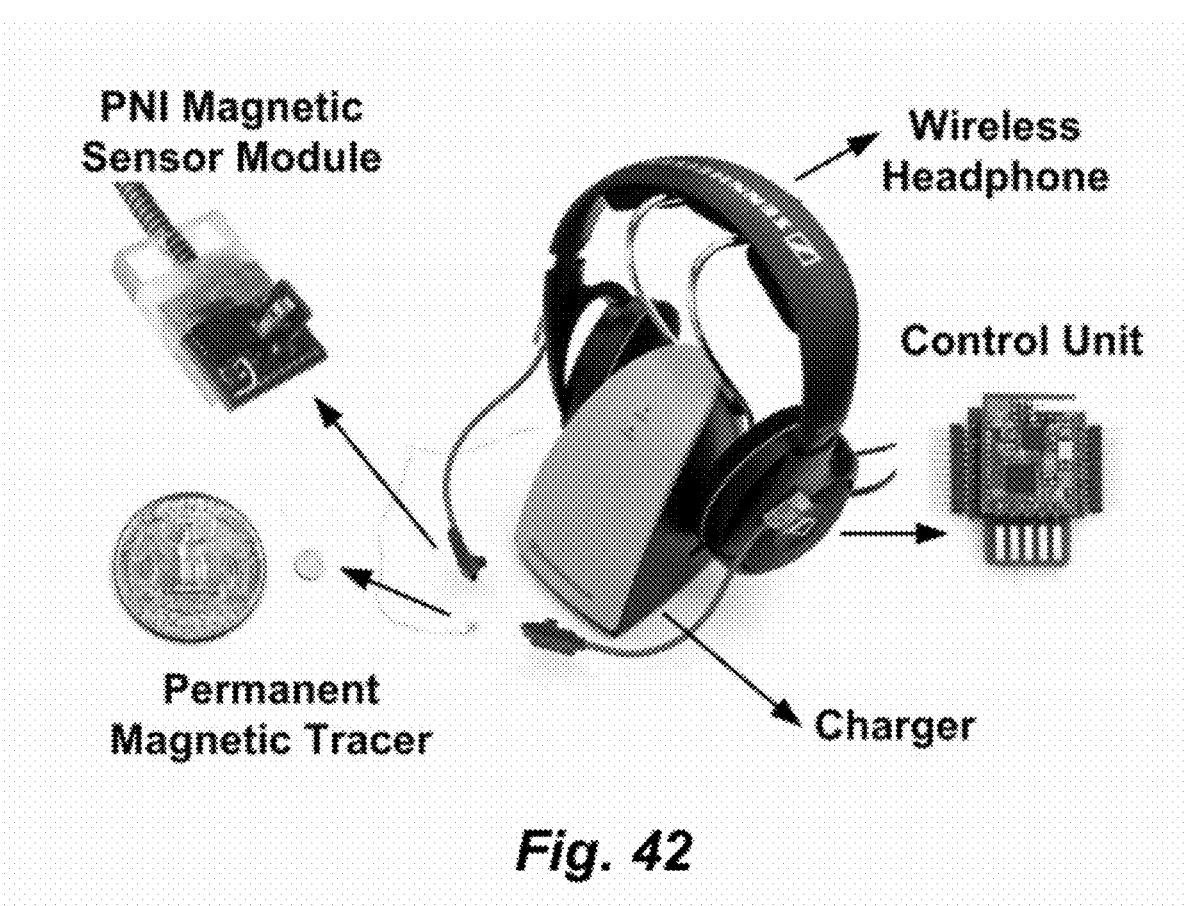
FIG. 42 is a perspective view of a wireless headphone and its charger carrying embodiments of the assistive system, in accordance with an exemplary embodiment of the present invention.
Figure 43A:
FIGS. 43A-43B are perspective views of a wireless headphone carrying a tongue drive system, in accordance with an exemplary embodiment of the present invention.
Figure 43B:
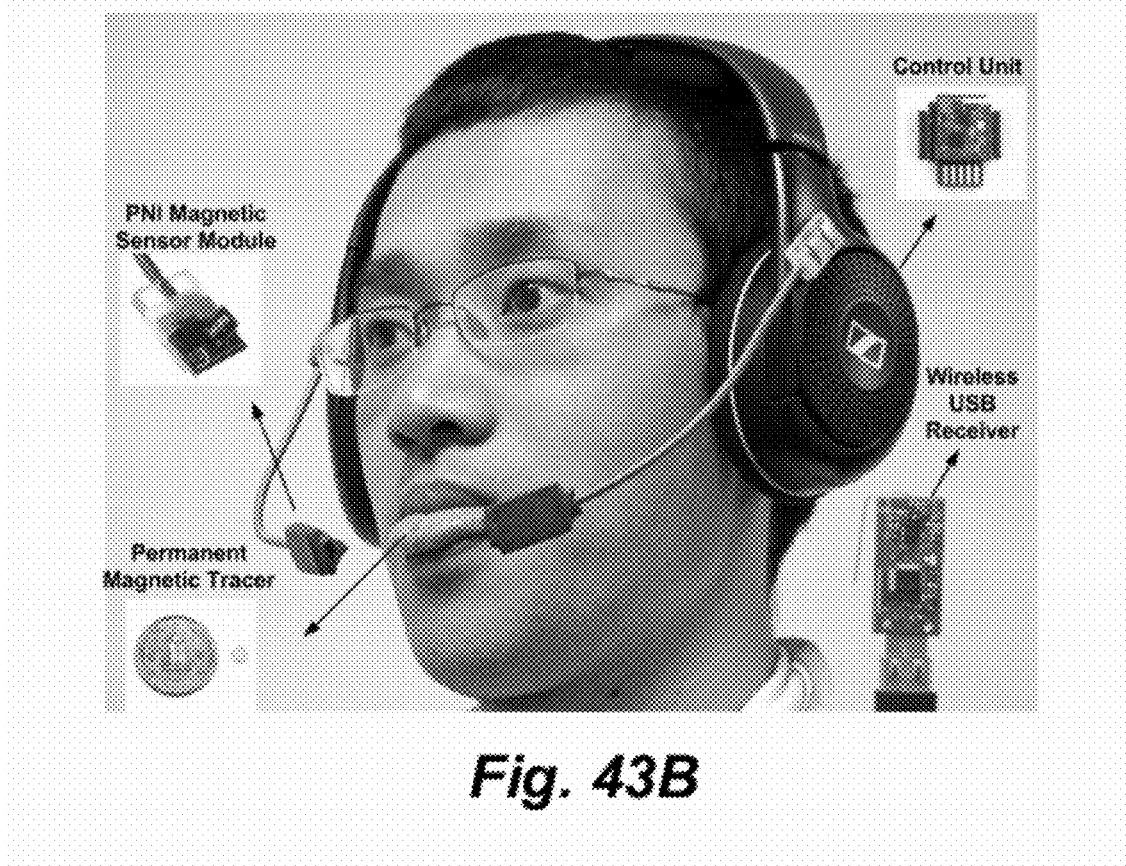
Figure 44A:
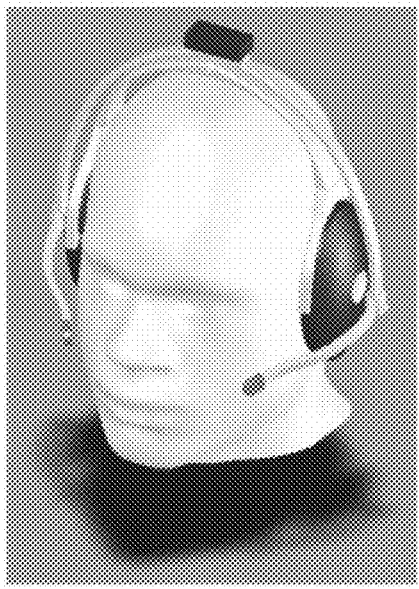
FIGS. 44A-44D are perspective views of a headset with extra wings for magnetic sensors, carrying a tongue drive system, in accordance with an exemplary embodiment of the present invention.
Figure 44B:
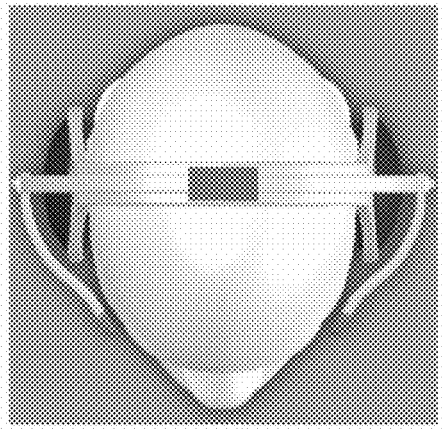
Figure 44C:
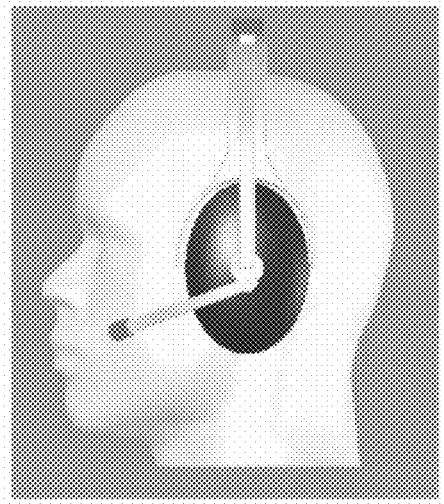
Figure 44D:
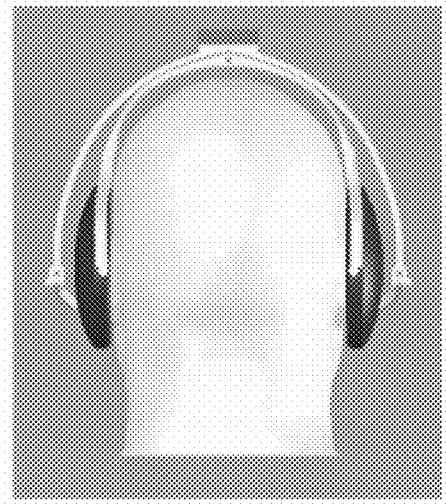

In an exemplary embodiment, the user may redefine or adjust the position of certain tongue command, which position may have shifted, without going through a complete re-training process. FIG. 41 is a view of a graphical user interface providing visual feedback on the present status of the tongue drive system to the users to assist them to re-define their tongue commands in case the original definition has shifted as a result of minor changes in the position of the sensors. Another option in this case is to recalibrate and retrain the system with the new sensor positions. On the left side of the figure, seven data clusters representing different command positions obtained during training session are plotted in a virtual three-dimensional mouth space to represent the correct tongue positions for those commands. The current tongue position is displayed as a star, which moves around when users' tongues move. By issuing a certain command, users can observe how far their tongues have deviated from the trained position of that command. Hence they can move their tongues around that position to move the green star closer to the desired command cluster within the space. When the star is close enough to correct cluster and the classified command, showing on the GUI, also agrees with the desired one, the new command position is identified for the users.

In one aspect, a method of tracking movement, position, orientation, or all three of a tongue of a subject is provided. The comprises positioning a tracer unit on the tongue of the subject in a non-obstructively manner; positioning a sensor system in proximity to the tongue carrying the tracer unit; and calibrating the sensor system relative to the tracer unit for detecting the position of the tracer unit.

In some embodiments, the method further comprises generating a signal based on the position of the tracer unit. In some embodiments, the method further comprises analyzing the signal to thereby track movement, position, or orientation of the tongue. In some embodiments, the method further comprises transmitting the signal to an appliance, wherein the signal is adapted to control the appliance.

In some embodiments, an assistive apparatus tracks movement, position, or both of the tongue, the apparatus comprising: the tracer unit; the sensor system for detecting position of the tracer unit and adapted for non-obstructive placement proximal the sensor system; and a control system for transmitting to a processing system. In some embodiments the tracer unit comprises a magnet. In some embodiments, the apparatus further comprises a plurality of sensors, a wireless transceiver, a control unit, and a power management block including a rechargeable battery in communication with a secondary coil, wherein the secondary coil is charged wirelessly. In some embodiments, the secondary coil is charged via an inductive charging system. In some embodiments, calibrating of the sensor system comprises calculating the magnetic field around the sensor system. In some embodiments, calibrating the sensor system further comprises removing environmental magnetic fields around the sensor system. In some embodiments, calibrating the sensor system further comprises calculating a difference of the magnetic field of the sensory system and the magnetic field emitted by the tracer unit.

In one aspect, an assistive system for remotely controlling an appliance by a user is provided. The system comprises a tracer unit adapted to be non-obstructively affixed to a tongue of the user, wherein a change in position of the tongue of the user changes position of the tracer unit; a sensor system comprising at least one sensor, the sensor system detecting a position of the tracer unit and adapted for non-obstructive placement in proximity to the tracer unit; a sensor control unit for transmitting a sensor signal to an appliance based on the detected position of the tracer unit; a secondary coil adapted to be inductively coupled to a magnetic field; and at least one rechargeable battery adapted to be charged by the secondary coil.

In some embodiments, the tracer unit comprises a magnet. In some embodiments, the sensor system is adapted to be placed within the mouth of the user. In some embodiments, the sensor system is adapted for positioning outside the mouth of the user. In some embodiments, the appliance is selected from the group consisting of a processing system, a powered wheelchair, a bed, a telephone, a home appliance, a speech synthesizer, and a keyboard.

In some embodiments, the system further comprises a power charging station comprising a primary coil adapted to emit the magnetic field for inductively charging the secondary coil.

In some embodiments, the secondary coil is in communication with a rechargeable battery, wherein when the secondary coil is inductively coupled to the magnetic field that rechargeable battery recharges.

In one aspect, a method of tracking one or more of movement, position, orientation of a tongue of a user is provided. The method comprises positioning a tracer unit on the tongue of the user in a non-obstructively manner; positioning a sensor system in proximity to the tongue carrying the tracer unit; calibrating the sensor system relative to the tracer unit; defining positions of the tracer unit relative to the sensor system; and detecting the position of the tracer unit.

In some embodiments, defining position of the tracer unit relative to the sensor system occurs by switch-based control schemes or continuous control schemes.

While exemplary embodiments of the invention have been disclosed many modifications, additions, and deletions can be made therein without departing from the spirit and scope of the invention and its equivalents, as set forth in the following claims. In addition, the quantities of various features of embodiments of the present invention are provided for illustrated embodiments and are exemplary. The scope of the various embodiments of the present invention should not be limited to the above discussed embodiments or quantity values, and should only be defined by the following claims and all applicable equivalents.

What is claimed is:

1. A method of tracking movement, position, or both of a tongue of a subject, the method comprising:
   positioning a tracer unit on the tongue of the subject in a non-obstructively manner;
   positioning a sensor system, of at least two 3-axial magnetic sensors, in proximity to the tongue carrying the tracer unit; and
   calibrating the sensor system relative to the tracer unit for detecting the position of the tracer unit, wherein the magnetic field around the sensor system is calculated in real-time and environmental magnetic fields around the sensor system are removed using differential EMI cancellation by the at least two 3-axial sensors.

2. The method of claim 1, further comprising generating a signal based on the detected position of the tracer unit.

3. The method of claim 2, further comprising analyzing the signal to thereby track movement, position, or orientation of the tongue.

4. The method of claim 3, further comprising transmitting the signal to an appliance, wherein the signal is adapted to control the appliance.

5. The method of claim 1, wherein an assistive apparatus tracks movement, position, or both of the tongue, the apparatus comprising:
   the tracer unit;
   the sensor system for detecting position of the tracer unit and adapted for non-obstructive placement proximal the sensor system; and
   a control system for transmitting to a processing system.

6. The method of claim 5, the tracer unit comprising a magnet.

7. The method of claim 5, the apparatus further comprising a plurality of sensors, a wireless transceiver, a control unit, and a power management block including a rechargeable battery in communication with a secondary coil, wherein the secondary coil is charged wirelessly.

8. The method of claim 1, wherein calibrating the sensor system further comprises calculating a difference of the magnetic field measured by the sensory system and the magnetic field emitted by the tracer unit.

9. The method of claim 1, wherein calibrating the sensor system relative to the tracer unit for detecting the position of the tracer unit further comprises adjusting at least one of the defined positions of the tracer unit according to an oral anatomy of a user.

10. A method of tracking one or more of movement, position, orientation of a tongue of a user, the method comprising:
    positioning a tracer unit on the tongue of the user in a non-obstructive manner;
    positioning a sensor system, of at least two 3-axial magnetic sensors, in proximity to the tongue carrying the tracer unit;
    calibrating the sensor system relative to the tracer unit, wherein the magnetic field around the sensor system is calculated and magnetic noise is suppressed in real-time using differential EMI cancellation by the at least two 3-axial magnetic sensors;
    defining positions of the tracer unit relative to the sensor system; and
    detecting the position of the tracer unit.

11. The method of claim 10, wherein defining position of the tracer unit relative to the sensor system occurs by switch-based control schemes or continuous control schemes.

12. The method of claim 10, further comprising redefining at least one of the defined positions of the tracer unit relative to the sensor system based on use of the sensor system.

13. The method of claim 10, wherein at least one of the defined positions of the tracer unit relative to the sensor system is adjusted according to a characteristic of an oral anatomy of a user.

14. The method of claim 10, further comprising discriminating between natural, non-controlling tongue movements and volitional, controlling tongue commands by defining positions of the tracer unit relative to the sensor system.

15. An assistive system for remotely controlling an appliance by a user, the system comprising:
    a tracer unit adapted to be non-obstructively affixed to a tongue of the user, wherein a change in position of the tongue of the user changes position of the tracer unit;
    a sensor system comprising at least two 3-axial sensors, the sensor system detecting a position of the tracer unit and adapted for non-obstructive placement in proximity to the tracer unit; and
    a sensor control unit for transmitting a sensor signal to a processing unit based on the detected position of the tracer unit;
    wherein the sensor signal is calibrated by the processing unit by detecting magnetic noise and suppressing the detected magnetic noise in real-time by differential EMI cancellation by the at least two 3-axial sensors.

16. The system of claim 15, wherein the detected magnetic noise comprises at least one selection of the group consisting of environmental magnetic fields, magnetic interference, natural tongue movements, tongue movements in the sagittal plane, and body movements.

17. The system of claim 15, wherein the sensor system detects the position of the tracer unit by accounting for at least one adjustment parameter.

18. The system of claim 17, wherein the at least one adjustment parameter is selected of the group consisting of an oral anatomy, an individual's needs, an individual's capabilities, an individual's lifestyle, an individual's environment, and an individual's health condition.

* * * * *